US00RE51111E

(19) United States
(12) Reissued Patent
de Almeida Barreto

(10) Patent Number: US RE51,111 E
(45) Date of Reissued Patent: *Nov. 10, 2026

(54) METHODS AND SYSTEMS FOR COMPUTER-AIDED SURGERY USING INTRA-OPERATIVE VIDEO ACQUIRED BY A FREE MOVING CAMERA

(71) Applicant: Smith & Nephew, Inc., Memphis, TN (US)

(72) Inventor: João Pedro de Almeida Barreto, Coimbra (PT)

(73) Assignee: SMITH & NEPHEW, INC., Memphis, TN (US)

( * ) Notice: This patent is subject to a terminal disclaimer.

(21) Appl. No.: 18/587,907

(22) Filed: Feb. 26, 2024

Related U.S. Patent Documents

Reissue of:
(64) Patent No.: 10,499,996
Issued: Dec. 10, 2019
Appl. No.: 15/561,666
PCT Filed: Mar. 25, 2016
PCT No.: PCT/US2016/024262
§ 371 (c)(1),
(2) Date: Sep. 26, 2017
PCT Pub. No.: WO2016/154557
PCT Pub. Date: Sep. 26, 2016

U.S. Applications:
(63) Continuation of application No. 17/548,202, filed on Dec. 10, 2021, now Pat. No. Re. 49,930, which is an application for the reissue of Pat. No. 10,499,996.
(Continued)

(51) Int. Cl.
*A61B 34/20* (2016.01)
*A61B 34/00* (2016.01)
(Continued)

(52) U.S. Cl.
CPC ..... *A61B 34/20* (2016.02); *A61B 34/10* (2016.02); *A61B 34/25* (2016.02); *A61B 34/30* (2016.02);
(Continued)

(58) Field of Classification Search
CPC ..... A61B 2034/2065; A61B 2034/301; A61B 2034/302; A61B 2090/365;
(Continued)

(56) References Cited

U.S. PATENT DOCUMENTS 5,313,306 A 5/1994 Kuban et al.
5,767,980 A 6/1998 Wang et al.
(Continued)

FOREIGN PATENT DOCUMENTS

EP 1759629 A1 3/2007
EP 2153794 A2 * 2/2010 ..... A61B 90/361
(Continued)

OTHER PUBLICATIONS

Li, X., et al., "Symmetry and Template Guided Completion of Damaged Skulls", Computers & Graphics, vol. 35, pp. 885-893, Jan. 31, 2011.
(Continued)

*Primary Examiner* — Robert L Nasser
(74) *Attorney, Agent, or Firm* — Dickinson Wright PLLC

(57) ABSTRACT

Disclosed is a concept for computer-assisted procedures of surgery and diagnosis that target rigid, non-deformable anatomical parts such as bone, tissue, or teeth. The disclosure describes attaching small visual markers to instruments and anatomy of interest (e.g. bone surface), with each marker having a printed known pattern for detection and unique identification in images acquired by a free-moving camera, and a geometry that enables estimating its rotation
(Continued)

and translation with respect to the camera using solely image processing techniques.

14 Claims, 23 Drawing Sheets

Related U.S. Application Data

(60) Provisional application No. 62/138,529, filed on Mar. 26, 2015, provisional application No. 62/255,513, filed on Nov. 15, 2015.

(51) Int. Cl.

| | |
|---|---|
| ***A61B 34/10*** | (2016.01) |
| ***A61B 34/30*** | (2016.01) |
| ***A61B 90/00*** | (2016.01) |
| ***G06F 3/03*** | (2006.01) |
| ***G06F 19/00*** | (2018.01) |
| ***G06T 7/50*** | (2017.01) |
| ***G06T 7/62*** | (2017.01) |
| ***G06T 7/73*** | (2017.01) |
| ***G06T 7/80*** | (2017.01) |
| ***G06T 19/00*** | (2011.01) |
| ***G16H 20/30*** | (2018.01) |
| ***G16H 20/40*** | (2018.01) |
| ***G16H 30/20*** | (2018.01) |
| ***G16H 30/40*** | (2018.01) |
| ***G16H 50/50*** | (2018.01) |
| ***H04N 13/221*** | (2018.01) |
| ***H04N 13/246*** | (2018.01) |

(52) U.S. Cl.

CPC ..... *A61B 90/361* (2016.02); *G06F 3/0321* (2013.01); *G06T 7/50* (2017.01); *G06T 7/62* (2017.01); *G06T 7/73* (2017.01); *G06T 7/85* (2017.01); *G06T 19/006* (2013.01); *G16H 20/30* (2018.01); *G16H 20/40* (2018.01); *G16H 30/20* (2018.01); *G16H 30/40* (2018.01); *G16H 50/50* (2018.01); *H04N 13/221* (2018.05); *H04N 13/246* (2018.05); *A61B 2034/2055* (2016.02); *A61B 2034/2057* (2016.02); *A61B 2034/2065* (2016.02); *A61B 2034/301* (2016.02); *A61B 2034/302* (2016.02); *A61B 2090/365* (2016.02); *A61B 2090/3937* (2016.02); *A61B 2090/3945* (2016.02); *A61B 2090/3983* (2016.02); *A61B 2090/3991* (2016.02); *G06T 2207/30208* (2013.01); *G06T 2207/30244* (2013.01); *G06T 2219/004* (2013.01)

(58) Field of Classification Search

CPC .... A61B 2090/3937; A61B 2090/3945; A61B 2090/3983; A61B 2090/3991; G06T 2207/30208; G06T 2207/30244; G06T 2219/004

See application file for complete search history.

(56) References Cited

U.S. PATENT DOCUMENTS

| | | | | |
|---|---|---|---|---|
| 5,792,147 | A | 8/1998 | Evans et al. | |
| 5,836,869 | A | 11/1998 | Kudo et al. | |
| 6,047,088 | A | 4/2000 | van Beek | |
| 6,072,496 | A | 6/2000 | Guenter et al. | |
| 6,449,103 | B1 | 9/2002 | Charles | |
| 7,429,999 | B2 | 9/2008 | Poulin | |
| 7,750,969 | B2 | 7/2010 | Sato | |
| 7,751,865 | B2 | 7/2010 | Jascob | |
| 7,808,525 | B2 | 10/2010 | Katayama | |
| 7,892,165 | B2 | 2/2011 | Nakamura | |
| 7,970,174 | B2 | 6/2011 | Goldbach | |
| 8,223,193 | B2 | 7/2012 | Zhao | |
| 8,771,177 | B2 | 7/2014 | Hale et al. | |
| 8,902,232 | B2 | 12/2014 | Debevec et al. | |
| 9,307,892 | B2 | 4/2016 | Dahmen | |
| 9,367,928 | B2 | 6/2016 | de Almeida Barreto et al. | |
| 9,398,840 | B2 | 7/2016 | Rehe | |
| 9,438,897 | B2 | 9/2016 | Barreto et al. | |
| 9,888,831 | B2 | 2/2018 | Yoshino | |
| 9,986,183 | B2 | 5/2018 | Baek et al. | |
| 10,499,996 | B2 * | 12/2019 | de Almeida Barreto | |
| RE49,930 | E * | 4/2024 | de Almeida Barreto | |
| 2004/0019274 | A1 | 1/2004 | Galloway, Jr. et al. | |
| 2004/0070565 | A1 | 4/2004 | Nayar et al. | |
| 2004/0181149 | A1 | 9/2004 | Langlotz et al. | |
| 2005/0047676 | A1 | 3/2005 | Kang et al. | |
| 2005/0085720 | A1 | 4/2005 | Jascob | |
| 2005/0089199 | A1 | 4/2005 | Marschner et al. | |
| 2005/0270375 | A1 | 12/2005 | Poulin | |
| 2005/0280709 | A1 | 12/2005 | Katayama | |
| 2005/0281465 | A1 | 12/2005 | Marquart et al. | |
| 2006/0082546 | A1 | 4/2006 | Wey | |
| 2006/0239345 | A1 | 10/2006 | Taubman et al. | |
| 2008/0075324 | A1 | 3/2008 | Sato | |
| 2008/0097156 | A1 | 4/2008 | Nakamura | |
| 2008/0202509 | A1 | 8/2008 | Dillon et al. | |
| 2008/0239327 | A1 | 10/2008 | Bryll | |
| 2008/0269596 | A1 * | 10/2008 | Revie | G06Q 10/087 600/424 |
| 2008/0306490 | A1 | 12/2008 | Lakin et al. | |
| 2010/0009314 | A1 * | 1/2010 | Tardieu | A61C 1/084 433/144 |
| 2010/0039506 | A1 * | 2/2010 | Sarvestani | A61B 90/361 348/65 |
| 2010/0245541 | A1 | 9/2010 | Zhao | |
| 2010/0256504 | A1 * | 10/2010 | Moreau-Gaudry | A61B 5/0066 600/476 |
| 2011/0075922 | A1 | 3/2011 | Turner et al. | |
| 2011/0115798 | A1 | 5/2011 | Nayar et al. | |
| 2011/0130761 | A1 * | 6/2011 | Plaskos | A61B 17/155 606/87 |
| 2012/0078049 | A1 | 3/2012 | Pauli et al. | |
| 2012/0120255 | A1 | 5/2012 | Cao et al. | |
| 2013/0034203 | A1 | 2/2013 | Wang et al. | |
| 2013/0123801 | A1 | 5/2013 | Umasuthan et al. | |
| 2013/0150863 | A1 | 6/2013 | Baumgartner | |
| 2013/0281821 | A1 * | 10/2013 | Liu | A61B 1/00 600/409 |
| 2014/0022248 | A1 | 1/2014 | Kuffner, Jr. et al. | |
| 2014/0031668 | A1 | 1/2014 | Mobasser et al. | |
| 2014/0035893 | A1 | 2/2014 | Jackson et al. | |
| 2014/0107471 | A1 | 4/2014 | Haider et al. | |
| 2014/0236159 | A1 * | 8/2014 | Haider | A61B 17/1626 606/88 |
| 2014/0285676 | A1 * | 9/2014 | Barreto | H04N 17/002 348/187 |
| 2014/0327796 | A1 | 11/2014 | Lin et al. | |
| 2015/0065799 | A1 | 3/2015 | Hale et al. | |
| 2015/0254872 | A1 | 9/2015 | Barreto et al. | |
| 2015/0297177 | A1 * | 10/2015 | Boctor | A61B 8/4218 600/437 |
| 2016/0000518 | A1 * | 1/2016 | Thoranaghatte | G06F 3/017 703/11 |
| 2016/0148435 | A1 | 5/2016 | Li et al. | |
| 2016/0161602 | A1 | 6/2016 | Prokhorov | |
| 2016/0183841 | A1 | 6/2016 | Duindam et al. | |
| 2016/0191887 | A1 | 6/2016 | Casas | |
| 2016/0220099 | A1 | 8/2016 | Schouwink et al. | |
| 2016/0324580 | A1 | 11/2016 | Esterberg | |
| 2017/0325669 | A1 | 11/2017 | Levy | |

(56) References Cited

U.S. PATENT DOCUMENTS

| | | | |
|---|---|---|---|
| 2018/0049622 A1 | 2/2018 | Ryan et al. | |
| 2018/0089855 A1 | 3/2018 | Rodrigues et al. | |

FOREIGN PATENT DOCUMENTS

| | | | | |
|---|---|---|---|---|
| EP | 3130276 A1 | | 2/2017 | |
| WO | WO-2009042644 | * | 4/2009 | ..... A61B 5/0066 |
| WO | 2013015699 A1 | | 1/2013 | |
| WO | WO-2013052187 A2 | * | 4/2013 | ..... A61N 17/1626 |
| WO | 2014054958 A2 | | 4/2014 | |
| WO | WO-2014122301 A1 | * | 8/2014 | ..... G06F 3/017 |
| WO | 2016154557 A1 | | 9/2016 | |
| WO | 2016168307 A1 | | 10/2016 | |

OTHER PUBLICATIONS

Mitra, Niloy J., et al., "Registration of Point Cloud Data from a Geometric Optimization Perspective", Eurographics Symposium on Geometry Processing, pp. 23-32, 2004.

Jalobeanu et al. "Modeling Images of Natural 30 Surfaces: Overview and Potential Applications"; IEEE; Publication [online]. Jun. 2004. [retrieved Jun. 24, 2016]. Retrieved from the Internet: <URL: http://citeseerx.ist.psu.edu/vlewdoc/download?doi=10.1.1.59.1141 &rep=rep1 &type=pdf>; pp. 1-9.

Kim, Dong Sik et al.; "Joint Optimization of Spatial Registration and Histogram Compensation for Microscopic Images"; Conference Proceedings: Annual International Conference of the IEEE Engineering in Medicine and Biology Society; pp. 3779-3782; Aug. 30, 2006.

Fitzgibbon, A.W.; "Simultaneous Linear Estimation of Multiple View Geometry and Lens Distortion;" Proceedings of the 2001 IEEE Computer Society Conference on Computer Vision and Pattern Recognition; CVPR 2001, vol. 1, pp. 1-8, Jan. 1, 2001.

Song, KS et al. "Region Adaptive Correction Method for Radial Distortion of Fish-Eye Image;" Image Processing: Algorithms and Systems X; and Parallel Processing for Imaging Applications II, SPIE, vol. 8295, No. 1., pp. 1-7, Feb. 9, 2012.

Kim, Seon Joo et al.; "Joint Feature Tracking and Radiometric Calibration from Auto-Exposure Video"; Computer Vision, 2007, pp. 1-8, Oct. 1, 2007.

Carr, Peter et al.; "Point-less Calibration: Camera Parameters from Gradient-Based Alignment to Edge Images"; Applications of Computer Vision (WACV), pp. 377-384, Jan. 9, 2012.

PCT International Search Report in International Application No. PCT/PT2016/024262 dated Jun. 24, 2016.

Bruce D. Lucas and Takeo Kanade. An Iterative Image Registration Technique with an Application to Stereo Vision; In DARPA Image Understanding Workshop, pp. 121-130, Apr. 1981.

Simon Baker and Iain Matthews. Equivalence and Efficiency of Image Alignment Algorithms. In IEEE Conf. Vis. Patt. Recogn., vol. 1, pp. 1090-1097, Dec. 2001.

Simon Baker and Iain Matthews. Lucas-kanade 20 years on: A unifying framework. Int. J. Comput. Vis., 56(3):221-255, Mar. 2004.

Jianbo Shi and C. Tomasi. Good features to track. In IEEE Conf. Vis. Patt. Recogn., pp. 593 600, Jun. 1994.

Myung Hwangbo, Jun-Sik Kim, and Takeo Kanade. Gyro-aided feature tracking for a moving camera: fusion, auto-calibration and GPU implementation. Int. J. of Robot. Res., 30(14):1755-1774, Dec. 2011.

Jean-Yves Bouguet. Pyramidal Implementation of the Lucas Kanade Feature Tracker Description of the algorithm, 2000.

L. Matthews, T. Ishikawa, and S. Baker. The Template Update Problem. IEEE Trans. Pall. Anal. Mach. Intell., 26(6):810-815, Jun. 2004.

Reg G. Willson and Steven A. Shafer. What is the center of the image? J. Opt. Soc. Am. A, 11(11):2946-2955, Apr. 1993.

Joao P. Barreto. A Unifying Geometric Representation for Central Projection Systems. Comput. Vis. Imag. Unders., 103(3):208-217, Jun. 2006.

Joao P. Barreto, Jose Roquette, Peter Sturm, and Fernando Fonseca. Automatic Camera Calibration Applied to Medical Endoscopy. In Brit. Mach. Vis. Conf., Sep. 2009.

M. Menem, "Constraints on perspective images and circular panoramas," BMVC, Sep. 2004.

D. Claus and A. Fitzgibbon, "A Rational Function lens distortion model for general cameras," Computer Vision and Pattern Recognition IEEE Computer Society Conference on , pp. 213-219, vol. 1, Jun. 2005.

Bill Triggs, Philip F. McLauchlan, Richard I. Hartley, and Andrew W. Fitzgibbon. Bundle adjustment—a modern synthesis. In Proceedings of the International Workshop on Vision Algorithms: Theory and Practice, ICCV '99, pp. 298-372, London, UK, Springer-Verlag, 2000.

Greg Welch and Gary Bishop. An Introduction to the Kalman Filter. Technical report, University of North Carolina at Chapel Hill, Chapel Hill, N.C., USA, 1995; updated Jul. 2006.

Simon Baker, Daniel Scharstein, J. P. Lewis, Stefan Roth, Michael J. Black, and Richard Szeliski. A database and evaluation methodology for optical flow. Int. J. Comput. Vision, 92(1), Dec. 2011.

Steffen Gauglitz, Tobias Hollerer, and Matthew Turk. Evaluation of Interest Point Detectors and Feature Descriptors for Visual Tracking. Int. J. Comput. Vis., 94(3):335-360, Mar. 2011.

K. Daniilidis, A. Makadia, and T. Bulow. Image Processing in Catadiop-tric Planes: Spaciotemporal Derivatives and Optical Flow Computation. In Int. Workshop on Omndirectional Vision, Jun. 2002.

M. Lourenco, J. P. Barreto, and F. Vasconcelos. sRD-SIFT: Keypoint Detection and Matching in Images With Radial Distortion. IEEE Trans Robotics, Jun. 2012.

P. Sturm, S. Ramalingam, J.-P. Tardif, S. Gasparini and J. Barreto, Camera Models and Fundamental Concepts Used in Geometric Computer Vision. Now Publishers, Inc., Jan. 2011.

David Nistér. An Efficient Solution to the Five-Point Relative Pose Problem. IEEE Trans. Pati Anal. Mach. Intell., Jun. 26, 2004.

R. Melo, J.P. Barreto, and G. Falcao. A new solution for camera calibration and real-time image distortion correction in medical endoscopy—initial technical evaluation. Biomedical Engineering, IEEE Transactions on, 59(3):634-644, Mar. 2012.

Alper Yilmaz, Omar Javed, and Mubarak Shah. Object Tracking: A survey. ACM Comput. Surv., 38, Dec. 2006.

Marc Pollefeys, Luc Van Gool, Maarten Vergauwen, Frank Verbiest, Kurt Cornelis, Jan Tops, and Reinhard Koch. Visual Modeling with a Hand-Held Camera. Int. J. Comput. Vis., 59(3):207-232, Sep. 2004.

P. Baker, C. Fermuller, Y. Aloimonos, and R. Pless. A Spherical Eye from Multiple Cameras (Makes Better Models of the World). In IEEE Conf. Vis. Patt. Recogn., Feb. 2001.

Peter Hansen, Peter Corke, and Wageeh Boles. Wide-Angle Visual Feature Matching for Outdoor Localization. Int. J. of Robot. Res., 29:267-297, Feb. 2010.

Darius Burschka, Ming Li, Russell H. Taylor, and Gregory D. Hager. Scale-Invariant Registration of Monocular Endoscopic Images to CT-Scans for Sinus Surgery. In Med. Image Comput. and Computer-Assist. Inter., Sep. 2004.

Alexander Behrens, Michael Bommes, Thomas Stehle, Sebastian Gross, Steffen Leonhardt, and Til Aach. Real-time image composition of bladder mosaics in fluorescence endoscopy. Computer Science—Research and Development, 26:51-64, Feb. 2011.

Kevin Koeser, Bogumil Bartczak, and Reinhard Koch. Robust GPU-assisted camera tracking using free-form surface models. Journal of Real-Time Image Processing, 2(2):133-147, Oct. 2007.

T. Brox and J. Malik. Large displacement optical flow: descriptor matching in variational motion estimation. IEEE Trans. Patt. Anal. Mach. Intell., 33(3):500-513, Mar. 2011.

Miguel Lourenco and Joao P. Barreto. Tracking features in uncalibrated images with radial distortion. In Eur. Conf. Comput. Vis., pp. 1-14, Oct. 2012.

(56) References Cited

OTHER PUBLICATIONS

C. Mei, S. Benhimane, E. Malis, and P. Rives. Efficient Homography-based Tracking and 3D Reconstruction for Single Viewpoint Sensors. IEEE Trans Robotics, Dec. 2008.
A. Rav-Acha and S. Peleg. Lucas-Kanade without Iterative Warping. In IEEE Int. Conf. Image Process., pp. 1097-1100, Oct. 2006.
C. Mei, S. Benhimane, E. Malis, and P. Rives. Constrained multiple planar template tracking for central catadioptric cameras. In British Machine Vision Conference, Sep. 2006.
A. Salazar-Garibay, E. Malis, and C. Mei. Visual tracking of planes with an uncalibrated central catadioptric camera. In IROS, Mar. 2009.
Toru Tamaki, Tsuyoshi Yamamura, and Noboru Ohnishi. Unified approach to image distortion. In ICPR, pp. 584-587, Aug. 2002.
Y. Chang, "Multi-view 3D Reconstruction for Scenes Under the Refractive plane with known vertical direction," Computer Vision (ICCV), Nov. 2011.
T. Yamaguchi, M. Nakamoto, Y. Sato, Y. Nakajima, K. Konishi, M. Hashizume, T. Nishii, N. Sugano, H. Yoshikawa, K. Yonenobu, and S. Tamura, "Camera Model and Calibration Procedure for Oblique-Viewing Endoscope," in MICCAI, pp. 373-381, Nov. 2003.
C. Wu, B. Jaramaz, and S. G. Narasimhan, "A Full Geometric and Photometric Calibration Method for Oblique-viewing Endoscope," International Journal of Computer Aided Surgery, vol. 15, pp. 19-31, Apr. 2010.
N. Fukuda, Y. Chen, M. Nakamoto, and T, "A scope cylinder rotation tracking method for oblique-viewing endoscopes without attached sensing device," Software Engineering and Data Mining, No. 1, pp. 684-687, Jun. 2010.
J. Barreto, J. Santos, P. Menezes, and F. Fonseca, "Ray-based Calibration of Rigid Medical Endoscopes," in OMNIVIS, Sep. 2008.
B. Chapman, G. Jost, and R. Van Der Pass, Using OpenMP: Portable Shared Memory Parallel Programming Scientific Computation and Engineering Series). The MIT Press, 2008.
M. A. Fischler and R. C. Bolles, "Random Sample Consensus: A Paradigm for Model Fitting with Applications to Image Analysis and Automated Cartography," Commun. ACM, vol. 24, No. 6, pp. 381-395, Jun. 1981.
A. Agrawal, Y. Taguchi, and S. Ramalingam, "Analytical forward projection for axial non-central diotropic and catadioptric cameras," presented at the ECCV'10: Proceedings of the 11th European Conference on Computer Vision: Part III, Sep. 2010.
N. Smith, N. Vakil, and S. Maislin, "Correction of Distortion in Endoscope Images," IEEE Transactions on Medical Imaging, vol. 11, No. 1, pp. 117-122, Mar. 1992.
K. Vijayan-Asari, S. Kumar, and D. Radhakrishnan, "A new approach for nonlinear distortion correction in endoscopic images based on least squares estimation," IEEE Transactions on Medical Imaging, vol. 18, No. 4, pp. 345-354, Apr. 1999.
J. Helferty, C. Zhang, G. McLennan, and W Higgins, "Videoendoscopic distortion correction and its application to virtual guidance of endoscopy," IEEE Transactions on Medical Imaging, vol. 20, No. 7, pp. 605-617, Jul. 2001.
Kalman, R.E.; A New Approach to Linear Filtering and Prediction Problems; ASME—Journal of Basic Engineering, 82 (Series D): 35-45; Mar. 1960.
T. Stehle, M. Hennes, S. Gross, A. Behrens, J. Wulff, and T. Aach, "Dynamic Distortion Correction for Endoscopy Systems with Exchangeable Optics," in Bildverarbeitungfür die Medizin 2009. Berlin: Springer, pp. 142-146, 2009.
J.-Y. Bouguet. Camera Calibration Toolbox for Matlab. [Online]. Available: http://www.vision.caltech.edu/bouguetj/calibdoc/index.html#ref; Last Updated Oct. 14, 2015.
Z. Zhang, "Flexible camera calibration by viewing a plane from unknown orientations," in ICCV, pp. 666-673, Sep. 1999.
R. Shahidi, M. Bax, C. Maurer, J. Johnson, E. Wilkinson, B. Wang, J. West, M. Citardi, K. Manwaring, and R. Khadem, "Implementation, calibration and accuracy testing of an image-enhanced endoscopy system," IEEE Transactions on Medical Imaging, vol. 21, No. 12, pp. 1524-1535, Dec. 2002.
C. Wengert, M. Reef f, P. Cattin, and G. Siekely, "Fully automatic endoscope calibration for intraoperative use," in Bildverarbeitungfür die Medizin 2006, pp. 419-423, Mar. 2006.
J. Mallon and P. F. Whelan, "Which pattern? Biasing aspects of planar calibration patterns and detection methods," Pattern Recognition Letters, vol. 28, No. 8, pp. 921-930, Jan. 2007.
S. D. Buck, F. Maes, A. D'Hoore, and P. Suetens, "Evaluation of a novel calibration technique for optically tracked oblique laparoscopes," Proceedings of the 10th international conference on Medical image computing and computer-assisted intervention—vol. Part I, pp. 467-474, Feb. 2007.
A. Fitzgibbon, M. Pilu, and R. Fisher, "Direct least square fitting of ellipses," IEEE Transactions on Pattern Analysis and Machine Intelligence, vol. 21, No. 5, pp. 476-480, May 1999.
Chen, X. et al., "A Theoretical Analysis of Camera Response Functions in Image Deblurring" European Conference on Computer Vision, 2012.
Fu, L. et al., "Camera Response Function Estimation and Application with a Single Image" Informatics in Control, Automation and Robotics, vol. 2, LNEE 133, pp. 149-156, 2011.
Harney, L. "Simultaneous Estimation of Camera Response Function, Target Reflectance and Irradiance Values" Department of Computing, Macquarie University, Australia, Conference Dec. 6-8, 2005, Digital Image Computing: Techniques and Applications 2005.
Lin, S. et al., "Radiometric Calibration from a Single Image" Proceedings of the 2004 IEEE Computer Society Conference on Computer Vision and Pattern Recognition, 2004.
Ng, T. et al., "Using Geometry Invariants for Camera Response Function Estimation" IEEE Conference on Computer Vision and Pattern Recognition Jun. 17-22, CVPR 2007.
Qiu, S. et al., "Estimation Method of CCD and CMOS Response Functions Based on a Single Image" International Conference on Optical Instruments and Technology: Optoelectronic Imaging and Process Technology, Proc. SPIE, 751325, Nov. 24, 2009.
Yu, W. "Practical Anti-Vignetting Methods for Digital Cameras" IEEE Transactions on Consumer Electronics, vol. 50, Issue 4, pp. 975-983, Nov. 2004.
Zheng, Y. et al., "Single-Image Vignetting Correction" IEEE Transactions on Pattern Analysis and Machine Intelligence, vol. 31, Issue 12, pp. 2243-2256, Oct. 31, 2008.
Supplementary European Search Report based on EP 16769785 dated Oct. 26, 2018. USPTO Office Action in U.S. Appl. No. 15/566,536 dated Apr. 4, 2019.

* cited by examiner $$P_T = \hat{T}^{-1} . \hat{G} . P_G$$

METHODS AND SYSTEMS FOR COMPUTER-AIDED SURGERY USING INTRA-OPERATIVE VIDEO ACQUIRED BY A FREE MOVING CAMERA

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE AND CLAIM OF PRIORITY TO RELATED APPLICATIONS

This patent application *reissue continuation of U.S. patent application Ser. No. 17/548,202, filed Dec. 10, 2021, which is an application for reissue of U.S. Pat. No. 10,499,996, issued Dec. 10, 2019, which is a* is a U.S. national phase application of PCT International Patent Application No. PCT/US2016/024262, filed on Mar. 25, 2016, which claims the benefit of U.S. Provisional Patent Application Ser. No. 62/138,529, filed on Mar. 26, 2015 and titled "Methods and Systems for Computer-Aided Navigation in Surgical Procedures", and U.S. Provisional Patent Application Ser. No. 62/255,513, filed on Nov. 15, 2015 and titled "Methods and Systems for Computer-Aided Navigation in Surgical Procedures", all of which are hereby incorporated by reference in their entireties*; more than one reissue application has been filed for the reissue of U.S. Pat. No. 10,499,966; the reissue applications are the present application and application Ser. No. 17/548,202. This application is both a continuation of Reissue application Ser. No. 17/548,202 and a reissue of U.S. Pat. No. 10,499,996.*

STATEMENT REGARDING FEDERALLY SPONSORED RESEARCH OR DEVELOPMENT

Not applicable.

FIELD

The disclosure generally relates to the field of computer-aided surgery, and in particular, but not by way of limitation, the disclosed embodiments refer to computer aided-navigation in camera guided procedures of surgery and diagnosis in anatomical regions with rigid tissues such as bone, which includes arthroscopy of knee, hip, or shoulder, and open surgery in orthopedics and dentistry in which case a camera must be used to observe the operating field. One or more embodiments can also be employed in any other application domain, such as industrial inspection, that uses a camera system to visualize a work space that comprises rigid, non-deformable parts.

BACKGROUND

Minimally Invasive Surgical (MIS) procedures aim to minimize damage to healthy tissue by accessing targeted organs and anatomical cavities through relatively small size incisions. Since the workspace is not fully exposed, the surgeon typically carries the medical procedure using as guidance video acquired by a camera system that is inserted into the cavity. MIS procedures are being increasingly adopted in different medical specialties, such as orthopedics, abdominal surgery, urology, neurosurgery, and ENT, just to name a few.

Arthroscopy is a MIS procedure for treatment of damaged joints in which instruments and endoscopic camera (the arthroscope) are inserted into the articular cavity through small incisions (the surgical ports). Arthroscopy, as opposed to conventional open surgery, largely preserves the integrity of the articulation, which is beneficial for the patient in terms of reduction of trauma, risk of infection and recovery time. Unfortunately, arthroscopic procedures are relatively difficult to execute because of indirect visualization and limited maneuverability inside the joint, with novices having to undergo a long training period and experts often making mistakes of clinical consequences. This is a scenario where computer-assistive technologies for safely guiding the surgeon throughout the procedure can make a difference, both in terms of improving clinical outcome and in terms of decreasing the surgeon learning curve.

Depending on the particular clinical application, a system for Computer-Aided Surgery (CAS) comprises two distinct stages: (i) an offline step in which the procedure is planned leading to some sort of computational model that can either be a three-dimensional (3D) pre-operative image of the patient's organ (e.g. CT-Scan), a statistical bone model, or a set of guidelines for inferring meaningful locations with respect to anatomical landmarks; and (ii) an intra-operative navigation step in which the computer guides the surgeon throughout the procedure for the execution to be done as defined.

The intra-operative navigation usually passes by overlying the pre-operative computational model with the actual bone, and by localizing in real-time the tools and instruments with respect to each other, and with respect to the targeted organ. Typically, the technology to accomplish this task is Optical-Tracking (OT) that consists in using a stationary stereo head, henceforth called base station, for tracking a set of markers that are rigidly attached to instruments and/or bone. The stereo head comprises two infrared (IR) cameras that track a set of point markers that are rigidly attached to the object of interest. The position of each marker is estimated by simple triangulation and, since their relative arrangement is known 'a priori', the 3D pose of the object of interest is computed in the reference frame of the base station. Recently, a technological variant of OT was introduced in which the two IR cameras are replaced by two conventional video cameras operating in the visible spectrum, and the arrangements of IR markers are replaced by planar markers with printed known patterns.

The surgical navigation solutions that are currently available for Orthopedics, Neurosurgery, and ENT invariably rely in OT. In generic terms, the typical workflow passes by the surgeon to rigidly attach a tool marker to patient and/or targeted organ, which is followed by pin pointing anatomical landmarks with a calibrated tracked probe. The 3D position of these landmarks is determined in the coordinate system of the base station and the pre-operative computational model is registered with the patient. From this point on, it is possible to determine in real-time the pose of instruments with respect to patient and plan, which enables the system to safely guide the surgeon throughout the procedure. There are some variants to this scheme that mainly address the difficulties in performing the 3D registration of patient's anatomy with a pre-operative model with a tracked probe that tends to be an error prone, time consuming process. For example, the O-arm from Medtronic® combines OT with a CT-scanner that enables the acquiring of the 3D pre-operative model of patient's anatomy in the Operating Room (OR) before starting the procedure, which avoids the surgeon performing explicit registration. The system that is being developed by 7D Surgical® goes in the same direction with the 3D model being obtained using multi-view reconstruction and structured light to avoid the ionizing radiation of CT-scanning. Nevertheless, these systems still rely in conventional OT to know the relative position between instruments and anatomy after registration has been accomplished.

OT has proved to be an effective way of obtaining real-time 3D information in the OR, which largely explains the fact of being transversally used across different systems and solutions. However, the technology has several drawbacks that preclude a broader dissemination of surgical navigation: (i) it requires a significant investment in capital equipment, namely in acquiring the base station; (ii) it disrupts normal surgical workflow by changing the OR layout to accommodate additional equipment, by forcing the surgeon to work with instruments with bulky tool markers attached, and by constraining the team movements due to the need of preserving lines of sight between base station and tool markers; and (iii) it is not well suited to be used in MIS procedures because organs and tissues are occluded which avoids placing marker tools that can be observed from the outside by the base station. For example, OT based navigation in arthroscopic procedures always requires opening additional incisions such that the marker tool attached to the bone protrudes through patient skin.

In recent years some alternative technologies have emerged in an attempt of obviating the above-mentioned drawbacks. Electromagnetic Tracking (ET) is currently used in some surgical navigation systems with the advantage of not requiring preservation of a line of sight. However, it has the problem of being vulnerable to electromagnetic interference caused by nearby metals and devices, being in practice less reliable and accurate than OT. Moreover, it still requires additional capital equipment, namely a base station, and the need of attaching coil markers with hanging wires to organs makes it non amenable to MIS procedures.

SUMMARY

The embodiments in the disclosure provide a new concept for computer-assisted procedures of surgery and diagnosis that target rigid, non-deformable anatomical parts such as bone, tissue, or teeth. The disclosure describes attaching small visual markers to instruments and anatomy of interest (e.g. bone surface), with each marker having a printed known pattern for detection and unique identification in images acquired by a free-moving camera, and a geometry that enables estimating its rotation and translation with respect to the camera using solely image processing techniques.

The concept, henceforth referred as Visual-Tracking Inside the Anatomical Cavity (VTIAC), introduces three main differences from other embodiments of OT/ET in the context of computer-aided surgery: First, the global world reference frame, instead of being the coordinate frame of the external base station, it is the system of coordinates of a marker that is rigidly attached to the anatomy of interest (e.g. bone surface). This marker, referred to herein as World Marker or WM, serves as absolute reference such that all measurements are expressed in its coordinates (world coordinates); Second, the free-moving camera acts as the single sensing modality with all measurements and real-time 3D inferences being carried by processing the acquired video. This feature avoids significant investments in additional capital equipment when compared with OT/ET; and Third, since measurements are performed in high resolution images acquired at close range, the metric accuracy of VTIAC is significantly better than the one accomplished with OT/ET.

The disclosure discloses the apparatus for VTIAC and the required initial calibration procedures, it describes how to use VTIAC to perform very accurate 3D measurements inside the anatomical cavity, and it shows how to use augmented reality, virtual reality, or robotics to provide real-time guidance to the surgeon after registering a pre-operative 3D plan.

In terms of clinical applications VTIAC is specially well suited for arthroscopy where the already existing monocular arthroscope acts as the free-moving camera that provides the video input. VTIAC can be successfully employed in any clinical procedure that targets anatomical regions with rigid parts, such as open orthopaedic surgery or dentistry, in which case the operating field must be observed by a camera that can either be attached to a tool or handheld. The disclosure describes illustrative implementations in knee arthroscopy and spine surgery that by no means limit the range of possible clinical applications.

BRIEF DESCRIPTION OF THE DRAWING

For a more complete understanding of the present disclosure, reference is made to the following detailed description of exemplary embodiments considered in conjunction with the accompanying drawings.

In VR view, the optical axis of the virtual camera is aligned with the desired line of perforation or insertion. The penetration depth displayed is relative to the bone surface at the entry point.

Figure 7A:
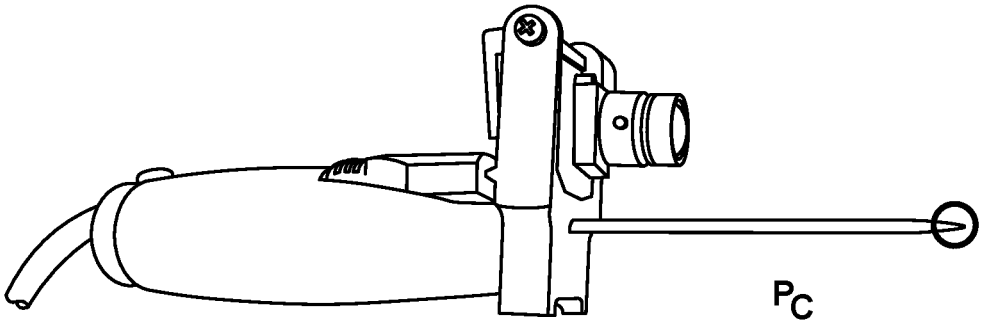

FIG. 7A is a prototype of the embodiment of a Camera Tool (CamT) including a small-camera mounted on a custom made hand-holder that can either be used as a free-hand camera, or coupled with touch-probe such that camera, holder, and probe become a single rigid body. $P_C$ is the tool tip that can be calibrated with respect to the camera.

Figure 7B:
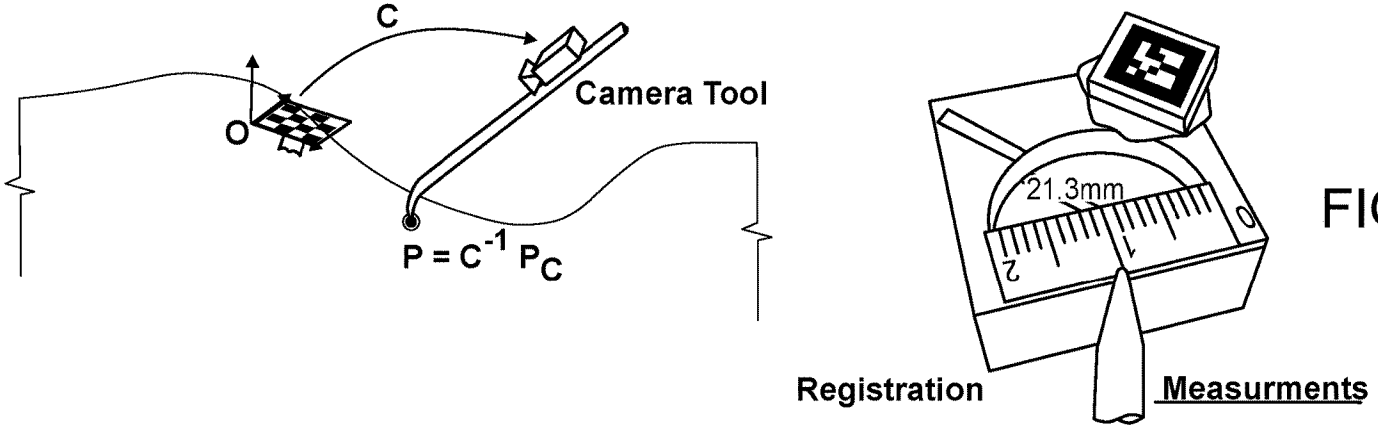

FIG. 7B is an embodiment of using the CamT to reconstruct points in the bone surface. The 3D coordinates $P_C$ of the tip of the probe are known in the camera reference frame and therefore they can be referenced to the WM for measurements computation, as if it was a tool with a TM.

Figure 7C:
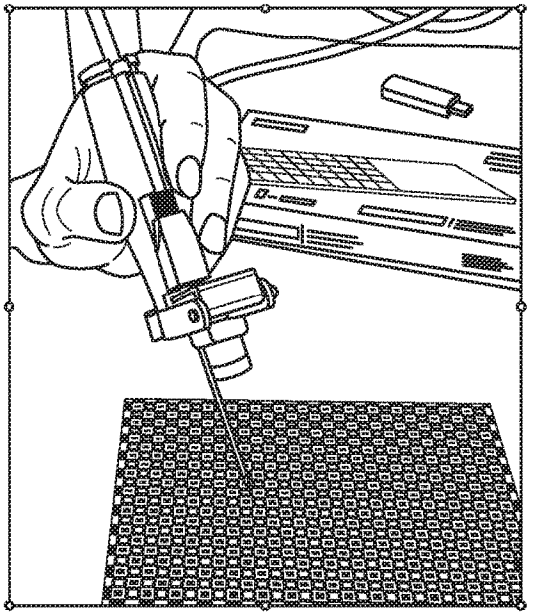

FIG. 7C is an embodiment of a representation of the CamT calibration using a single image of the calibration pattern to simultaneously calibrate the camera and the tool tip position $P_G$. When the tool is touching the calibration pattern at a point of known coordinates $P_G$, the transform $P_C$ between the tool point of contact with $P_G$ and the camera reference frame is given by $P_C = G \cdot P_G$.

Figure 7D:
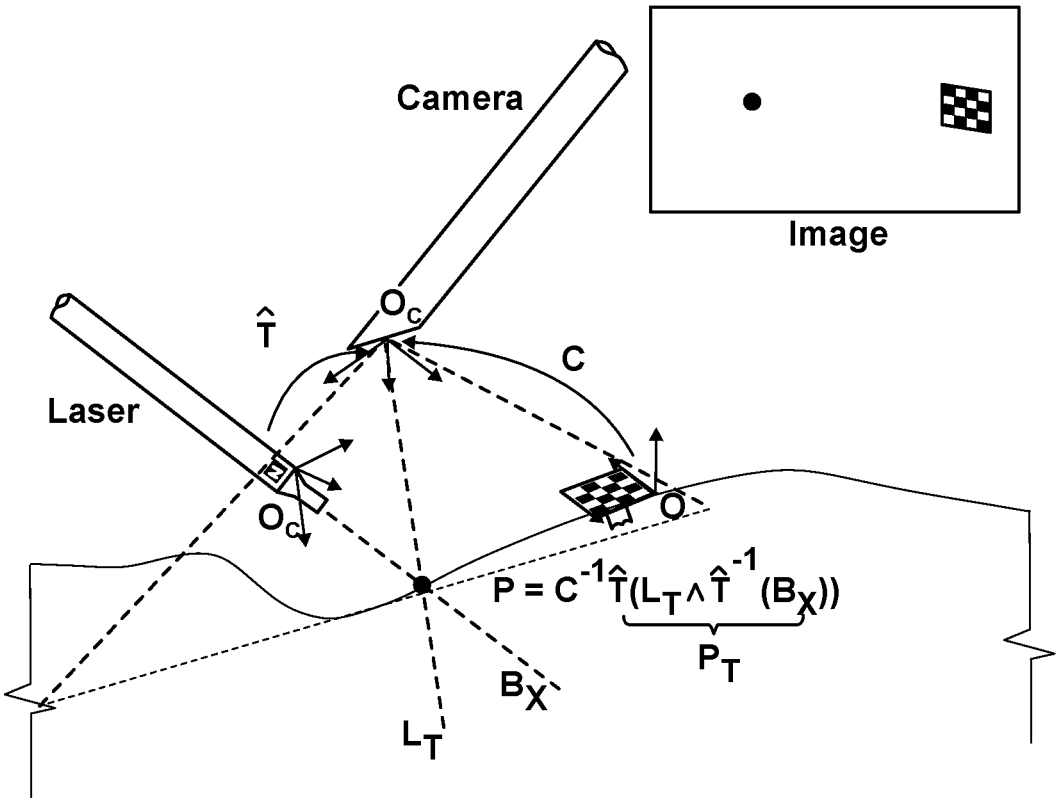

FIG. 7D is an embodiment of a representation of using the VTIAC with a laser pointer instead of a touch probe for contactless measurements. The lases pointer is instrumented with a TM that is in the FOV of the camera. The laser pointer produces a colored dot on the bone/tissue surface (point of incidence), that is seen in the image (as well as the TM and WM). The point is reconstructed in 3D by intersecting the line $L_T$ of the beam with the back-projection line $B_x$ of the image point x where the point of light incidence is projected.

Figure 7E:
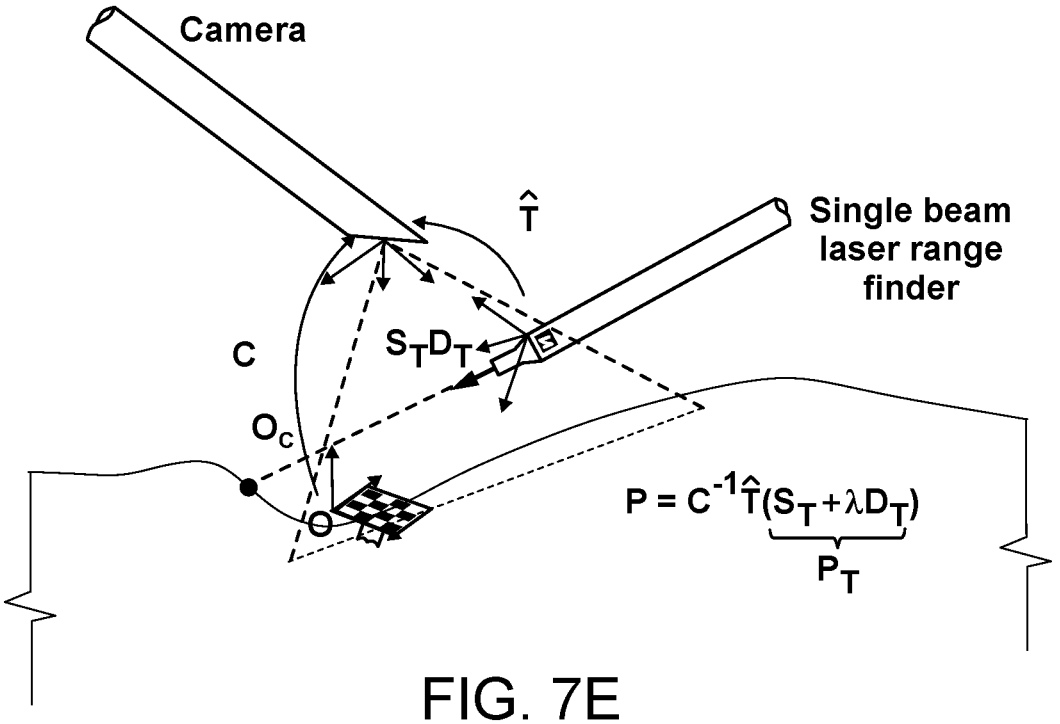

FIG. 7E is an embodiment of a representation of using the VTIAC with a Laser Rangefinder (LRF), or other equivalent device or technology relying in Time-of-Flight (ToF) principles, that is able to measure distances along the direction of the beam line $L_T$. The origin and unit direction of measurement, $S_T$ and $d_T$, are known in the local reference frame of TM. For 3D reconstruction the surgeon orients the LRF such that the beam becomes incident with the point of interest in the anatomy, and acquires in a synchronous manner the distance measurement $\lambda$ and an image where both WM and TM are visible. The point of interest can be outside the camera FOV.

Figure 7F:
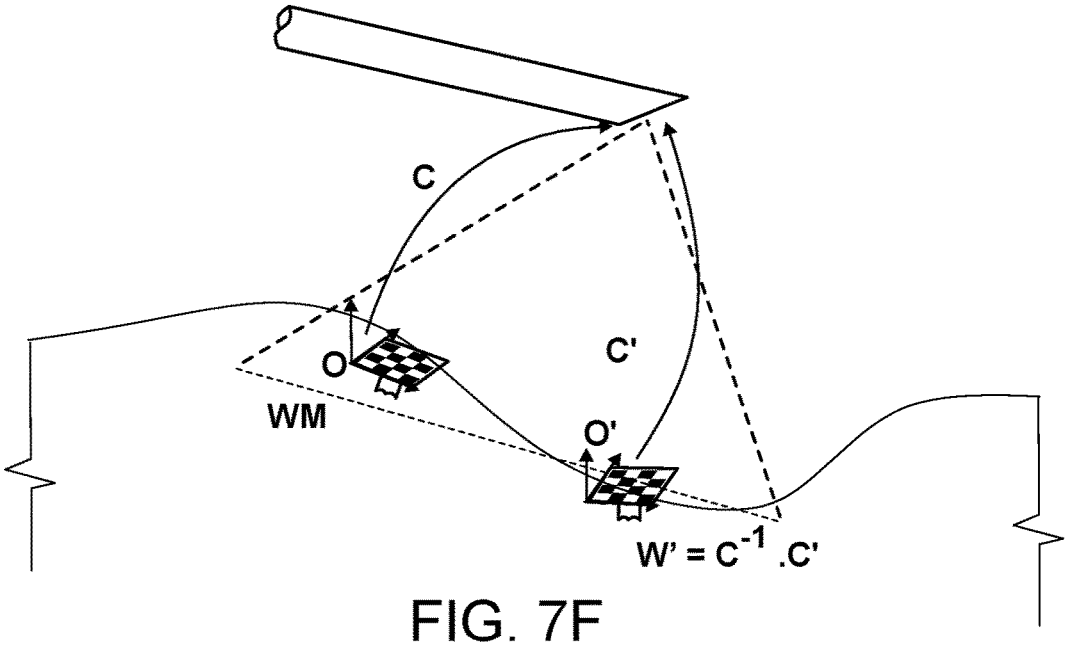

FIG. 7F is an embodiment of a representation of the use of multiple WM to increase the area of operation. The surgeon can fix an auxiliary visual marker (WM') on a convenient location on the bone surface, and move the camera such that both WM and WM' lie in the FOV. This enables registration of the auxiliary marker in the WM reference frame by making $W' = C^{-1} C'$ with C and C' being the poses of WM and WM' in camera coordinates. From this point on it is sufficient for the camera to see one of the markers in order to be registered in the global reference frame.

Figure 7G:
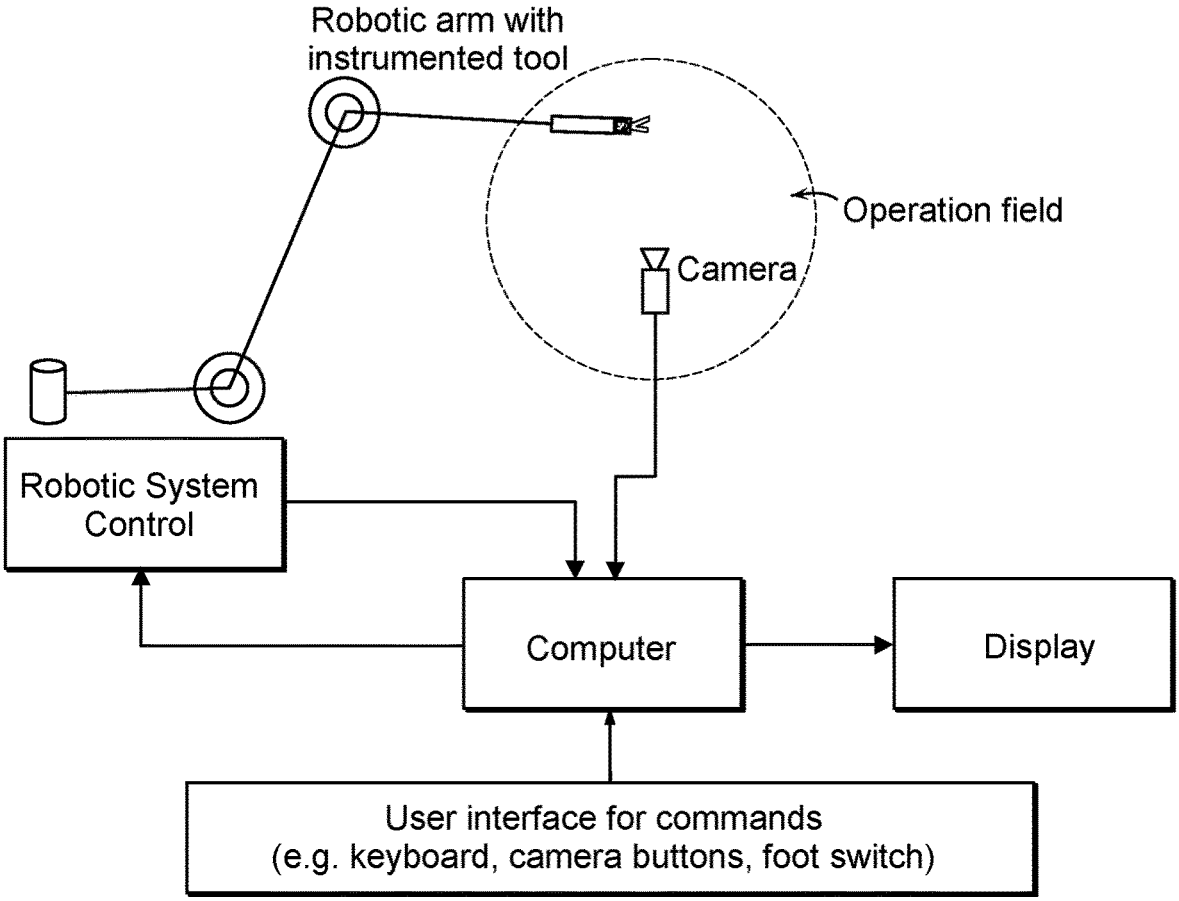

FIG. 7G is an embodiment of a representation of using the VTIAC to provide control commands to a robotic system. The robotic end effector is instrumented with a TM and the anatomy has a WM attached such that relative 3D pose can be computed from video acquired by the free-moving camera. The VTIAC uses the visual feedback to guide the positioning of the end-effector by sending commands to the robot. The robotic arm can also provide feedback of the actuators state that can be fused with visual feedback for more accurate closed loop control.

Figure 8:
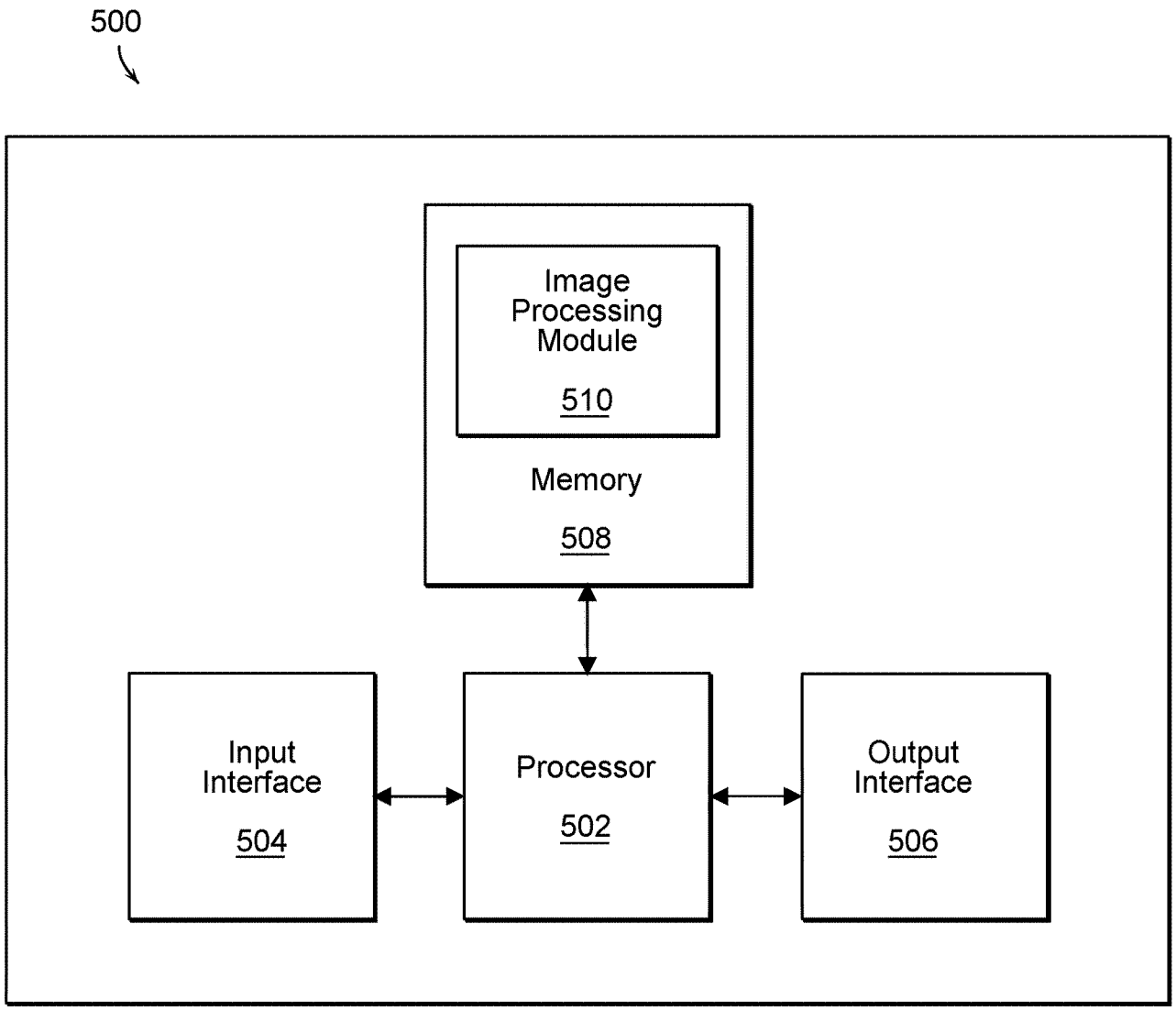

FIG. 8 is a schematic diagram of an embodiment of an image processing system.

Figure 9:
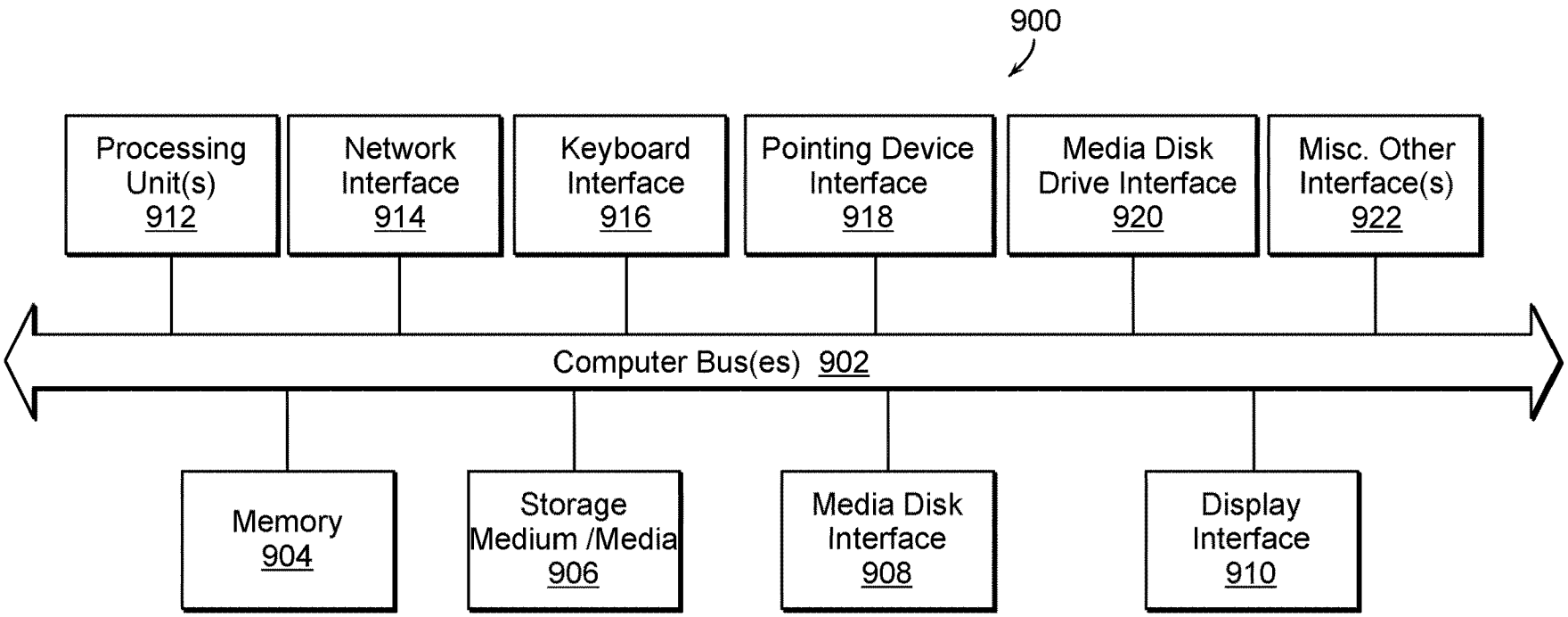

FIG. 9 is a schematic diagram of an embodiment of a computing device.

DETAILED DESCRIPTION

1. Introduction

It should be understood that, although an illustrative implementation of one or more embodiments are provided below, the various specific embodiments may be implemented using any number of techniques known by persons of ordinary skill in the art. The disclosure should in no way be limited to the illustrative embodiments, drawings, and/or techniques illustrated below, including the exemplary designs and implementations illustrated and described herein.

One or more embodiments disclosed herein applies to camera-guided orthopedic MIS procedures, namely arthroscopy, that is used as illustrative example throughout most of the description. However, the application of the presently disclosed embodiments can include other surgical procedures and clinical specialties where the operating field comprises rigid, non-deformable parts and surfaces. The application of the disclosed embodiments requires a camera system for visualizing the anatomical scene that might already exist (e.g. arthroscopy) or be added (e.g. open orthopedic surgery).

One or more embodiments in the disclosure provide a surgical navigation scheme for arthroscopy and other procedures using a conventional camera and with scenes that comprise rigid surfaces. The surgical navigation scheme will be referred to as Visual-Tracking Inside the Anatomical Cavity (VTIAC). The disclosure relates to attaching small, recognizable visual markers to instruments and rigid anatomy (e.g. bones) and use the free-moving camera, that is the arthroscope in case of arthroscopic procedures, to estimate their relative rotation and translation (the relative 3D pose). For the case of the markers being planar with a printed known pattern, the relative 3D pose is determined by estimating the plane-to-image homography that is factorized to obtain the rotation and translation between plane and camera reference frames. The marker attached to the bone surface, referred to herein as World Marker (WM), serves as absolute reference with all measurements being expressed in its coordinate system (world coordinates). VTIAC can be used to obtain 3D information about the bone surface, register a pre-operative computational model, and ultimately solve the navigation issues by providing guidance using augmented reality, virtual reality, or robotic actuation.

VTIAC introduces many differences relatively to other embodiments of OT/ET in the context of computer-aided surgery in general and arthroscopy in particular. For example, the global world reference frame, instead of being the external stereo head (the base station), is substituted by the system of coordinates of the WM that is inside the articular cavity. This avoids issues related to preserving lines of sight in the OR, as well as the need of having marker tools protruding through patient skin. Second, for example, the approach relies on processing the video acquired by a free-moving camera, which means that in the case of arthroscopy there is no need of investing in additional capital equipment that provides alternative sensing modalities. Third, for example, measurements are performed in the images acquired at close range inside the anatomical cavity, which dramatically increases spatial and/or metric accuracy with respect to OT or ET.

1.1 Prior Art

In embodiments where the visual marker is a planar marker, the plane-to-image homography may be a factor in the VTIAC approach for surgical navigation. The projection of a plane into a perspective image may be described by a 3×3 matrix transformation (the homography) that encodes the plane rotation and translation (the plane 3D pose) in camera coordinates. The homography has been broadly used in the field of Computer Vision for several different purposes, ranging from camera calibration to visual tracking, and passing by 3D motion estimation.

The use of plane homographies in clinical setups has been relatively scarce. For example, an OT system, the MicronTracker® developed by Claronav®, may use planes with recognizable patterns as tool markers. These markers are tracked by a stereo camera system and the pose of the tool is determined through homography factorization. The approach herein described differs from MicronTracker® in that the tracking is performed by a moving monocular camera as opposed to a stationary stereo setup. Moreover, while in MicronTracker® the base station is the external stereo setup, which raises the issues about line of sight inherent to conventional OT, in VTIAC, measurements are carried out with respect to the WM that is rigidly attached to the surface inside the articular joint or anatomical cavity.

Other embodiments may be used to determine the relative pose between a laparoscope and an intra-operative ultrasound (US) probe or laser projector. In particular, the embodiments attach a printed planar pattern to the probe and/or projector that is viewed by the laparoscope. This enables estimation of the plane-to-image homography and determination of the relative pose of the probe and/or projector in camera coordinates. VTIAC provides a much broader range of functionalities that arise from using a World Marker (WM) attached to the bone surface. Thus, VTIAC not only provides the relative pose of tools and devices that are inserted into the anatomical cavity, but it also enables the reconstruction of points and contours on the surface of the organ of interest that are pin-pointed by the surgeon. This information can be used for a multitude of purposes such as metric measurements, registration of pre-operative models, or guidance using augmented reality, that are seamlessly supported by the framework. Moreover, measurements are typically represented in camera coordinates, which means that it is not possible to relate or integrate information across frames because the laparoscope is in constant motion. In VTIAC, all measurements are stored in the coordinate system of the WM that works as an absolute reference across time and space. Thus, the visual tracking process can even be discontinued, and the 3D information obtained till that moment becomes readily available as soon as the WM is redetected in the images acquired by the moving camera.

1.2 Structure and Notation

Section 2 provides an overview of the concepts behind the VTIAC, Section 3 provides details on the apparatus and calibration of the necessary tools to be used with the system, Section 4 provides a description of the visual markers' accurate detection under high radial distortion, Section 5 details the estimation of 3D pose from the detection of markers in the image and practical capabilities of the system, Section 6 provides an overview of the operation flow of the VTIAC system for operation during surgery and Section 7 provides extensions and variations on the tools and methods presented before.

In order to better illustrate the usefulness of VTIAC, two embodiments that can be applied to design a navigation system for the arthroscopic reconstruction of the Anterior Cruciate Ligament (ACL) and for Placing Pedicle Screws (PPS) in spine surgery are presented (sections 8 and 9). These procedures are mere examples that do not limit in any way the potential applications of VTIAC. As stated in the following sections, the VTIAC can be applied to a multitude of arthroscopic procedures, as well as open procedures and including dentistry surgery.

Notation: If not stated otherwise, points are represented by their vectors of coordinates and vectors are denoted by a bold letter (e.g., P, x). The rigid displacement between coordinate frames is represented by a 4×4 matrix in the Special Euclidean Group (SE(3)) where the left upper 3×3 submatrix is a rotation matrix and 3×1 right upper submatrix is a translation vector. Matrices are typically denoted by plain capital letters (e.g., C, T).

2. Overview of Visual-Tracking Inside the Anatomical Cavity (VTIAC)

The free-moving camera is assumed to be calibrated such that image points u in pixel coordinates can be mapped into image points x in metric coordinates as if the image had been acquired by a perfect pin-hole. For the sake of simplicity, and without lack of generality, it is considered that the free-moving camera is an arthroscopic camera and that the anatomical part of interest is a bone. It is also assumed that visual markers are planar with a known pattern.

Figure 1A:
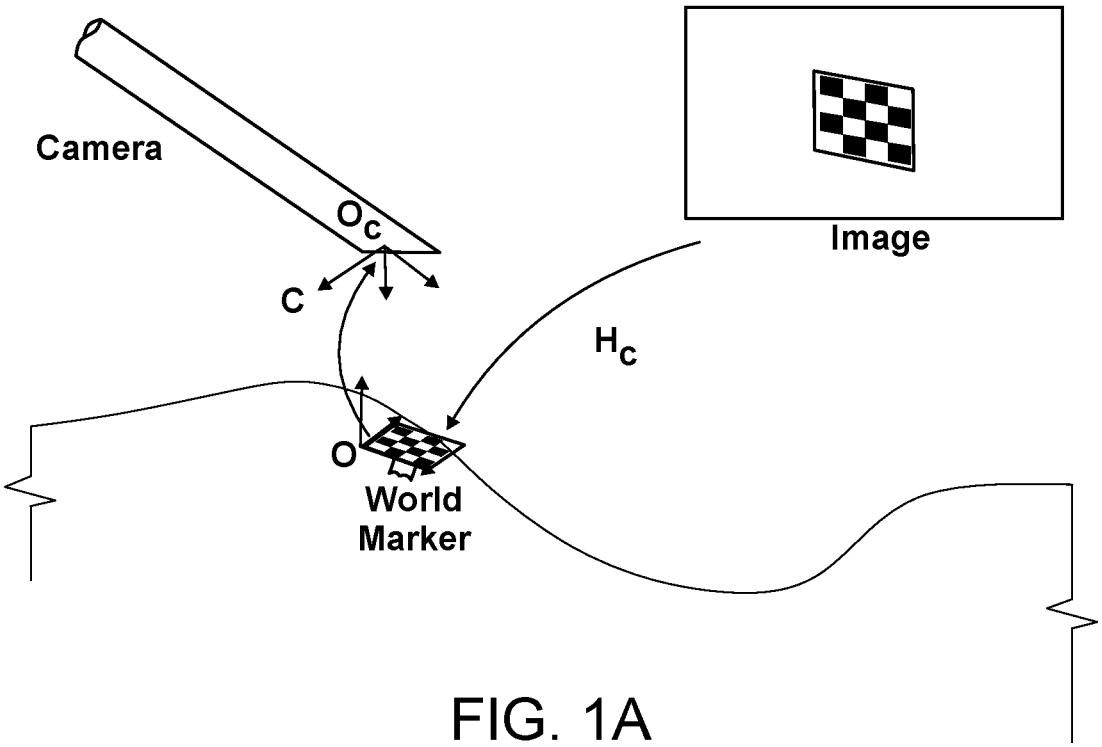
FIG. 1A is an embodiment of a representation of the computation of the World Marker (WM) 3D pose C in the camera reference frame using the homography relation $H_C$ that maps WM points into image points.

After accessing the anatomical cavity, the surgeon starts by rigidly attaching a marker to the bone surface that is referred as the World Marker (WM). If the marker is planar, then its projection is described by an homography $H_C$, that maps plane points into image points, and encodes the relative rotation $R_C$ and translation $t_C$ between marker and camera reference frames. Thus, and since $H_C$ can be estimated from image information, it is possible to use this homography relation to determine at every frame time instant the 4×4 matrix C that transforms world coordinates into camera coordinates (FIG. 1A).

$$C = \begin{pmatrix} R_C & t_C \\ 0 & 1 \end{pmatrix} \quad \text{(equation 1)}$$

Figure 1B:
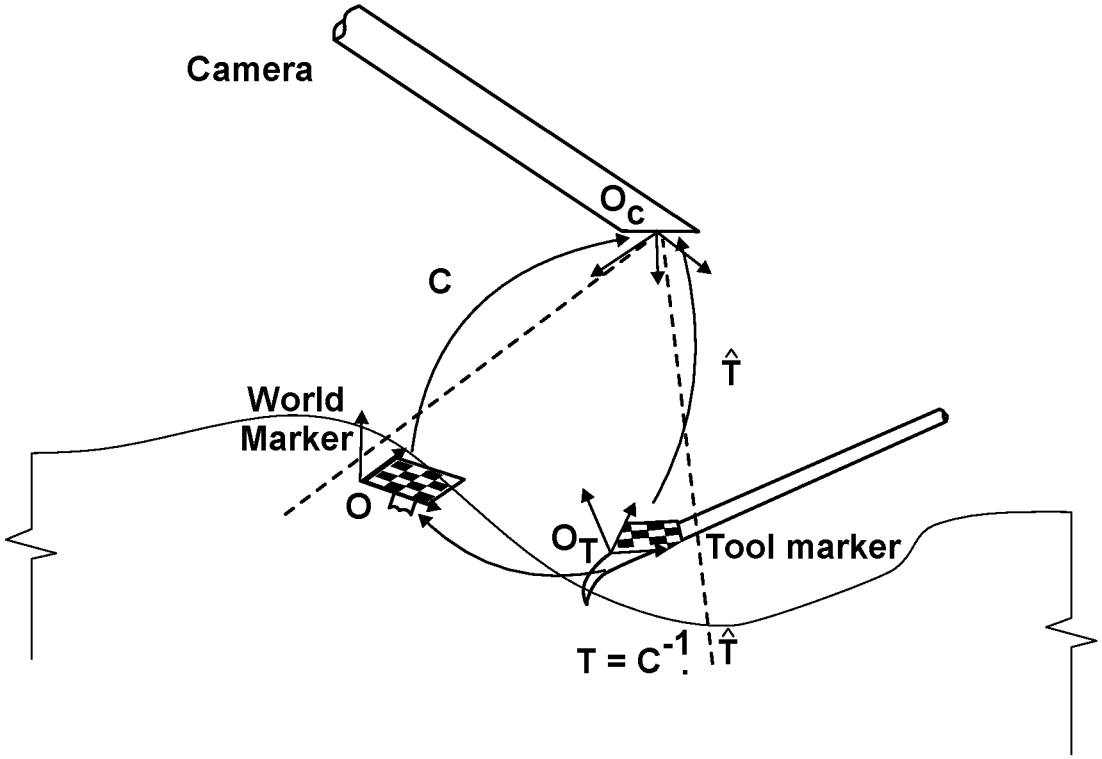
FIG. 1B is an embodiment of a representation of a tool with a Tool Marker (TM) and WM being simultaneously seen by the camera. Both the rigid transform between the WM and the camera (C), and between the TM and the camera ($\hat{T}$) can be computed using the homography relations. The rigid transform between WM and TM (T) can be easily computed from the previous transforms.

Consider now an instrument or tool with a similar visual marker attached that is referred as Tool Marker (TM). Repeating the process of the previous paragraph the homography $H_T$ can be estimated from image information in order to determine the rigid transformation that maps TM coordinates into camera coordinates. If both WM and TM are simultaneously visible in the image, then it is possible to estimate the 3D poses of world and tool markers in the camera frame and find in a straightforward manner the location T of the tool or instrument in the world coordinate system (FIG. 1B)

$$T = C^{-1}\hat{T} \quad \text{(equation 2)}$$

Figure 1C:
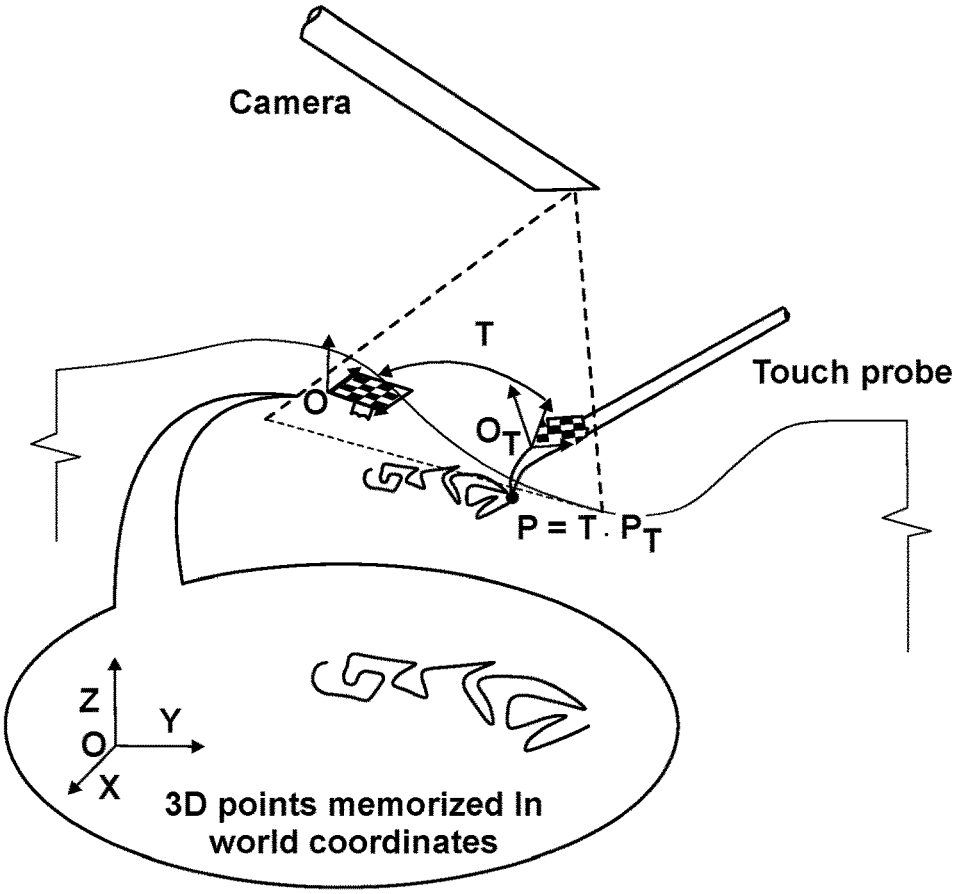
FIG. 1C is an embodiment of a representation of the 3D reconstruction of points, curves, or sparse mesh in the surface of the rigid tissue using a touch-probe with a TM that is calibrated such that the tip $P_T$ is known. By keeping the WM and TM in the FOV of the camera, points P in the bone surface can be referenced in the WM reference frame by mapping $P_T$ using the transformation T that is determined from visual information.

Let's now assume that the tool or instrument is a calibrated touch-probe such that $P_T$ is the vector of 3D coordinates of its tip in the TM reference frame. The surgeon can reconstruct a point of interest in the bone surface by touching it with the probe and acquiring a frame where both WM and TM are visible. This enables computation of the pose T of the probe and the obtaining of the point of interest P expressed in world coordinates (FIG. 1C).

$$\begin{pmatrix} P \\ 1 \end{pmatrix} = T\begin{pmatrix} P_T \\ 1 \end{pmatrix} \quad \text{(equation 3)}$$

The process above can be applied to successive frames in order to reconstruct a curve in the bone surface. In this embodiment the surgeon outlines the contour of interest while keeping both WM and TM in the Field-of-View (FOV) of the free-moving camera. This enables the obtaining of successive P estimates that define the desired 3D curve. Since 3D reconstruction results are stored in World Marker coordinates, the action of outlining can be stopped and resumed at any time. If the process is interrupted for any reason, it suffices for the camera to see again the WM for all the 3D information to be restored without having to repeat the tedious touching process (FIG. 1C).

Figure 1D:
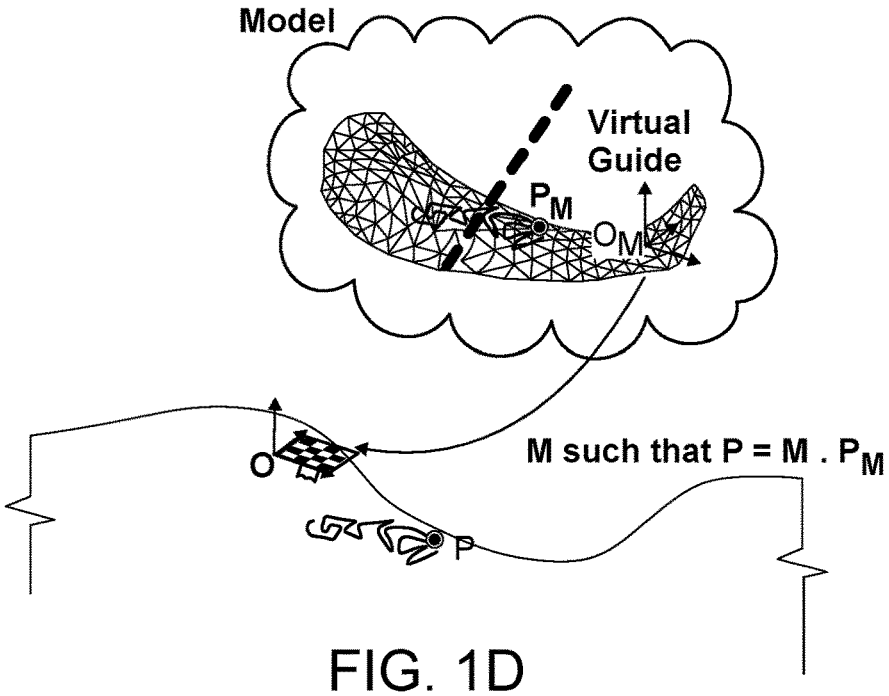
FIG. 1D is an embodiment of a representation of the operation of overlying a surgical plan with the patient's anatomy by using the 3D reconstruction results in a suitable 3D registration algorithm that provides the rigid transformation M that maps surgical plan coordinates into WM coordinates.
Figure 1E:
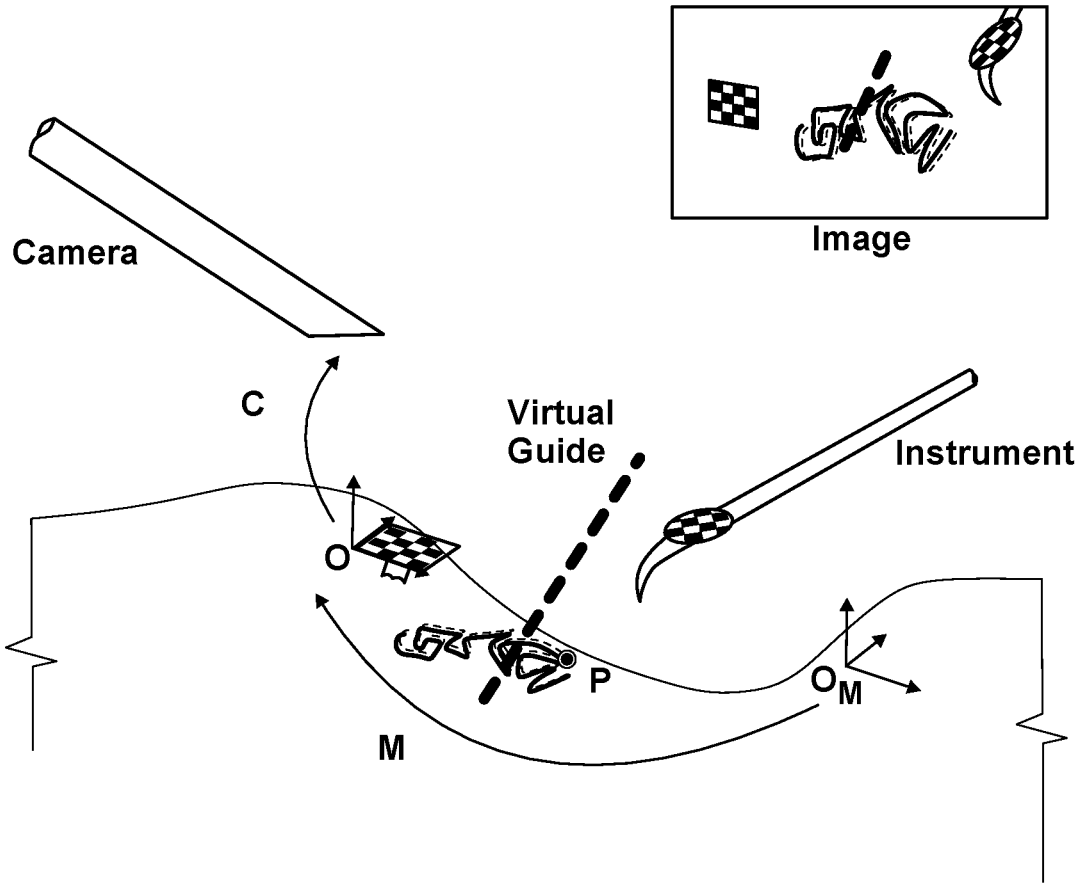
FIG. 1E is an embodiment of a representation of VTIAC assisted execution of a surgical procedure where the surgical plan is overlaid into images in real-time (Augmented Reality) for the purpose of guiding the surgeon in positioning and/or orienting an instrument.

The 3D reconstruction results, that can either be points, contours, or sparse surface meshes, can be used for the purpose of measuring, estimating shape, or overlying a pre-operative plan in the actual patient anatomy (3D registration). This pre-operative plan can be a set of rules using anatomical landmarks, a statistical 3D model of the anatomy of interest, or an actual 3D image of the organ (e.g. CT Scan) augmented with guidance information inserted by the surgeon (surgical plan). Let's assume the latter for illustrative purposes (FIG. 1D). In this case a suitable 3D registration algorithm is selected for estimating the rigid transformation M that maps points $P_M$ in the pre-operative image into corresponding points P in the intra-operative reconstruction obtained with VTIAC (FIG. 1D). This enables representing the information of the model, including guidance information, in the system of coordinates of the world marker or, in other words, to overlay the pre-operative plan with the patient's anatomy (FIG. 1E).

The clinical execution might require, in one embodiment, multiple different instruments—such as guides, drills, shavers, saws, burrs, etc.—that can either be used in sequence or simultaneously. Each one of these instruments is assumed to have a Tool Marker (TM) attached that defines a local system of coordinates where the instrument's relevant parts—such as tip, symmetry axis, or even complete CAD model—are represented. The system processes each frame with the objective of detecting, identifying, and estimating the 3D pose of every TM that is in the FOV of the camera. If the WM is also visible in image, then it is possible to determine the pose of the camera C, locate the instruments in the world coordinate system, relate their poses T with the 3D information stored in the WM reference frame, and ultimately provide real-time assistance to the surgeon (FIG. 1E).

Thus, the last stage of VTIAC consists of assisting the surgeon by performing continuous processing of the video for estimating in real-time the 3D pose of instruments with respect to patient anatomy and/or surgical plan represented in WM coordinates. The assistance can take multiple forms depending on a specific task and a preferred user interface. Possibilities include overlaying guidance information in video using Augmented Reality (AR), using computer graphics to animate the motion of instruments in a Virtual Reality (VR) environment showing the patient's anatomy and/or surgical plan, or controlling the action of actuators in the case of procedures assisted by robotic systems such as the Mako® or the Navio® robots.

3. Overview of Methods, Apparatus and Initial Calibration Requirements

Figure 2A:
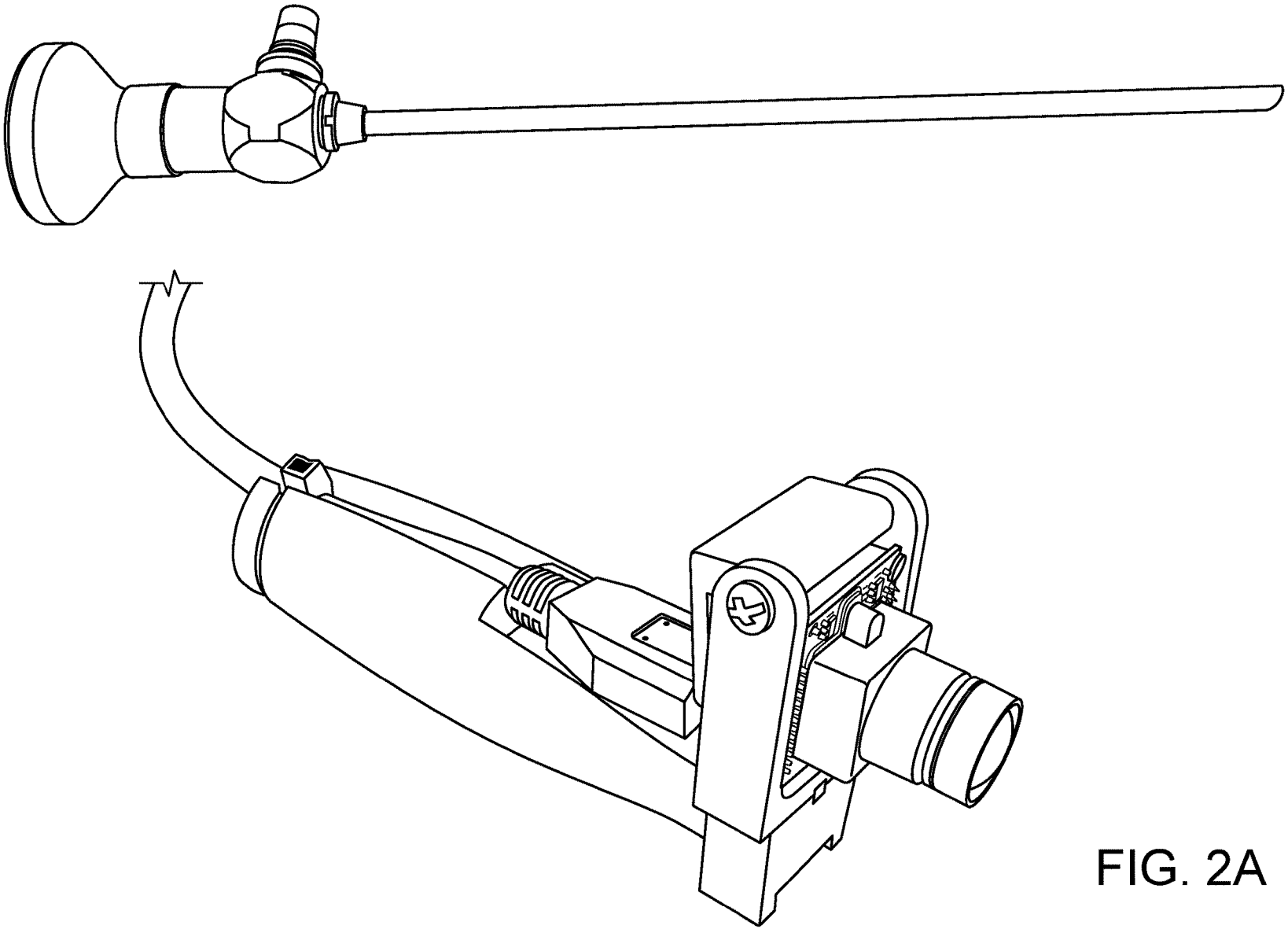
FIG. 2A is an example of some of the free moving cameras that can be used with the VTIAC. Top is an endoscopic lens than can be attached to a camera-head for visualization during arthroscopy, and bottom is a generic handheld camera that can be employed for VTIAC intra-operative navigation in open surgery with direct visual access.
Figure 2B:
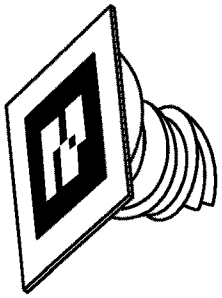
FIG. 2B is an embodiment of a World Marker (WM) that is in this particular case a screw-like object that comprises one planar facet with a known visual pattern that defines the world system of coordinates.
Figure 2C:
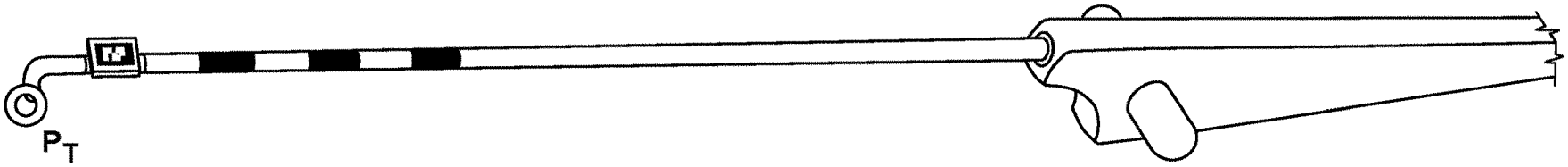
FIG. 2C is an embodiment of a touch-probe with a Tool Marker (TM) attached that defines a local system of coordinates in which the position of the tip $P_T$ is known.
Figure 2D:
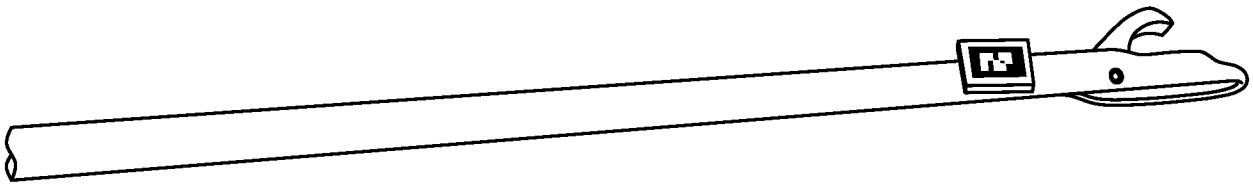
FIG. 2D is an embodiment of a surgical instrument with a Tool Marker (TM) attached to the surgical instruments for execution of the clinical procedure. The surgical tool can be any tool used during the operation, including but not limited to powered tools (e.g. resection bur), drill guides, or any other instrument used for resection or palpation. The TM defines a local system of coordinates in which the position of instrument's relevant parts—such as tip, symmetry axis, or even a complete CAD model of the instrument—are known.
Figure 2E:
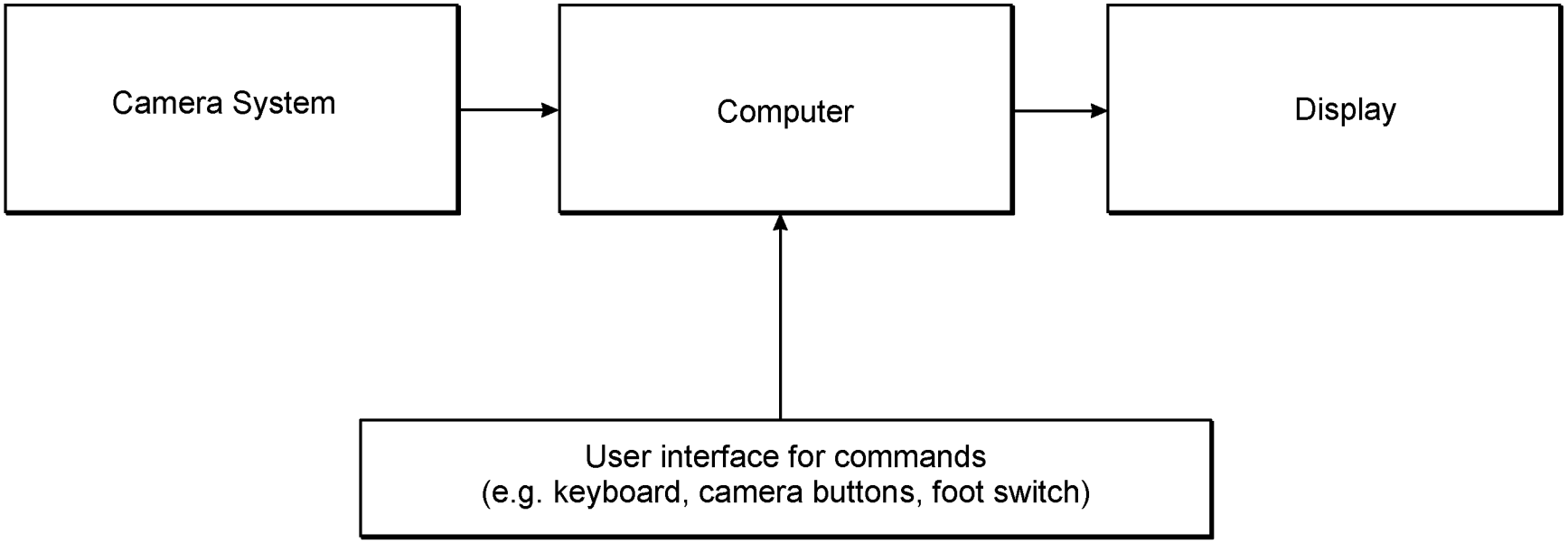
FIG. 2E is a schematic of an embodiment of the image processing system, that may correspond to or may be part of a computer and/or any other computing device, that receives as input images and video acquired by the camera, as well as commands that may be entered by a button panel, keyboard, camera buttons, foot switch and/or any other input interface, and that outputs the processing results to a display.

This section overviews the methods and apparatus that are required to perform computer-aided surgery using VTIAC. The apparatus includes:

(i). A free-moving camera, that can either be an arthroscopic camera or a generic handheld camera, and that is calibrated at all times such that image points in pixel units can be back-projected into directions or image points expressed in the metric coordinate system of the camera (FIG. 2A);

(ii). A visual marker, henceforth referred as the World Marker or WM, consisting in an object that is meant to be rigidly attached to a surface, that comprises at least one planar facet with a known pattern that can be secured (e.g., glued), printed or engraved, and where this pattern defines the world system of coordinates (FIG. 2B);

(iii). A touch-probe that is a tool or instrument of any material comprising a handgrip and a tip, and that has at least one visual marker, henceforth referred as Tool Marker or TM, that consists in at least one planar facet with a known pattern that can be secured (e.g., glued), printed or engraved, and where the pattern defines a local system of coordinates in which the position of the tip $P_T$ is known (FIG. 2C);

(iv). The surgical instruments for proper execution of the clinical procedure, where each instrument has at least one visual marker, henceforth referred as Tool Marker or TM, that includes at least one planar facet with a known pattern that can be secured (e.g., glued), printed or engraved, and where the pattern defines a local system of coordinates in which the position of instrument's relevant parts—such as tip, symmetry axis, or even a complete CAD model of the instrument—are known (FIG. 2D);

(v). An image processing system, that may correspond to or may be part of a computer and/or any other computing device, that receives as input images and video acquired by the camera (i), as well as commands that may be entered by a button panel, keyboard, camera buttons, foot switch and/or any other input interface, and that outputs the processing results to a display and/or to a robotic actuator (FIG. 2E);

where this apparatus is used in the following actions or methods:

(vi). Placement of the WM in an arbitrary location in the surface of the rigid anatomical part of interest, with this placement being such that WM and part of interest do not move with respect to each other.

(vii). 3D reconstruction of points and/or contours in the surface of the rigid anatomical part by using the touch-probe to pin-point those points and/or outline those contours while keeping both WM and TM of the probe in the Field-of-View (FOV) of the camera (FIG. 1C).

(viii). Application of 3D reconstruction results for the purpose of measuring, making inference, or overlaying a pre-operative surgical plan with the current patient's anatomy, in which case a suitable 3D registration method may be used for determining the rigid displacement between the coordinate system of the WM, that is attached to the anatomy of interest, and the reference frame of the surgical plan (FIG. 1D).

(ix). Assisted clinical execution using the surgical instruments of (iii) where the camera simultaneously observes the TMs and the WM for locating the instruments in world coordinates, and where real-time guidance is accomplished by relating these locations with 3D reconstructions results and/or overlaid surgical plan (FIG. 1E).

3.1 Calibration of Free-Moving Camera

Since the VTIAC uses images for measurements and 3D inference, the free-moving camera must be calibrated at all times during the procedure such that 2D image points u, represented in pixel coordinates, can be mapped into 2D points x (or back-projection directions) represented in the metric system of coordinates of the camera. The calibration includes determining the vector of parameters k and $\xi$ of the back-projection function $f^{-1}$ (the inverse of the projection function f) where k comprises the so-called intrinsic parameters—focal length, principal point, aspect ratio, and skew—and $\xi$ stands for the radial distortion parameters.

$$x=f^{-1}(u;\ k,\ \xi) \qquad \text{(equation 4)}$$

The camera can either be pre-calibrated from factory, using any standard method in literature, or calibrated in the Operating Room (OR) just before starting the procedure. The latter is especially recommendable for the case of arthroscopic cameras, or any other camera with exchangeable optics. The calibration in the OR can be quickly accomplished by acquiring one image of a known calibration pattern from an arbitrary viewpoint, as described in U.S. Patent Publication No. 2014/0285676, which is incorporated by reference in its entirety. If the camera parameters change during operation because the surgeon rotates the lens scope and/or varies the optical zoom, then the initial calibration may be updated at every frame time using the techniques described in U.S. Patent Publication No. 2014/0285676 and Patent Publication WO2014054958, both of which are incorporated by reference in their entireties. The camera calibration must also take into account the medium of operation that, in the case of arthroscopy, is a wet medium. In this situation the initial single image calibration can either be carried in wet medium, or performed in air followed by compensating for the difference in the refractive index of air and water-based medium.

3.2 World Marker (WM) and Tool Markers (TMs).

The surgeon starts by fixing the World Marker (WM) to the bone surface. The WM can be any object comprising at least one planar facet with a known pattern that can be secured (e.g., glued), printed or engraved, and that can be recognized in images; that is small enough to be inserted into the anatomical cavity (e.g., up to 5 mm diameter in the case of arthroscopy); and that can be mechanically attached to the surface such that bone and marker do not move with respect to each other.

A non-exhaustive list of objects that can be used as WM includes: a screw-like object with a flat head or facet (FIG. 2B); a nail-like object to be fixed by pressure with a flat head or facet; a needle like object with a flat lateral facet for trans-dermic insertion into the joint or cavity; or a flat button-like object that is pulled inside the joint or cavity by a thread or guide.

The touch-probe in (iii) and the surgical tools in (iv) are instrumented with a visual marker (the Tool Marker or TM), which can either be originally built-in at manufacturing time, or rigidly attached by the user (FIG. 2C, FIG. 2D). Depending on the tool purpose, the tip of the tool, the orientation of the tool, or a complete CAD model of the tool may be registered in the TM coordinate frame (FIG. 2C). This registration process as described herein is referred to as tool calibration that can either be carried in factory for built-in markers, or performed by the user in case the markers are attached to the tool before starting the procedure.

3.3 Tool Calibration in the Operating-Room (OR)

Figure 2F:
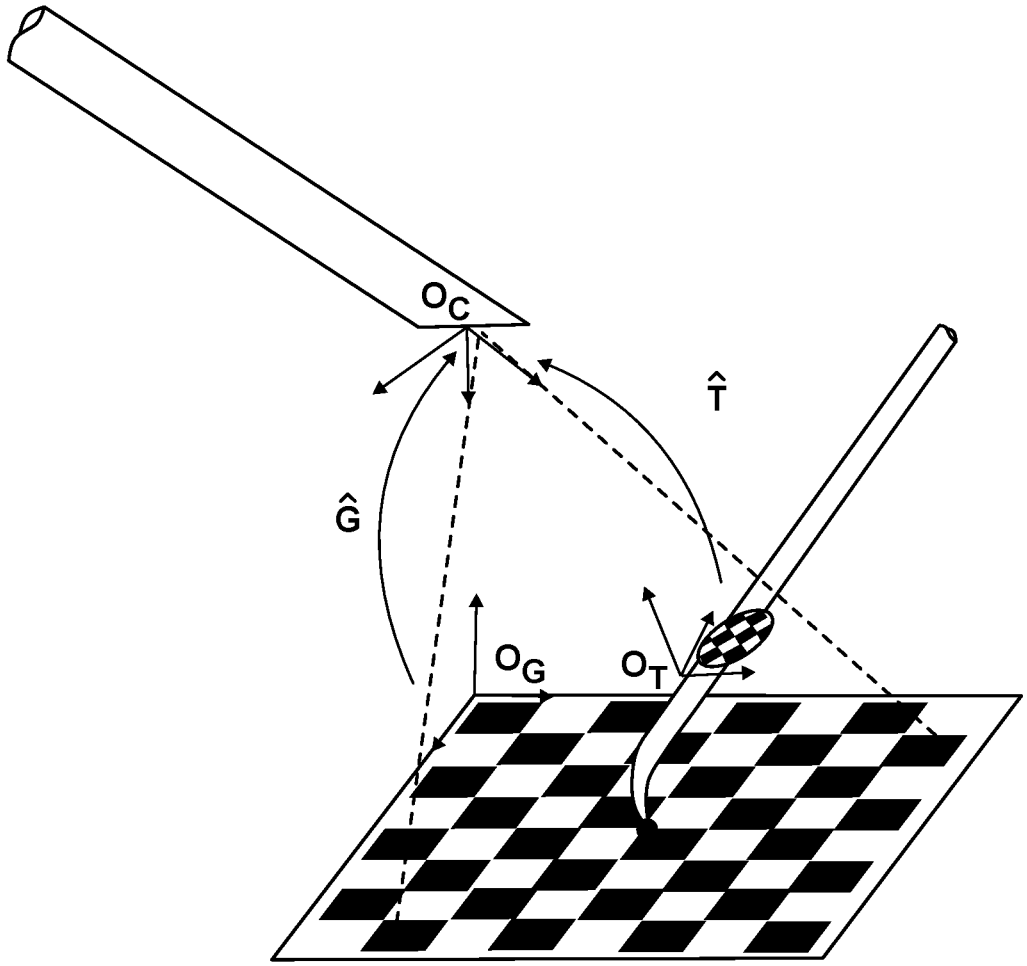
FIG. 2F is an embodiment of a representation of the tool calibration process, which includes finding the coordinates $P_T$ of a particular tool point in the TM reference frame. The calibration operation can be quickly carried in simultaneous with the initial calibration of the camera without requiring the acquisition of additional calibration frames. The rigid transformation $\hat{G}$ maps coordinates in the grid reference frame into coordinates in the camera reference frame. When the tool tip is placed in a pre-defined point $P_G$ that is known in grid coordinates, and the calibration image is such that TM is visible, then it is possible to estimate the 3D pose $\hat{T}$ of the tool marker from image information and obtain the TM coordinates of the tool tip.

If the tool calibration includes finding the coordinates $P_T$ of a particular tool point in the TM reference frame (e.g. the tip of the touch probe (iii)), then the operation can be quickly carried simultaneously with the initial calibration of the camera without requiring the acquisition of additional calibration frames. As described, e.g., in U.S. Patent Publication No. 2014/0285676, the camera calibration can be accomplished by acquiring a single image of a known grid or checkerboard pattern. This enables recovering the intrinsic parameters k, the radial distortion parameters $\xi$, and the rigid transformation $\hat{G}$ that maps coordinates in the grid reference frame into coordinates in the camera reference frame. Thus, if the tool tip is placed in a pre-defined point $P_G$ that is known in grid coordinates, and the calibration image is such that TM is visible, then it is possible to estimate the 3D pose $\hat{T}$ of the tool marker from image information and obtain the TM coordinates of the tool tip by applying the formula below (FIG. 2F).

$$\begin{pmatrix} P_T \\ 1 \end{pmatrix} = \hat{T}^{-1}\hat{G}\begin{pmatrix} P_G \\ 1 \end{pmatrix} \qquad \text{(equation 5)}$$

The tool calibration of the surgical instruments (iv) can either consist in determining the location of a point, a line or axis, or a CAD model in the coordinate system of the TM attached to the particular instrument. This can be accomplished with the help of the calibrated camera and touch-probe using a method similar to the one used for 3D reconstruction on the bone surface, but where the role of the WM is replaced by the TM of the instrument (FIG. 1C). Thus, for the case of a single point it is enough to pin-point it with the probe while keeping both the TM and the marker of the probe in the camera FOV. For the case of a line or axis the procedure is performed at least two times to reconstruct two points in TM coordinates lying on the line or axis. Finally, if the objective is to register a CAD model of the tool, then the procedure may be performed at least three times to obtain three landmark points in TM coordinates to be used as input in a standard registration method.

3.4 Alternatives and Extensions in the Physical Configuration of Visual Markers

The visual marker used in the WM of (ii) and in the TMs of (iii) and (iv) can comprise a single plane facet with a known pattern as assumed so far, or multiple plane facets with each facet having its own pattern that can be secured (e.g., glued), printed, or engraved, and where the location of each planar pattern is known in a common local coordinate system of the visual marker. The advantage of having multiple planar patterns facing different directions is to extend the range of viewing positions and orientations from which the marker can be observed by the camera for estimating the relative 3D pose (FIG. 1A, FIG. 1B). In the case of TMs, the planar patterns can even be spread across different locations in the tool surface, in which case it suffices for the camera to see one of those patterns to successfully compute the relative pose $\hat{T}$.

Alternatively, the visual marker can be non-planar, in which case it should comprise $n \geq 3$ points with known coordinates in the local reference frame of the marker, with these points being such that they can be detected and identified in image in order to allow estimation of the relative pose by applying a Perspective-n-Point (PnP) method.

4. Estimation of Rotation and Translation (the 3D Pose) of a Known Planar Pattern from Image Information.

The small visual markers that are attached to instruments, tools, and anatomy of interest play a fundamental role in VTIAC being key-enablers for using the camera as a measuring device for determining 3D pose. As discussed, the visual marker can have different topological configurations but, for the sake of simplicity and without compromising generality, it will be assumed that the visual marker is a planar surface with a known pattern.

This planar pattern should be such that it has a local system of coordinates, it is amenable to be detected and uniquely identified from its image projection, and it has fiducial points that can be accurately detected in image for estimating the plane-to-image homography H from point correspondences. A point correspondence is the association between a point in the pattern p expressed in local coordinates and its projection x represented in camera coordinates. The homography H is a projective transformation that maps the former into the latter, and that can be linearly estimated from N≥4 point correspondences. The homography encodes the rotation and translation between pattern and camera coordinate systems, which means that the factorization of H provides the 3D pose of the pattern in the camera reference frame.

Figure 3A:
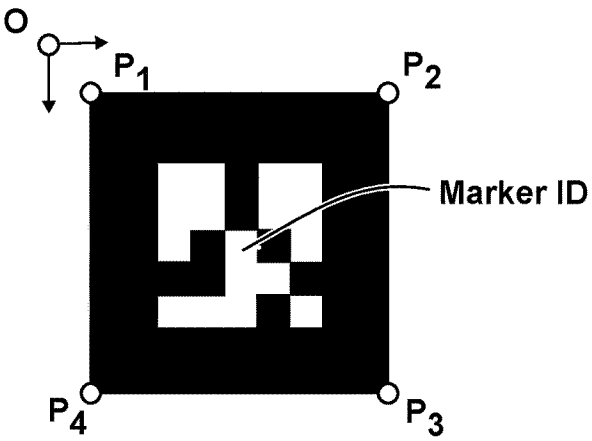
FIG. 3A is an embodiment of a planar pattern template (synthetic image), where the quadrilateral shape and high contrast enable fast detection of the corners, the sharp corners provide accurate point detection ($P_1$, $P_2$, $P_3$ and $P_4$), and a bitmap binary code allows visual identification.
Figure 3B:
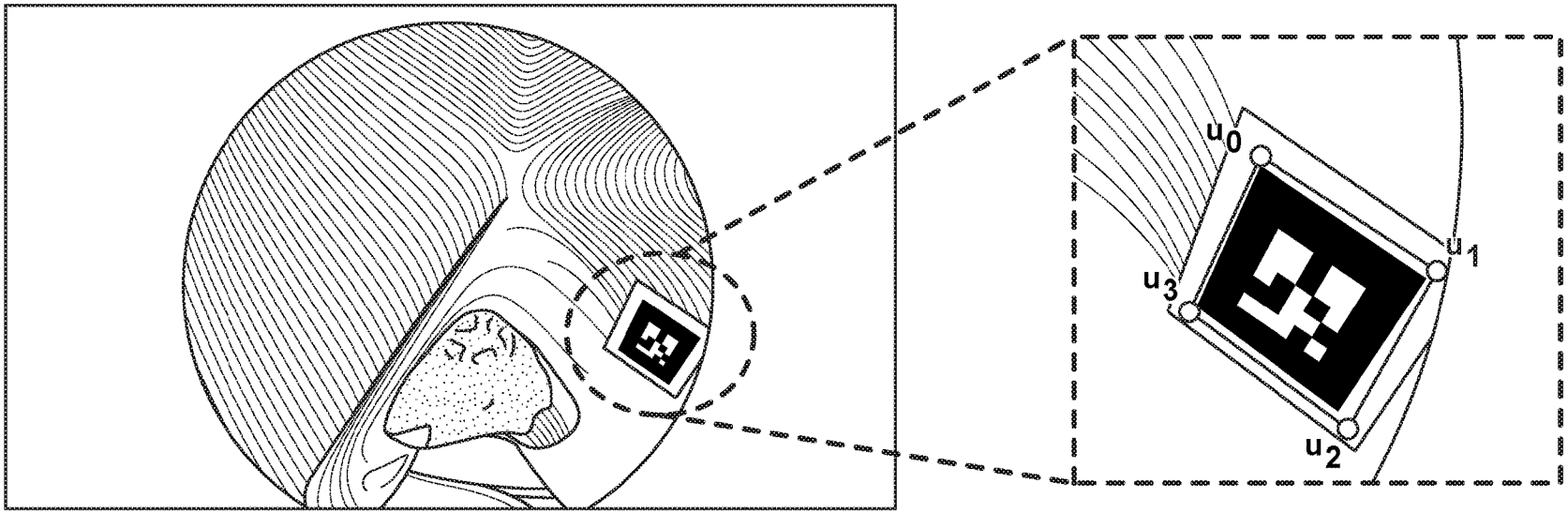
FIG. 3B is an embodiment of the result of detection and identification of a planar marker in close-range operation using a wide FOV camera that introduces very strong radial distortion. The correct detection and point correspondences ($u_1$, $u_2$, $u_3$ and $u_4$ against $P_1$, $P_2$, $P_3$ and $P_4$ of the template pattern) is not accurate enough for the demands of the medical applications, due to the compression effect of the radial distortion in the periphery of the image.

There are several pattern designs that meet the above mentioned conditions. It will be assumed, without compromising generality, that the planar patterns are similar to the CalTag checkerboard patterns, where the quadrilateral shape and high contrast enable fast detection, the sharp corners provide accurate point correspondences, and a bitmap binary code allows visual identification (FIG. 3A). These patterns are broadly used as fiducial markers for applications in augmented reality, for which there are several image processing pipelines such as the ARToolKit or the ALVAR. These pipelines implement the steps of detection, identification, and homography estimation in a computationally efficient manner to provide the 3D pose of each planar pattern at every frame time instant. Unfortunately, the application to computer-aided surgery is not straightforward because the close-range operation requires cameras with a wide FOV that typically introduce very strong radial distortion. The distortion hinders correct detection and point correspondences, which is not compatible with the high-accuracy demands of the medical applications (FIG. 3B).

One possibility for improving accuracy and robustness of 3D pose estimation is to correct radial distortion via software, before running the processing pipeline for detection, identification, and homography/pose estimation. However, this has several drawbacks, such as the computational effort in warping the entire frame, and the fact that interpolation also introduces artifacts that degrade the accuracy of geometric estimation.

Since radial distortion has a relatively small impact in pattern detection, this disclosure provides an alternative approach based in photo-geometry. The approach includes using standard methods for detection, identification, and initial estimation of pattern rotation $r_0$ and translation $t_0$, followed by refining the 3D pose estimate by minimizing the photo-geometric error in aligning the current pattern image with its template using a warping function that takes into account the non-linear distortion.

Figure 3C:
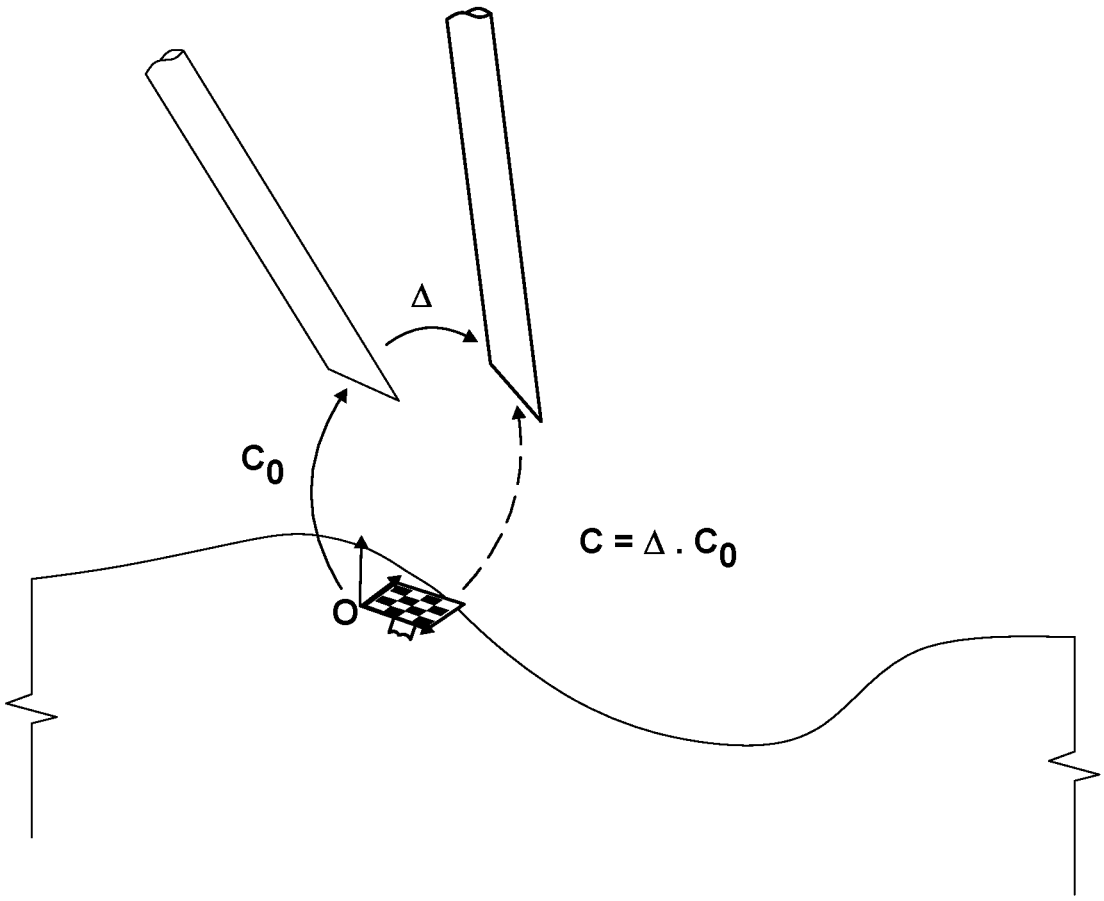
FIG. 3C is an embodiment of the representation of the camera pose estimation using the detection on the highly distorted image ($C_0$) and the camera pose estimation (C) after computing the pose update Δ. This pose update is computed by minimizing the photo-geometric error between the template pattern and the detection on the image.
Figure 3D:
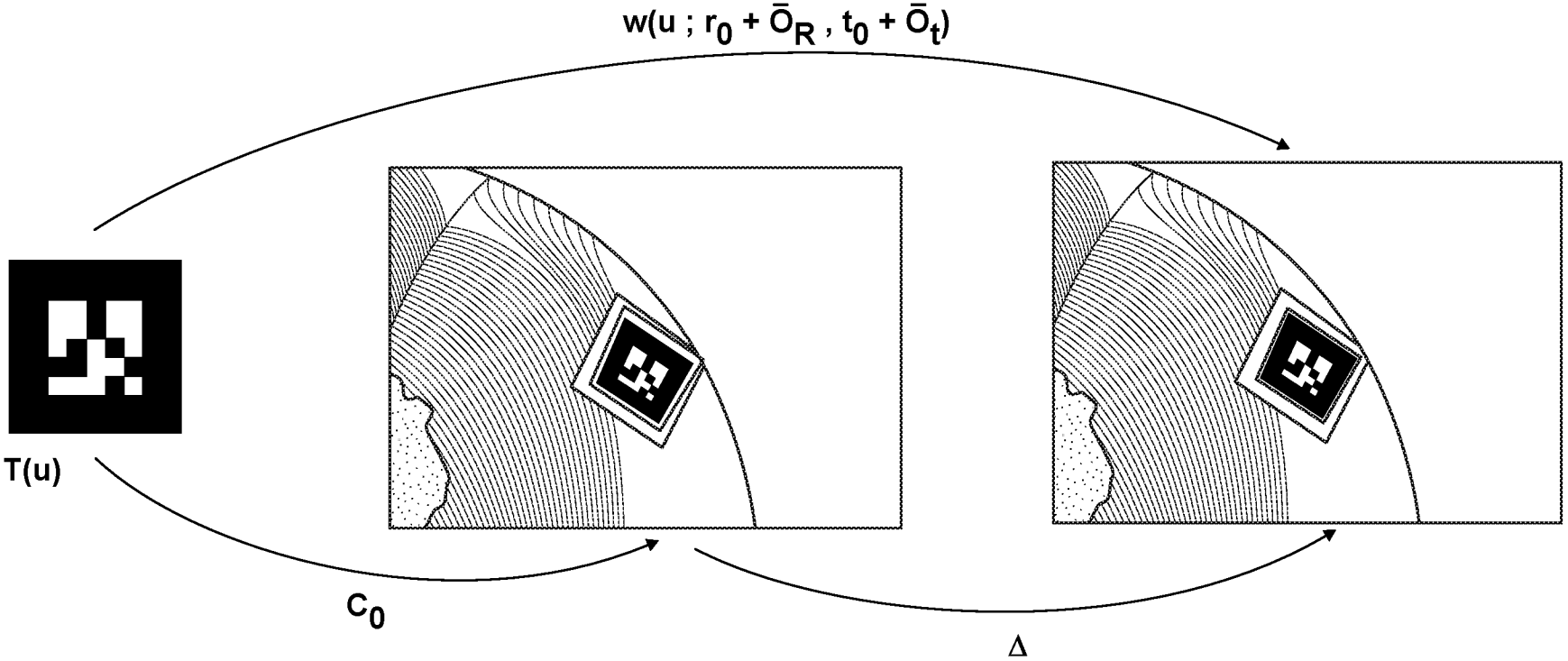
FIG. 3D is an embodiment of a representation of the warping operation for the minimization of the photo-geometric error between the template pattern and the current marker detection in the image. The pose update Δ encodes the increments in rotation $\delta_R$ and in translation $\delta_t$, that are estimated taking into account the amount of distortion in the image for increased accuracy.

Let $C_0$ be the initial 3D pose estimate of the planar pattern in camera coordinates. The objective is to determine the pose update Δ, that encodes the increments in rotation $\delta_R$ and in translation $\delta_t$, such that the photo-geometric error $\varepsilon_1$ is minimized (FIG. 3C, FIG. 3D)

$$\epsilon_i = \sum_{u \in N_i} [I(w(u; r_0 + \delta_R, t_0 + \delta_t)) - T(u)]^2 \quad \text{(equation 6)}$$

where T(u) is the pattern template, I(u) is the current frame, $N_i$ is the image region comprising the pattern, and w is the image warping function (FIG. 3D) given by $$w(u; r, t) = f(x: k, \xi) \circ h(x; r, t) \circ f^{-1}(u; k', \xi') \quad \text{(equation 7)}$$

with h being the homography map that depends on the relative 3D pose r and t, and f denoting the projection function of the camera that encodes the effect of radial distortion, as described, e.g., in Patent Publication WO/2014054958. Since the template can be understood as a synthetic, fronto-parallel image of the planar pattern (FIG. 3D), that has calibration parameters k' and ξ', the homography h depends on the rigid displacement of the views. The final 3D pose estimate is given by:

$$C = \Delta C_0 \quad \text{(equation 8)}$$

The iterative minimization of the photo-geometric error $\varepsilon_i$ can be carried using different optimization schemes available in literature such as forward composition, inverse composition, or efficient second order minimization, which requires some changes in formulation and parametrization in SE(3). The formulation can also be extended to be resilient to changes in illumination.

5. 3D Measurement and Reconstruction using VTIAC.

Section 4 describes a method for estimating the 3D pose of a planar visual marker in camera coordinates. Let's consider two of these markers such that one is attached to the anatomy of interest (WM), and the other is attached to a calibrated touch probe (TM).

Figure 4A:
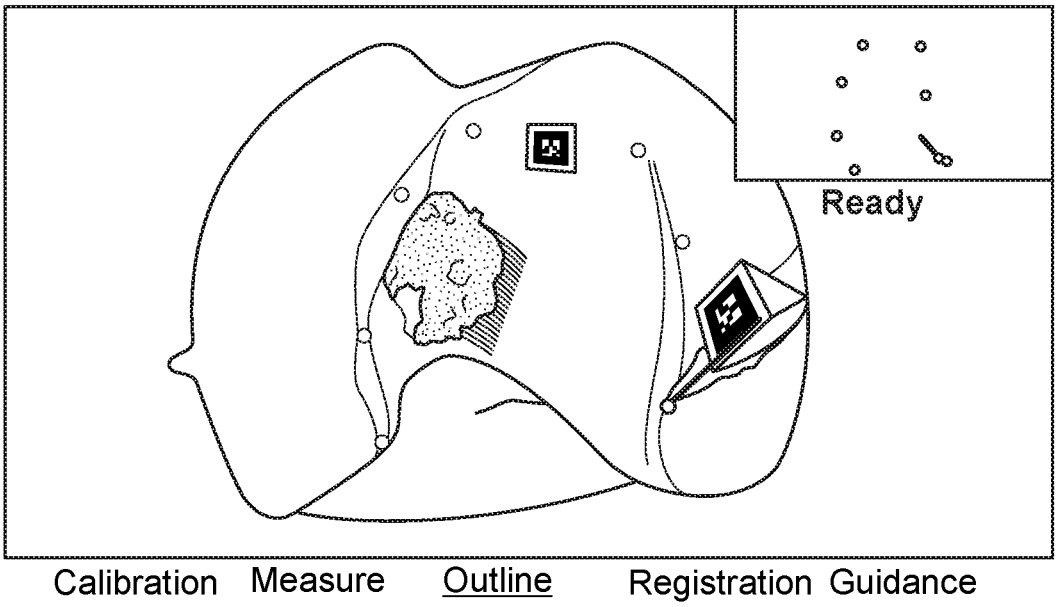
FIG. 4A is an embodiment of the VTIAC reconstructing points in 3D in ACL reconstruction. The tip of the probe is positioned such that both WM and TM are in the FOV of the camera. Points position in 3D are memorized by the system in the reference frame of the WM. The figure shows the Augmented Reality (AR) view, where information is overlaid, and in the top right corner the Virtual Reality (VR) view where points are displayed in 3D.

For reconstructing an arbitrary point P in world coordinates the surgeon places the tip of the probe in the point, positions the camera such that both WM and TM are in the FOV, and commands the system to acquire an image that is processed as follows (FIG. 4A):

(i). Detect, identify, and estimate the 3D pose C of the WM in camera coordinates using the method in section 4.

(ii). Detect, identify, and estimate the 3D pose $\hat{T}$ of the TM in camera coordinates using the method in section 4.

(iii). Reconstruct point P in world coordinates by applying the formula $$\begin{pmatrix} P_T \\ 1 \end{pmatrix} = C^{-1}\hat{T}\begin{pmatrix} P_T \\ 1 \end{pmatrix}$$

with $P_T$ being the 3D coordinates of the probe tip expressed in the TM reference frame (iv). Store the reconstructed point P in memory for future reference.

Figure 4B:
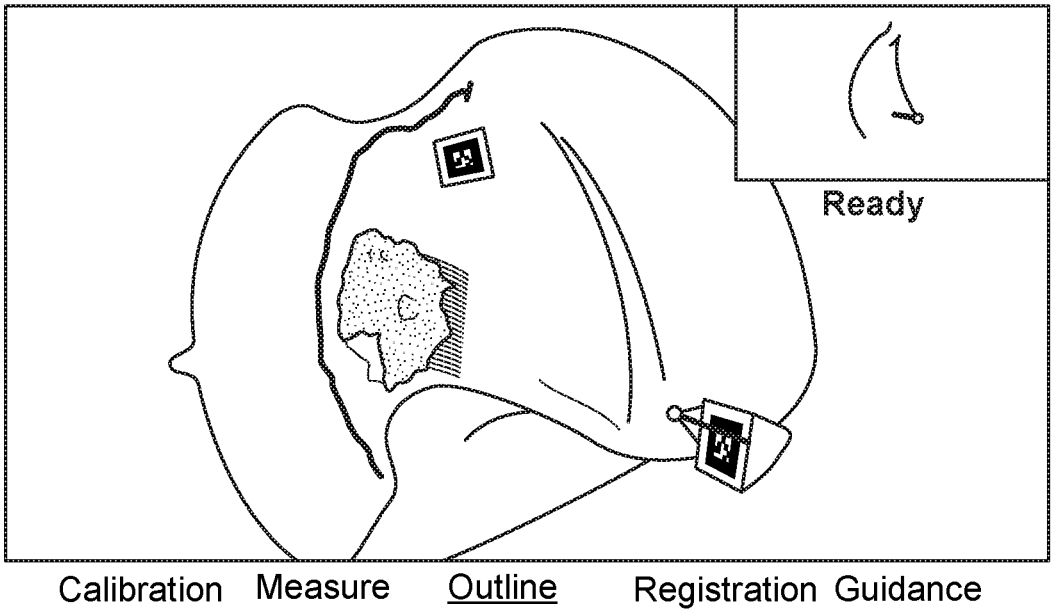
FIG. 4B is an embodiment of the VTIAC reconstructing curves in 3D in ACL reconstruction where the surgeon uses the touch-probe to outline the curves. These particular curves are the inter-condyle contours that are overlaid in image and shown in 3D in the VR window in the top right corner of image.
Figure 4C:
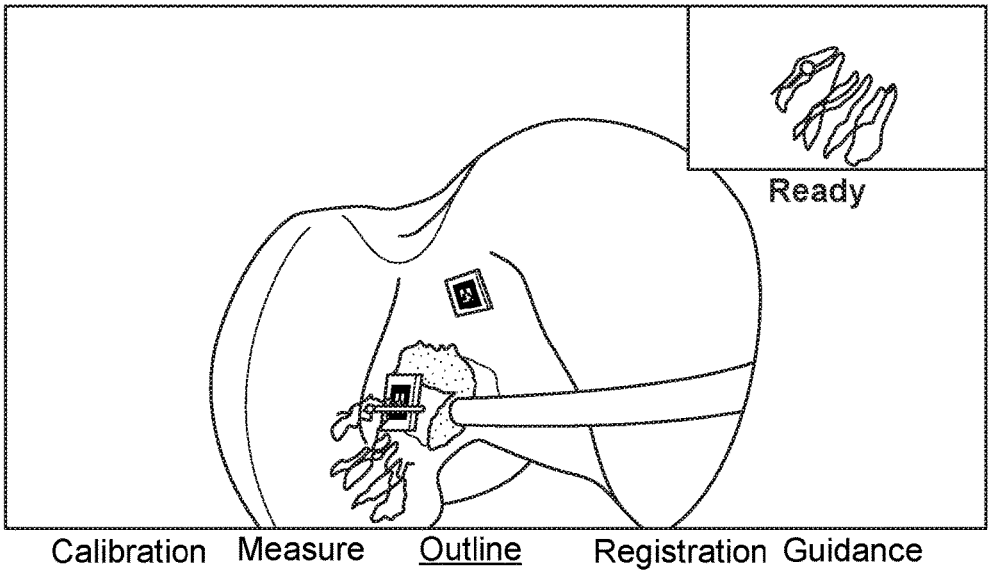
FIG. 4C is an embodiment of the VTIAC reconstructing a dense surface by randomly grasping the bone surface with an instrumented tool. On the upper right corner, the reconstructed points in 3D are shown, along with a graphical representation of the touch probe.

The approach can be extended to obtain a 3D contour or a sparse 3D reconstruction of a surface region, in which case the surgeon uses the touch probe to respectively outline the contour or randomly grasp the surface, while the camera acquires continuous video and steps above are executed for each frame (FIG. 4B, FIG. 4C).

The 3D reconstruction results are stored in memory in world coordinates, which means that they can be overlaid in images whenever the WM is in the camera FOV by performing the following steps at each frame time instant (FIG. 4A, FIG. 4B, FIG. 4C):

Detect, identify, and estimate the 3D pose C of the WM in camera coordinates using the method in section 4.

Map 3D data from world coordinates into camera coordinates using C.

Project the 3D data into image using function f with camera calibration parameters k, ξ.

Figure 4D:
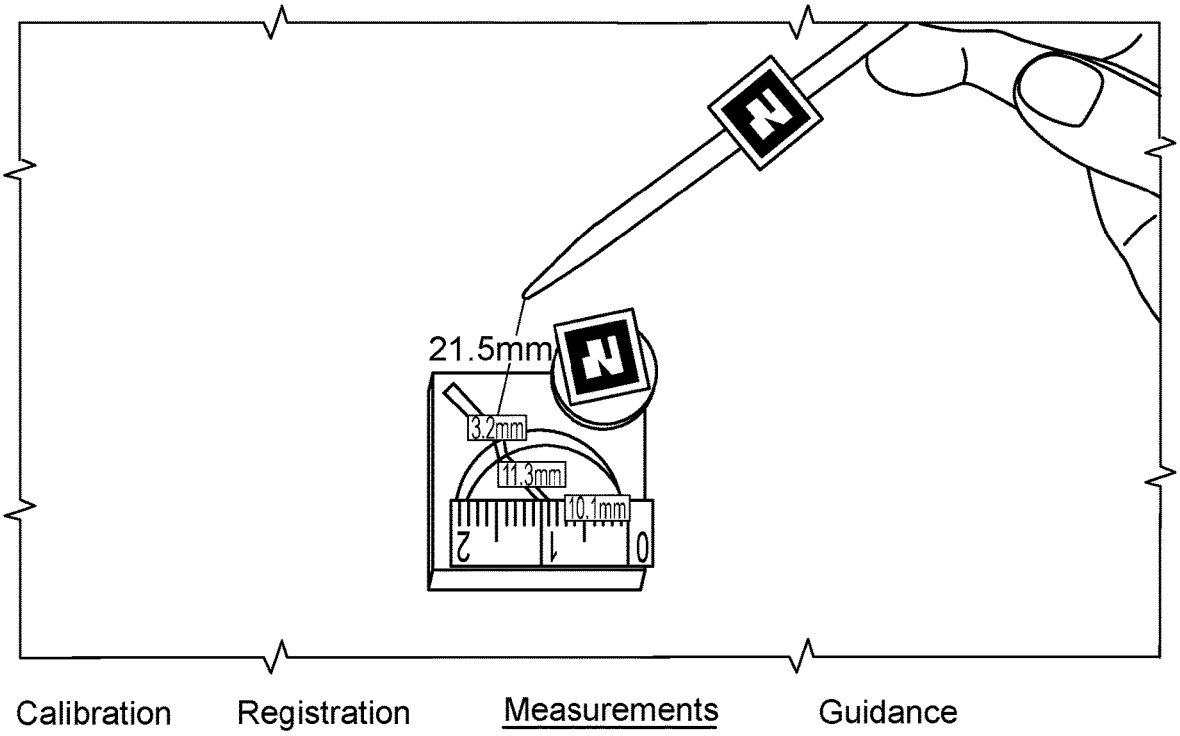
FIG. 4D is an embodiment of using the VTIAC to measure distance between points. By pinpointing points with a calibrated tool, TM coordinates are transferred to the WM reference frame, and distances are computed with sub-millimetric accuracy.
Figure 4E:
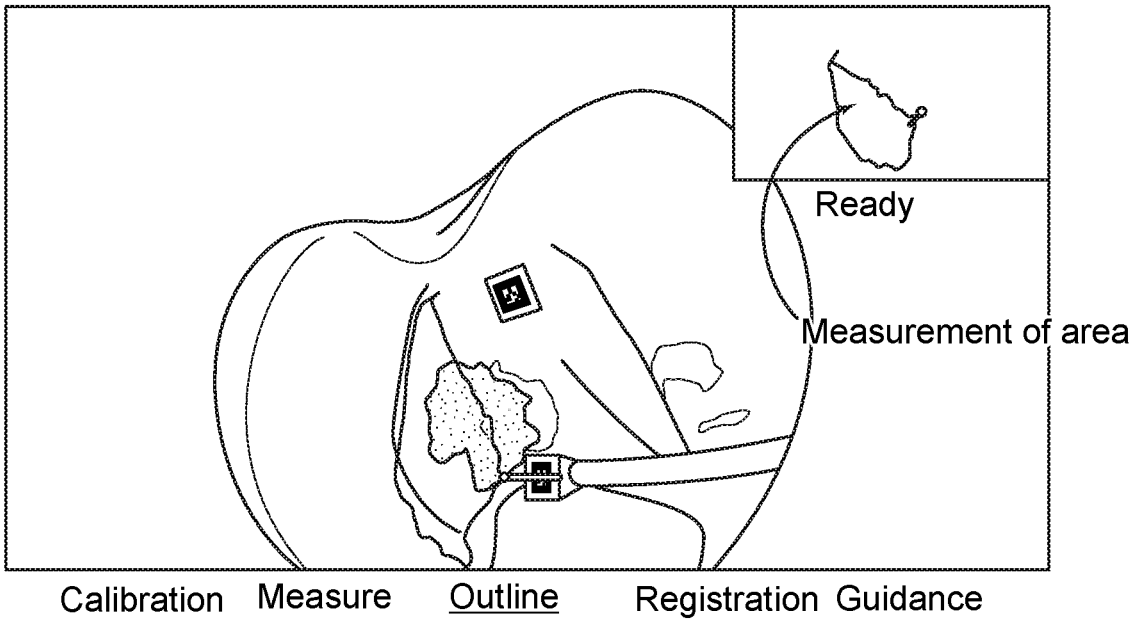
FIG. 4E is an embodiment of using the VTIAC to measure shape and/or area of a region by establishing a closed contour on the bone surface. This shape can then be analyzed to infer metrics such as area of tissue to remove or volume of implants needed for surgery.

The ability of VTIAC to reconstruct and store in memory points, curves, and regions in the anatomy of interest (e.g. bone) has a multitude of purposes and/or possible clinical applications. A non-exhaustive list includes:

measuring the distance between two points (FIG. 4D);

measuring thickness (e.g. of cartilage coating);

measuring depth (e.g. of perforation or insertion);

measuring volume of a protruding or sunken region (e.g. a confocal cartilage defect);

finding shape and/or area of a region by determining its boundary contour (FIG. 4E);

fitting a parametric curve and/or shape;

As stated, the reconstruction results can also be used as input in standard 3D registration methods for aligning or overlying a computational model with the current patient's anatomy. Such methods estimate the rigid transformation M that maps points $P_M$ in the model into corresponding points P in the intra-operative reconstruction obtained with VTIAC (FIG. 1D).

6. Assisted Execution of the Clinical Procedure using VTIAC.

So far we have shown how to obtain relevant 3D data in the common coordinate system of the WM that may consist in reconstruction results, measurements and other types of 3D inferences, or the registration of surgical plan against patient's anatomy. The term 'surgical plan' is employed in a broad sense and can mean, among other things, a set of rules based on anatomical landmarks, e.g. placing the femoral tunnel of the ACL at ⅓ the length of the notch ceiling measured from its posterior end; the fitting of a statistical model of an anatomy or pathology, e.g. the shape model of CAM femuro-acetabular impingement; or a pre-operative image of the targeted anatomy that can, or cannot, be augmented with guidance information, e.g. a CT scan annotated by the surgeon using a 3D planning software. This section describes how VTIAC can combine this 3D data with real-time 3D pose estimation of surgical instruments to provide intra-operative navigation features.

Let the surgical instrument—that can be a needle, guide, drill, shaver, saw, burr, or any other object required for proper clinical execution—have a TM attached. The marker defines a local reference frame where the position of a point, axis, or CAD model of the tool is known (calibrated tool). Navigation is accomplished by executing the following processing steps at every frame time instant:

(i). Detect, identify, and estimate the 3D pose C of the WM in camera coordinates using the method in section 4.

(ii). If the pose C has been successfully estimated proceed as follows:

1. Detect, identify, and estimate the 3D pose $\hat{T}$ of the TM in camera coordinates using the method in section 4.
2. If pose $\hat{T}$ of the surgical instrument is successfully estimated then
   - Compute the 3D pose T of TM in WM coordinates using equation 2.
   - Map the tool calibration information, that can be points, axes, or CAD models, into world coordinates using the rigid transformation T.
   - Relate the tool calibration information with the 3D data stored in memory to make measurements and inferences for the purpose of real-time guidance (e.g. distances and angles between surgical instrument and guides in surgical plan)
3. Communicate guidance to the surgeon by either using Augmented Reality (AR), in which case info is overlaid in image using the camera pose C and projection function f, or by animating a Virtual Reality (VR) 3D model. otherwise inform user that navigation features are not active because WM is outside the camera FOV VTIAC navigation also works for the case of multiple instruments being used in simultaneous, in which case each instrument has its own TM enabling parallel detection, identification, and estimation of 3D pose T.

Figure 5A:
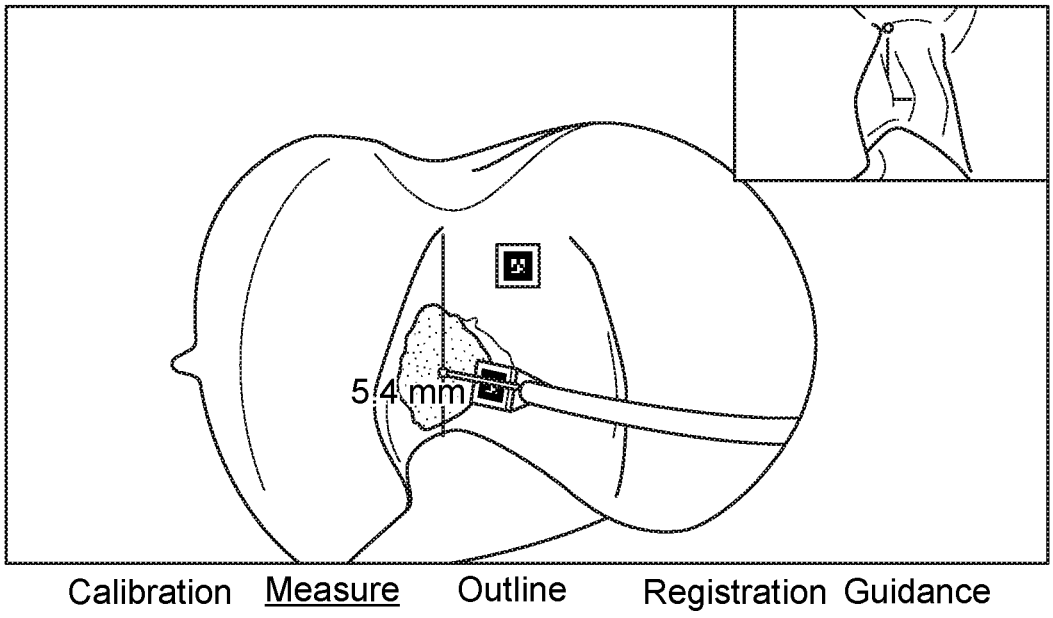
FIG. 5A is an embodiment of using the VTIAC to find the location of the femoral tunnel in ACL reconstruction. This is accomplished by measuring the length of the notch ceiling and placing the ACL footprint at ⅓ the length counting from the posterior end.
Figure 5B:
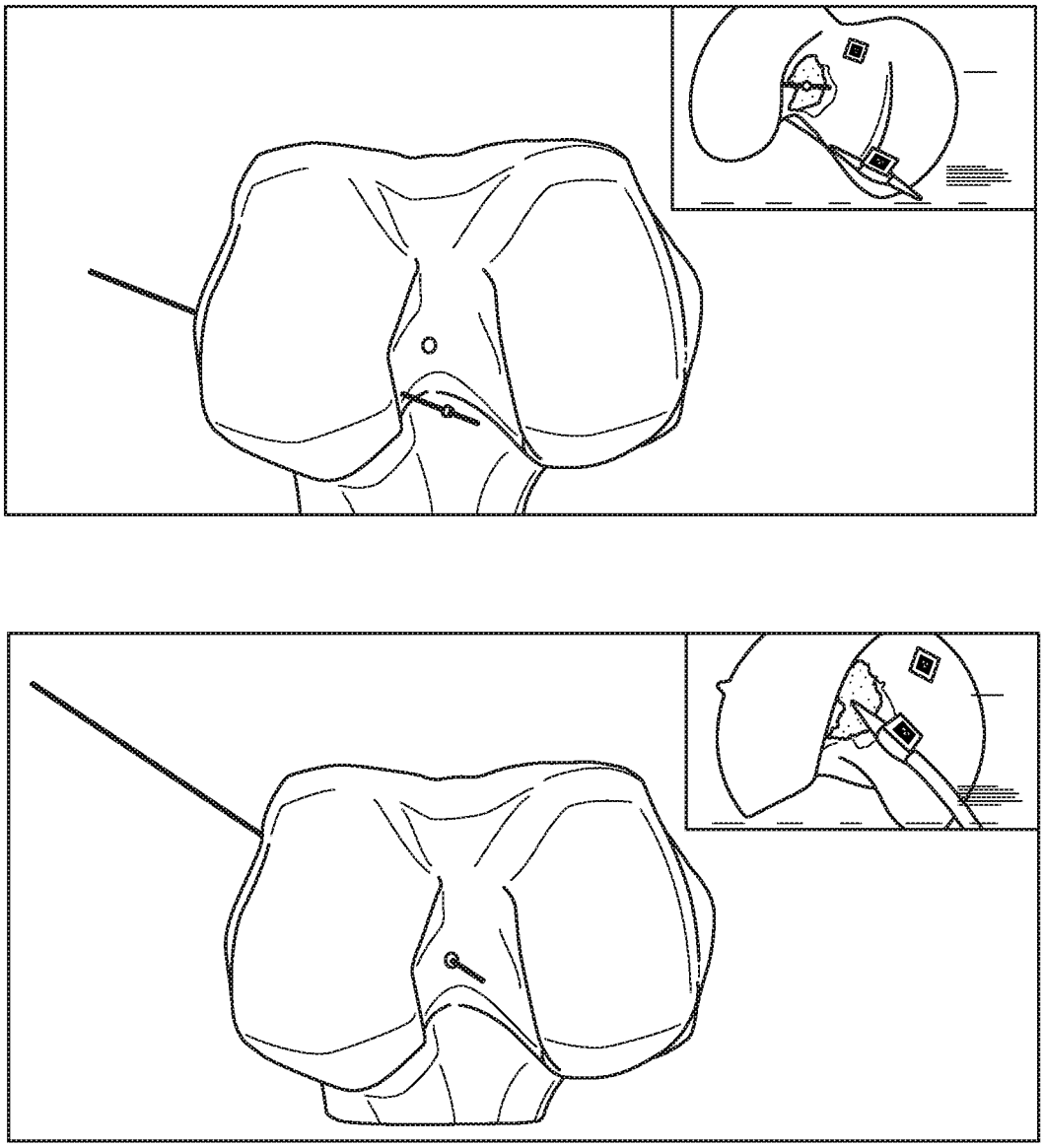
FIG. 5B is an embodiment of using the VTIAC to correctly orient the drill tool for opening the femoral tunnel in ACL reconstruction. This is accomplished by using the VR view to anticipate in real-time the position and exit point of the tunnel depending on the pose of the drill tool that is determined at each frame instant from arthroscopic video.
Figure 6A:
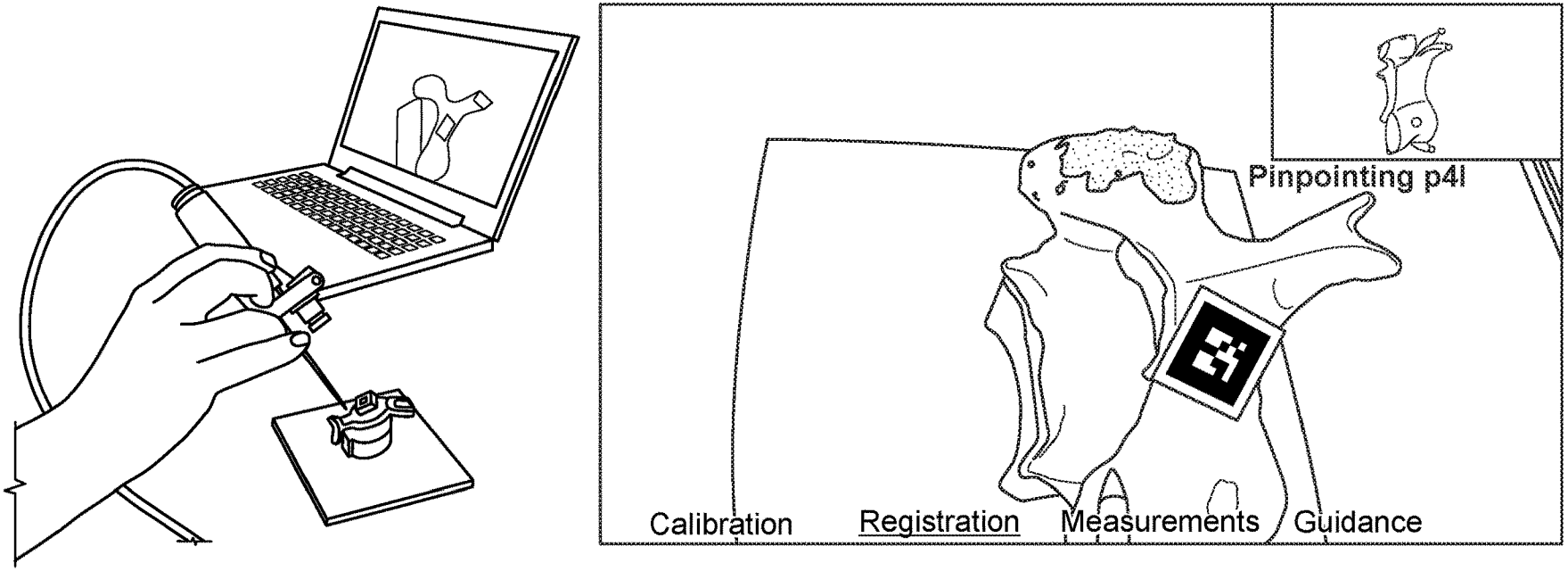
FIG. 6A is an embodiment of using the VTIAC to pinpoint points for the purpose of registration with a pre-operative model of the patient's anatomy in Placing Pedicle Screws (PPS) in spine surgery. On the top, fiducial points on the vertebra are indicated to the surgeon (green point in the upper right corner VR view) so he/she can touch the correspondent point in the patient's anatomy. The point correspondences are then used for 3D registration. In this case the touch-probe is rigidly attached to the camera (CamT) which means that only the WM is required to be visible in images
Figure 6B:
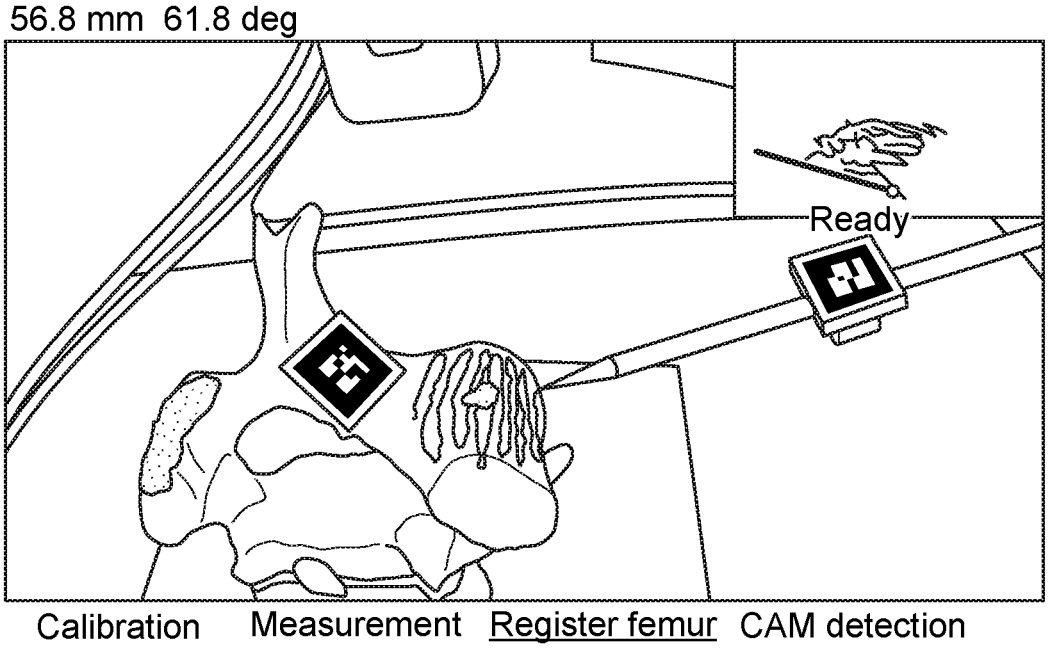
FIG. 6B is an embodiment or using VTIAC to reconstruct a sparse mesh on the surface of the vertebra for the purpose of registration with a pre-operative model during PPS. In this case the touch-probe is independent of the camera and both WM and TM must be kept in the image.
Figure 6C:
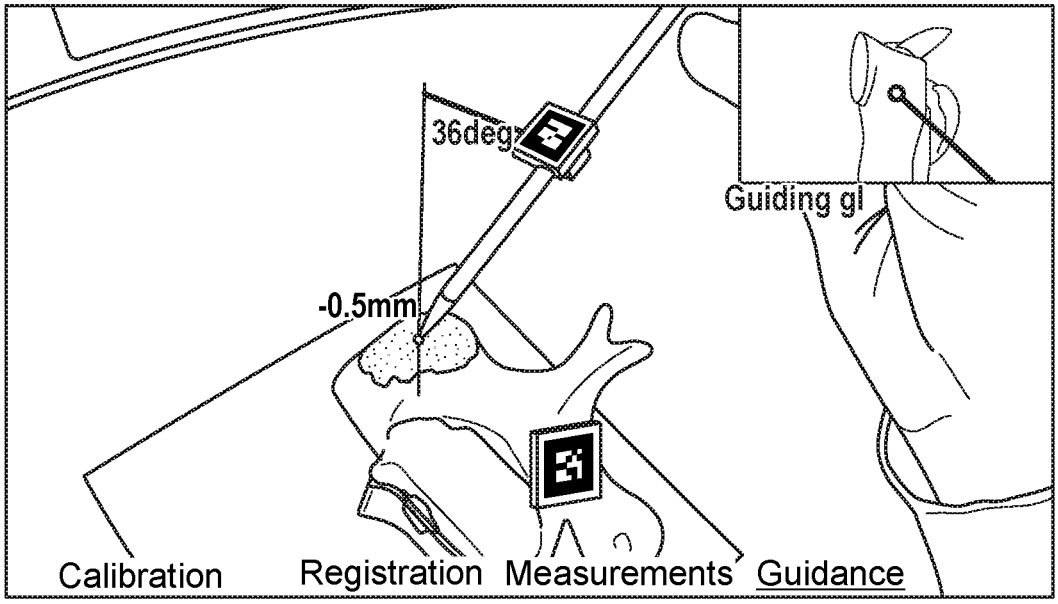
FIG. 6C is an embodiment of using the VTIAC for the measurement of the angle of the insertion in PPS in spine surgery. Virtual representation of the insertion guide is presented in the upper right corner (VR view) and the angle measurement between instrumented Kirschner wire and guide is presented in the AR view. In this case the VTIAC system can provide visual alerts when the angle of penetration is considered acceptable.
Figure 6D:
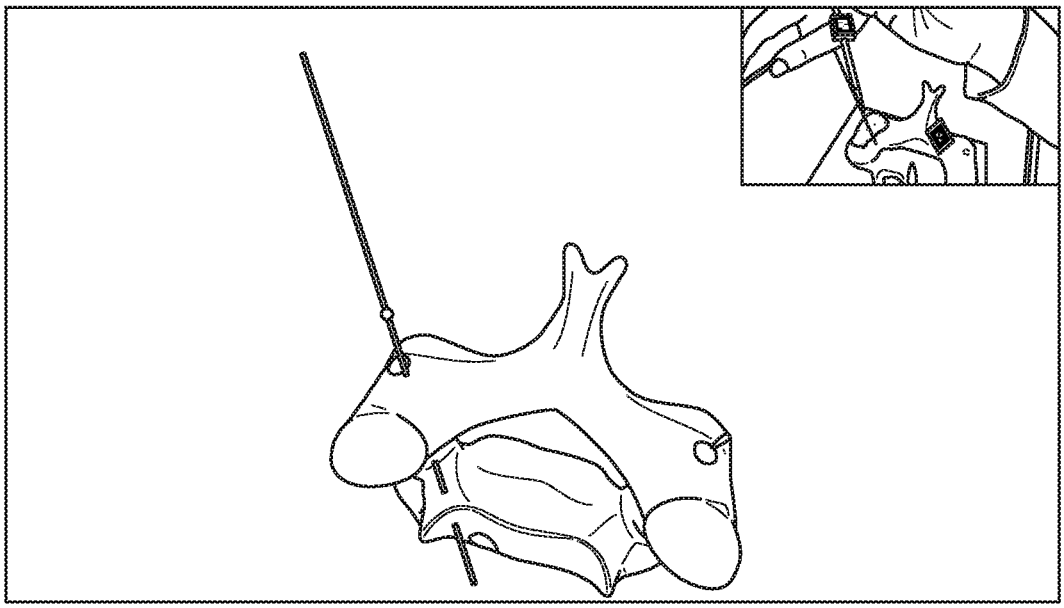
FIG. 6D is an embodiment of using the VTIAC for the visual inspection of the perforation trajectory for PPS. The virtual representation of the instrument is augmented along its axis so the surgeon can see the outcome of the perforation for each position of the tool.
Figure 6E:
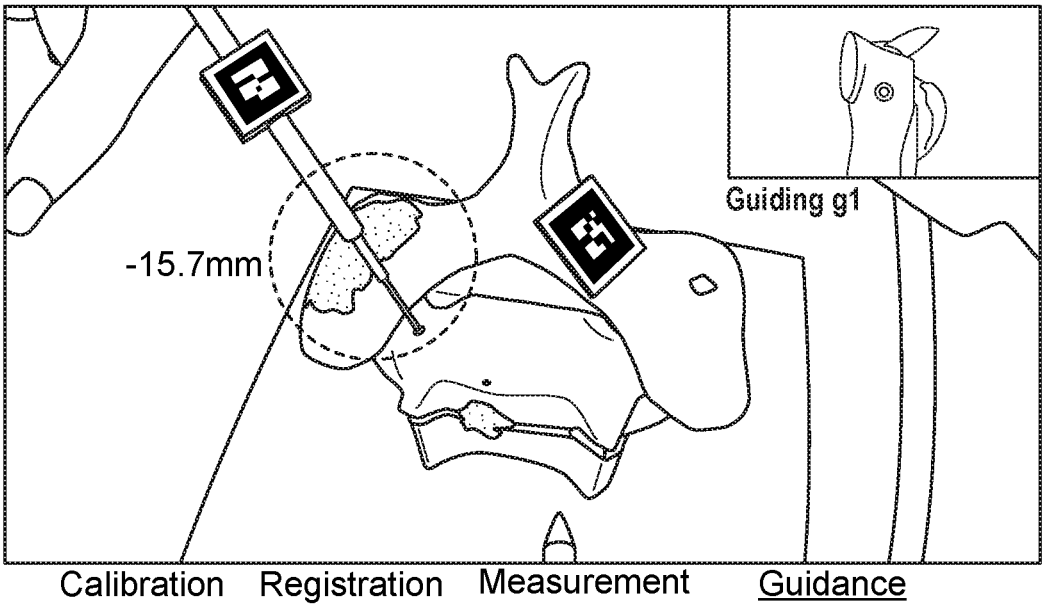
FIG. 6E is an embodiment of using the VTIAC for guiding a perforation or insertion of instrument during PPS.

The aiding features can take multiple forms depending on the particular task and/or surgical procedure. A non-exhaustive list of these features includes:

Signaling target points in the anatomy for placement or insertion, e.g. indicating the ACL footprint where the femoral tunnel should be open (FIG. 5A);

Orienting a tool by providing the angle between its axis and the desired direction of insertion or placement, e.g. overlying the angle between current and desired orientation of a Kirschner wire (FIG. 6C);

Orienting a perforation instrument by anticipating the perforation trajectory, e.g. orienting the drill direction for Pedicle Screw Placement (FIG. 6D) or orienting the drill direction in ACL reconstruction such that tunnel joins the ACL footprint with the Lateral epicondyle (FIG. 5B);

Guiding a perforation or insertion instrument by providing a view in VR where the optical axis of the virtual camera is aligned with the desired line of perforation or insertion, e.g. orienting the Kirschner wire during Pedicle Screw Placement (FIG. 6E).

Signaling a region or structure of tissue to be resected, as well as quantifying the amount of tissue to be resected, e.g. resection of cam (or pincer) femuroacetabular impingement (FIG. 4E)

Real-time measurement of distance or depth of insertion, e.g. insertion of Kirschner wire during Pedicle Screw Placement (FIG. 6E).

7. Extensions and Variations 7.1 Free-moving Camera Mounted in a Tool or Instrument:

The disclosure has considered that camera and tool or instrument are two entities with independent motions. There are situations for which it might be advantageous to assemble the camera in the tool or instrument such that the two entities become a single rigid body. The assembly, that is henceforth referred as a Camera Tool or CamT, must be calibrated such that the position of the tool tip, axis of interest, or CAD model of the tool or instrument, is known in the reference frame of the camera. Depending on the particular clinical application the camera can be mounted in a multitude of possible tools ranging from a touch-probe to an impactor for cup placement during hip arthroplasty, passing by burrs and drills. In this setup where camera and tools are physically attached, their relative 3D pose is known, and as long as the camera sees the WM, it is possible to determine the 3D pose of the tool in the global system of coordinates of WM.

FIG. 7A shows a prototype embodiment of a Camera Tool (CamT) including a small-camera mounted on a custom made hand-holder that can either be used as a free-hand camera similar (FIG. 2A), or coupled with touch-probe such that camera, holder, and probe become a single rigid body (FIG. 7A). The CamT is assumed to be calibrated meaning that the camera is calibrated and the 3D coordinates $P_C$ of the tip of the probe are known in the camera reference frame (FIG. 7B). For 3D reconstruction the surgeon uses the CamT to touch the point of interest while the WM is kept in the FOV of the camera (FIG. 7B). The acquired frame is processed as described in section 3 with the difference that step (ii) is skipped and the formula of step (iii) is replaced by $$\begin{pmatrix} P \\ 1 \end{pmatrix} = C^{-1}\begin{pmatrix} P_C \\ 1 \end{pmatrix}$$

7.2 Single-image Calibration of CamT:

The CamT described above can either be pre-calibrated from factory, or calibrated in the OR from a single image of a known grid or checkerboard pattern. In this case the surgeon acquires the calibration frame by positioning the camera such that the pattern is visible in image and the tool tip touches a particular point $P_G$ whose coordinates are known in the coordinate system of the grid (FIG. 7C). The image is used as input in the method that provides the camera intrinsic parameters k, the lens distortion $\xi$, and the rigid transformation $\hat{G}$ that maps coordinates in the grid reference frame into coordinates in the camera reference frame. The tool calibration is fully accomplished by finding the camera coordinates of the tool tip that are given by $$\begin{pmatrix} P_C \\ 1 \end{pmatrix} = \hat{G}\begin{pmatrix} P_G \\ 1 \end{pmatrix}$$

7.3 Contactless Probe using a Laser Pointer:

Section 5 discloses a method for 3D reconstruction where the surgeon uses a calibrated touch-probe to pinpoint points of interest while the camera observes both the WM and the TM of the tool. There might be situations for which touching a particular location in the anatomy is difficult or even unfeasible. Examples include situations of limited access or poor maneuverability where the touch-probe cannot reach a particular location without occluding the WM. It is now disclosed an alternative probe that can replace the conventional touch-probe in the task of performing 3D reconstruction using VTIAC, and that has the advantage of avoiding the need of physical contact.

This alternative probe, henceforth referred as contactless probe, consists in a laser pointer that emits a collimated beam of visible light. The pointer has a visual marker attached —the Tool Marker or TM—and it is assumed to be calibrated such that the position of the line $L_T$ defined by the beam is known in TM coordinates.

For reconstruction the surgeon directs the laser pointer such that the beam becomes incident on the point of interest, and uses the camera to acquire an image where WM, TM, and point of light incidence are visible. The point is reconstructed in 3D by intersecting the line $L_T$ of the beam with the back-projection line $B_x$ of the image point x where the point of light incidence is projected (FIG. 7D). Thus, the image is processed as stated in Section 5 with the difference that step (iii) is replaced by the two following steps:

1. Detect the point of light incidence x in the image and determine the corresponding back-projection line $B_x$ in camera coordinates.
2. Determine the 3D coordinates $P_T$ of the point of light incidence in the TM reference frame by making:

$$P_T = L_T A \hat{T}^{-1}(B_x)$$

where $\hat{T}^{-1}(B_x)$ denotes the back-projection line that is expressed in TM coordinates by the inverse of transformation T and A denotes the operation of intersecting two 3D lines.

7.4 Contactless Probe using a Time-of-Flight (TOF) device:

Contactless 3D reconstruction can also be accomplished using an Active Contactless Probe consisting in a Laser Rangefinder (LRF), or other equivalent device or technology relying on Time-of-Flight (ToF) principles, that is able to measure distances $\lambda$ along the direction of the beam line $L_T$. The LRF has a visual marker attached and it is assumed to be calibrated such that the origin and unit direction of measurement, that are respectively $S_T$ and $d_T$, are known in the local reference frame of TM. For 3D reconstruction the surgeon orients the LRF such that the beam becomes incident with the point of interest in the anatomy, and acquires in a synchronous manner the distance measurement $\lambda$ and an image where both WM and TM are visible. The point of interest can be outside the camera FOV (FIG. 7E). The reconstruction is accomplished using the processing steps of Section 5 with the point $P_T$ of step (iii) being given by:

$$P_T = S_T + \lambda d_T$$

7.5 Using Multiple WMs to Extend the Range of Operation:

The World Marker or WM works as a global reference, which means that it must be viewed by the camera whenever the surgeon wants to use VTIAC for reconstruction or guidance purposes. There might be situations for which keeping the WM in the camera FOV can be difficult to accomplish in practice, either because the camera has a limited FOV, or because the region to cover is simply too broad or wide. This problem is solved by using multiple markers as shown in FIG. 7F. In order to increase the working region the surgeon can fix an auxiliary visual marker (WM') on a convenient location on the surface of the anatomy, and move the camera such that both WM and WM' lie in the FOV. A frame is acquired, the method of section 4 is applied to determine the 3D pose C and C' of the two markers (FIG. 7F), and the rigid transformation W that maps coordinates in the auxiliary marker into world coordinates is $$W' = C^{-1}C'$$

Since W' enables to map information from WM into WM' and vice-versa, it suffices for the camera to see one of the markers for the reconstruction and guidance functionalities of VTIAC to be readily available. The region of operation can be further extended by placing additional markers and repeating the step above to register them in world coordinates.

7.6 Using VTIAC with a Surgical Robot

Section 6 discloses a method for using VTIAC to assist the execution of a clinical procedure where the guidance information is provided by either overlying info in the images or video (AR), or by animating a VR model of anatomy and tools. In addition, VTIAC can also be used to guide or control the action of a surgical robot (FIG. 7G).

A surgical system like the Navio® robot relies on conventional OT for determining in real-time the 3D pose between the robotized tool and patient's anatomy and/or surgical plan. VTIAC can be used as an alternative to conventional OT for providing the kinematic feedback required to control the robot in closed loop (FIG. 7G). In this case the robot end-effector, which is the tool or device at the end of the robotic arm or chain, must be instrumented with a Tool Marker and its tip, axis, or CAD model must be registered in TM coordinates. The relative 3D pose between end-effector and patient's anatomy/surgical plan is determined as described in section 6 using video acquired by a camera that simultaneously sees the WM and TM.

8. Example of Application of VTIAC for Arthroscopic Reconstruction of Anterior Cruciate Ligament (ACL) in the Knee This section discloses an embodiment of VTIAC based-navigation for Reconstruction of Anterior Cruciate Ligament (ACL) in the Knee, which can also be generalized for other arthroscopic procedures such as in the shoulder or hip.

ACL tear is a common pathology for which arthroscopy is the standard treatment (e.g., >300000 cases per year worldwide). The procedure includes replacing the torn ACL by a substitution graft that is pulled into the joint through a tunnel opened with a drill. Placing this tunnel in the correct anatomical position is crucial for the knee to fully recover its functionality. One technique is the transtibial (TT) approach that opens the tunnel in a single step by drilling from the bottom of the tibia plate till entering into the femur notch. Recent studies show that in about 39% of the cases TT fails in positioning the tunnel at the femoral end, and that much better results can be accomplished using the anteromedial (AM) approach. Unfortunately, AM is used in about 15% of the cases because it is more difficult to execute and increases the risk of critically short tunnel or blowout of the posterior femur wall. Intra-operative navigation can help in disseminating the AM approach by dramatically decreasing the execution risk and complexity. VTIAC may be applied to accomplish this intra-operative navigation by indicating the location in the femur notch where to open the tunnel (the ligament footprint) and by guiding the angular orientation of drilling.

In a possible design of the navigated procedure the surgeon starts by calibrating the arthroscopic camera and by attaching the WM in the medial side of the inter-condyle region (FIG. 5A). The WM can take the form of a button-like flat surface in the end of a wire guide that is pushed inside-out to go across the femur bone till it surfaces the patient skin. He/she then pulls the wire from the exterior for the marker to be pulled inside the joint and placed against the wall of the femur notch. It is well known that the ligament footprint should be located in the ceiling of the inter-condyle region at ⅓ the length of notch ceiling measured from its posterior end. Thus, after placement of the WM, the surgeon uses the touch-probe with the TM to pin-point the two ends of the notch ceiling such that VTIAC can measure the distance and compute the location of the footprint that is overlaid in the video using AR (FIG. 5A).

The orientation for opening the tunnel may be determined by registering a statistical model of the femur bone. For this purpose, the surgeon uses the touch probe to reconstruct the boundary contours of the inter-condyle region (FIG. 4B) or, in alternative, to obtain a sparse 3D reconstruction of the surface of the femur bone (FIG. 4C). This 3D data is fed into a suitable 3D registration algorithm that overlays the statistical model with the patient's anatomy. For opening the tunnel the surgeon uses a drill with a TM such that its position can be related in real time with the 3D data stored in memory that includes reconstruction results and the registered statistical model. One possible strategy for guided opening of the tunnel consists in the following: (i) VTIAC indicates the location of the footprint by overlaying in video using AR the point in the anatomy where drill tip should be place (the entry point), (ii) VTIAC shows in a VR environment the registered model and the current orientation of the drilling tool, where this orientation is computed in real-time from the arthroscopic video where both WM and TM can be seen, (iii) the VR environment shows the drilling direction at each frame time instant such that the surgeon can align it for the exit point to be in the Lateral epicondyle (FIG. 5B), (iv) the tunnel is open along the selected trajectory while VTIAC provides the depth from surface at each frame time instant.

9. Example of Application of VTIAC for Guiding the Placement of Pedicle Screws (PPS) During Open Surgery of Spine.

This section discloses an embodiment of VTIAC based-navigation for Placing Pedicle Screws (PPS) during spine surgery, which can also be generalized to other open procedures where a rigid surface is exposed, such as total hip replacement, total knee replacement, open shoulder surgery and implant placement in dentistry.

Although VTIAC always requires a video input, its use is not limited to arthroscopy. The framework can also be applied to open orthopedic procedures, such as knee/hip arthroplasty or spine surgery, as far as a camera is employed to observe incision and relevant anatomy. The camera can either be a generic handheld camera (FIG. 2A) or a camera mounted on a tool, such as a touch-probe like in the CamT described in section 7 (FIG. 7A).

There are several traumas and pathologies of the spine whose treatment passes by a surgery for vertebra fusion. The procedure includes placing screws in two consecutive vertebras for keeping in position a metallic rod that prevents intervertebral motion. Each screw must be carefully inserted along the vertebra pedicle otherwise it can irremediably damage the spinal medulla or a vital blood vessel. The dominant technique for Placing Pedicle Screws (PPS) is the so-called "free-hand" approach, in which the surgeon relies in his experience and knowledge to insert the screw while occasionally using fluoroscopy to confirm the correct positioning. Since this process is risky and error prone, several manufacturers developed navigation systems for PPS where a pre-operative 3D plan is overlaid with the patient anatomy in the OR using opto-tracking. In this case the surgeon uses a pre-operative model of the vertebra (e.g. CT-Scan or MRI) to specify the 3D line along which the screw must be inserted, as well as the depth of insertion. The model and the surgeon specifications are henceforth referred as the pre-operative 3D plan. This section describes how VTIAC can be applied to accomplish intra-operative navigation after planning.

In the OR, and after opening an incision for partial or total exposition of the vertebra, the surgeon starts by rigidly attaching a visual marker (WM) to the bone surface. This marker plays the role of World Marker (WM) and is placed in an arbitrary position decided by the surgeon. The next step is to overlay the pre-operative plan with patient's anatomy in the OR, which passes by reconstructing points and/or curves on the vertebra surface to be used as input in a suitable 3D registration algorithm.

One possibility is to perform the 3D registration using a set of fiducial points or landmarks in the anatomy. In this case the system indicates a succession of landmark points to be reconstructed that are pin-pointed in by the surgeon using the touch-probe (FIG. 6A). Another possibility is to use specific contours in the anatomy or a sparse 3D reconstruction of the surface in which case the surgeon randomly grasps the vertebra with the probe (FIG. 6B). The reconstruction can either be performed with the CamT, in which case the WM must be in the FOV of the camera (FIG. 6A), or with the standard touch probe with a TM attached, in which case both WM and TM must be visible in images (FIG. 6B).

After registration, the VTIAC is able to overlay the 3D pre-operative plan in the intra-operative video, as well as the tip, axis, or CAD model of the tool, whenever WM and TM are respectively in the FOV of the camera (FIG. 6C). As an alternative, and since the position of the WM in the vertebra model becomes known, the system is able to animate the motion of the tool with respect to the pre-operative model in a VR environment (FIG. 6D).

The VTIAC can then project the guidance information into the AR view, such as the angle of the tool relatively to the planned direction (FIG. 6C), or to provide a virtual extension of the tool for the surgeon to visualize the expected outcome of the chosen drill location and angle (FIG. 6D). A strategy that is particularly effective and avoids errors whenever the insertion point on the bone surface is occluded by tissue (FIG. 6E) is as follows: (i) configure the VR such that the optical axis of the virtual camera is aligned with the planned line S of insertion, (ii) move the tool tip along the occluding tissue till the tip overlays with line S that shows as a point, (iii) without moving the tip orient the tool such that its axis L shows as a point coincident with S and finally (iv) insert the tool till desired depth that is indicated by the system.

10. Application of VTIAC for Intra-operative Guidance in Other Clinical Procedures VTIAC can be applied for intra-operative navigation in several other clinical procedures. A non-exhaustive list of possibilities include:

Arthroscopic reconstruction of Posterior Cruciate Ligament (PCL): The PCL is a ligament in the knee joint that connects the posterior intercondylar area of the tibia to the medial condyle of the femur. In a similar manner to the ACL, the PCL reconstruction consists in replacing the torn ligament by a substitution graft that is pulled inside the joint through a tunnel opened with a drill. VTIAC can be applied to guide the placement of these tunnels both in tibial and femoral sides.

Arthroscopic Resection of Femuro-Acetabular Impingement (FAI): FAI occurs when the ball shaped femoral head rubs abnormally in the acetabular socket, which in about 91% of the cases is caused by an excess of bone tissue in the femur head-neck that creates a bump known as CAM impingement. The treatment is surgical and consists in removing the CAM to restore the ball shape to the femur-head. To accomplish this objective the surgeon uses a CT-scan of the femur to study the CAM position and plan the extension of resection. This plan is then mentally transposed for the execution in the OR, which is a very error prone process. VTIAC can be applied to enforce the pre-planning by overlying the annotated 3D model with the patient's femur in order to safely guide the surgeon. After model registration the CAM footprint can be overlaid in the arthroscopic video using AR techniques and the system can inform the surgeon about the quantity of the bone tissue to remove at every instant.

Arthroscopic assessment and diagnosis of confocal defects in cartilage: Confocal defects are damages in the articular cartilage that can be repaired by filling the holes or craters with a bio-compatible material. This operation often requires placing in the hole or crater an rigid support structure called scaffolder. VTIAC can be used for measuring and determining the shape of confocal defects, as well as to guide the placement of these scaffolds.

Total hip replacement (THR): THR is an open surgical procedure for replacing the hip joint by an implant. The implant consists in a cup, that replaces acetabulum in the pelvic bone, and in a stem with a sphere that replaces the femural head. VTIAC can be applied to guide the placement of the cup such that it is inserted with optimal angular orientation, as well as to define the cut plane in the femural neck to remove the head and insert the stem with sphere.

Total Knee Replacement and Unicompartmental Knee Replacement: Knee arthroplasty is an open surgical procedure for replacing total or part of the knee joint by an implant (total or unicompartmental knee replacement). VTIAC can be applied to guide the surgeon in cutting the femural condyle and placing the implant.

Shoulder Joint Replacement: This is another open surgical procedure for replacing in total or in part the shoulder joint by an implant. VTIAC can be applied in assisting the surgeon in several steps of the execution such as indicating the plane of cut to remove humeral head, or guiding the reaming of humeral shaft and/or glenoid.

Placement of dental implants in Prosthodontics: VTIAC can be applied in dental surgery for placing an implant in the maxilar bone as planned in a pre-operative Cone Beam CT (CBCT) of the patient. In this case the WM is rigidly attached to a tooth, the CBCT is overlaid with patient's anatomy by using VTIAC features for 3D reconstruction, and the system provides intra-operative guidance for inserting the implant through any of the AR and VR features that have been described in the ACL and PPS examples.

11. Additional Notes and Remarks

FIG. 8 is a schematic diagram of an embodiment of an image processing system 500 that may correspond to or may be part of a computer and/or any other computing device, such as a handheld computer, a tablet computer, a laptop computer, a portable device, a workstation, a server, a mainframe, a super computer, and/or a database. The image processing system 500 includes a processor 502, which may also be referenced as a central processor unit (CPU). The processor 502 may communicate (e.g., via a system bus) and/or provide instructions to other components within the image processing system 500, such as the input interface 504, output interface 506, and/or memory 508. In one embodiment, the processor 502 may include one or more multi-core processors and/or memory (e.g., cache memory) that function as buffers and/or storage for data. In other words, processor 502 may be part of one or more other processing components, such as application specific integrated circuits (ASICs), field-programmable gate arrays (FPGAs), and/or digital signal processors (DSPs). Although FIG. 8 illustrates that processor 502 may be a single processor, processor 502 is not so limited and instead may represent a plurality of processors. The processor 502 may be configured to implement any of the methods described herein.

FIG. 8 illustrates that memory 508 may be operatively coupled to processor 502. Memory 508 may be a non-transitory computer readable medium configured to store various types of data. For example, memory 508 may include one or more memory devices that comprise secondary storage, read-only memory (ROM), and/or random-access memory (RAM). The secondary storage is typically comprised of one or more disk drives, optical drives, solid-state drives (SSDs), and/or tape drives and is used for non-volatile storage of data. In certain instances, the secondary storage may be used to store overflow data if the allocated RAM is not large enough to hold the working data. The secondary storage may also be used to store programs that are loaded into the RAM when such programs are selected for execution. The ROM is used to store instructions and perhaps data that are read during program execution. The ROM is a non-volatile memory device that typically has a small memory capacity relative to the larger memory capacity of the secondary storage. The RAM is used to store volatile data and perhaps to store computer executable instructions.

As shown in FIG. 8, the memory 508 may be used to house the instructions for carrying out various embodiments described herein. In an embodiment, the memory 508 may comprise an image processing module 510 that may be accessed and implemented by processor 502. Alternatively, the image processing module 510 may be stored and accessed within memory embedded in processor 502 (e.g., cache memory). Specifically, the image processing module 510 may estimate the camera response function and the vignetting in case of non-uniform illumination using one or more calibration images. In one embodiment, memory 508 interfaces with a computer bus so as to communicate and/or transmit information stored in memory 508 to processor 502 during execution of software programs, such as an operating system, application programs, device drivers, and software modules that comprise program code, and/or computer executable process steps, incorporating functionality described herein, e.g., the image processing module 510. Processor 502 first loads computer executable process steps from storage, e.g., memory 510, storage medium/media, removable media drive, and/or other storage device. Processor 502 can then execute the stored process steps in order to execute the loaded computer executable process steps. Stored data, e.g., data stored by a storage device, can be accessed by processor 502 during the execution of computer executable process steps to instruct one or more components within the image processing system 500.

Programming and/or loading executable instructions onto memory 508 and processor 502 in order to transform the image processing system 500 into a non-generic particular machine or apparatus that applies VTIAC to surgical procedures is well-known in the art. Implementing instructions, real-time monitoring, and other functions by loading executable software into a computer and/or processor can be converted to a hardware implementation by well-known design rules and/or transform a general-purpose processor to a processor programmed for a specific application. For example, decisions between implementing a concept in software versus hardware may depend on a number of design choices that include stability of the design and numbers of units to be produced and issues involved in translating from the software domain to the hardware domain. Often a design may be developed and tested in a software form and subsequently transformed, by well-known design rules, to an equivalent hardware implementation in an ASIC or application specific hardware that hardwires the instructions of the software. In the same manner as a machine controlled by a new ASIC is a particular machine or apparatus, likewise a computer that has been programmed and/or loaded with executable instructions may be viewed as a non-generic particular machine or apparatus.

In addition, FIG. 8 illustrates that the processor 502 may be operatively coupled to an input interface 504 configured to obtain one or more images and output interface 506 configured to output and/or display the images. The input interface 504 may be configured to obtain one or more images via electrical, optical, and/or wireless connections using one or more communication protocols. In one embodiment, the input interface 502 may be a network interface that comprises a plurality of ports configured to receive and/or transmit data via a network. In particular, the network may transmit image data via wired links, wireless link, and/or logical links. Other examples of the input interface 504 may include but are not limited to a keyboard, universal serial bus (USB) interfaces, CD-ROMs, DVD-ROMs and/or graphical input devices (e.g., onscreen and/or virtual keyboards). The output interface 506 may be an interface used to display information in a readable format for a user and/or used to transmit information to a separate apparatus or machine. Examples include, but are not limited to, a graphic display (e.g., monitors and display screens), a user interface, an interface used to connect to a printing device configured to produce hard-copies of the generated results, and output ports used to connect to a network and/or another computing device. Image processing system 500 may also include computing components not explicitly shown in FIG. 8, but well-known in the art, such as one or more power supplies, network interface(s), audio interfaces, displays, and circuitry used to connect the processor 502, input interfaces 504, output interface 506, and memory 508.

As shown in FIG. 9, internal architecture 900 of a computing device(s), computing system, computing platform and the like includes one or more processing units, processors, or processing cores, (also referred to herein as CPUs) 912, which interface with at least one computer bus 902. Also interfacing with computer bus 902 are computer-readable medium, or media, 906, network interface 914, memory 904, e.g., random access memory (RAM), run-time transient memory, read only memory (ROM), media disk drive interface 920 as an interface for a drive that can read and/or write to media including removable media such as floppy, CD-ROM, DVD, media, display interface 910 as interface for a monitor or other display device, keyboard interface 916 as interface for a keyboard, pointing device interface 918 as an interface for a mouse or other pointing device, and miscellaneous other interfaces 922 not shown individually, such as parallel and serial port interfaces and a universal serial bus (USB) interface.

Memory 904 interfaces with computer bus 902 so as to provide information stored in memory 904 to CPU 912 during execution of software programs such as an operating system, application programs, device drivers, and software modules that comprise program code, and/or computer executable process steps, incorporating functionality described herein, e.g., one or more of process flows described herein. CPU 912 first loads computer executable process steps from storage, e.g., memory 904, computer readable storage medium/media 906, removable media drive, and/or other storage device. CPU 912 can then execute the stored process steps in order to execute the loaded computer-executable process steps. Stored data, e.g., data stored by a storage device, can be accessed by CPU 912 during the execution of computer-executable process steps.

Persistent storage, e.g., medium/media 906, can be used to store an operating system and one or more application programs. Persistent storage can also be used to store device drivers, such as one or more of a digital camera driver, monitor driver, printer driver, scanner driver, or other device drivers, web pages, content files, playlists and other files. Persistent storage can further include program modules and data files used to implement one or more embodiments of the present disclosure.

A network link typically provides information communication using transmission media through one or more networks to other devices that use or process the information. For example, the network link may provide a connection through a local network to a host computer or to equipment operated by a Network or Internet Service Provider (ISP). ISP equipment in turn provides data communication services through the public, worldwide packet-switching communication network of networks now commonly referred to as the Internet.

A computer called a server host connected to the Internet hosts a process that provides a service in response to information received over the Internet. For example, server host hosts a process that provides information representing video data for presentation at display 910. It is contemplated that the components of system 900 can be deployed in various configurations within other computer systems, e.g., host and server.

At least some embodiments of the present disclosure are related to the use of computer system 900 for implementing some or all of the techniques described herein. According to one embodiment, those techniques are performed by computer system 900 in response to processing unit 912 executing one or more sequences of one or more processor instructions contained in memory 904. Such instructions, also called computer instructions, software and program code, may be read into memory 904 from another computer-readable medium 906 such as storage device or network link. Execution of the sequences of instructions contained in memory 904 causes processing unit 912 to perform one or more of the method steps described herein. In alternative embodiments, hardware, such as ASIC, may be used in place of or in combination with software. Thus, embodiments of the present disclosure are not limited to any specific combination of hardware and software, unless otherwise explicitly stated herein.

The signals transmitted over network link and other networks through communications interface, carry information to and from computer system 900. Computer system 900 can send and receive information, including program code, through the networks, among others, through network link and communications interface. In an example using the Internet, a server host transmits program code for a particular application, requested by a message sent from computer, through Internet, ISP equipment, local network and communications interface. The received code may be executed by processor 902 as it is received, or may be stored in memory 904 or in storage device or other non-volatile storage for later execution, or both.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. A module, or software components of a module, may be stored on a computer readable medium for execution by a processor. Modules may be integral to one or more servers, or be loaded and executed by one or more servers. One or more modules may be grouped into an engine or an application.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The use of the term "about" means ±10% of the subsequent number, unless otherwise stated.

Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

While several embodiments have been provided in the present disclosure, it may be understood that the disclosed embodiments might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, the various embodiments described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

In closing, it should be noted that the discussion of any reference is not an admission that it is prior art to the presently disclosed embodiments, especially any reference that may have a publication date after the priority date of this application. At the same time, each and every claim below is hereby incorporated into this detailed description or specification as additional embodiments of the presently disclosed embodiments.

The invention claimed is:

[1. A system for video based computer-aided surgery and diagnosis in anatomical regions of a patient comprising rigid, non-deformable anatomical parts or tissues comprising:

(i). a free-moving camera that is meant to acquire intra-operative images and video of an operating field, articular joint or anatomical cavity;

(ii). a visual marker, referred to as a World Marker or WM, which is an object that can be rigidly attached to a surface, and that comprises at least one planar facet with a known pattern having a system of coordinates that defines a global or world system of coordinates;

(iii). a touch-probe that is a tool or instrument comprising a handgrip and a tip, and that has at least one visual marker, referred to as a Tool Marker or TM, comprising at least one planar facet with a known pattern that defines a local system of coordinates where a position of the tip $PT_T$ is known;

(iv). one or more surgical instruments for surgical execution, where each surgical instrument has at least one visual marker, also referred to as a Tool Marker or TM, comprising at least one planar facet with a known pattern that defines a local system of coordinates in which a position of relevant points and parts in the instrument are known; and (v). an image processing system, that may correspond to or may be part of a computer and/or any other computing device, that receives as input images and video acquired by the camera (i), as well as commands that may be entered by a button panel, keyboard, camera buttons, foot switch and/or any other input interface, and that outputs processing results and guidance information to a display;

wherein the system is configured to execute steps comprising:

(vi). attachment of the WM of (ii) in an arbitrary location in a surface of a rigid anatomical part of interest, such that the WM of (ii) and the rigid anatomical part of interest do not move one with respect to the other;

(vii). 3D reconstruction of points in the surface of the rigid anatomical part of interest by using the touch-probe of (iii) to pin-point the points in the surface while keeping both the WM and the TM of the probe in a Field-of-View or FOV of the camera of (i) for determining the location of the touch-probe in the world system of coordinates to create 3D reconstruction results;

(viii). use the 3D reconstruction results to perform measurements, make inferences, or overlay a surgical plan with an anatomical region of the patient, in which case a 3D registration method may be used for determining a transformation that maps local coordinates in a surgical plan into world coordinates in the WM attached to the anatomical part of interest; and (ix). assisted execution of a clinical procedure by using the surgical instruments of (iv) while keeping both WM and TMs of the surgical instruments in the FOV of the camera of (i) such that the surgical instruments can be located in world coordinates and real-time guidance can be provided by relating surgical instrument locations in world coordinates with the 3D reconstruction results and/or overlaid surgical plan;

where the camera in (i) is calibrated such that image points u expressed in pixel coordinates are mapped into image points x expressed in metric units according to $$x=f^{-1}(u;\ k,\xi)$$

with $f^{-1}$ being an inverse of a projection function f and where k and $\xi$ stand respectively for camera intrinsic and distortion parameters.]

[2. The system of claim 1 wherein the camera is pre-calibrated from a factory or is calibrated in an Operating Room (OR) by acquiring a single image of a known calibration grid or checkerboard pattern that allows estimating intrinsic parameters k, a distortion $\xi$ and a rigid transformation $\hat{G}$ that relates coordinates of the calibration grid and coordinates of the camera.]

[3. The system of claim 2 wherein the instrinsic parameters k and the distortion $\xi$ are automatically updated during operation to compensate for one or more of differences in medium, rotation of lens scope with respect to camera-head, and variations in zoom.]

[4. The system of claim 1 wherein the WM in (ii) comprises, depending on a targeted clinical application and a chosen method (vi) of attachment, one or more of a screw-like object with a flat head or facet, a nail-like object with a flat head or facet to be fixed by pressure, a needle like object with a flat lateral facet for trans-dermic insertion into the joint or cavity, or a flat button-like object that is pulled inside a joint or cavity by a thread or guide.]

[5. The system of claim 1 wherein each of the (ii) World Marker, (iii) touch probe, and (iv) surgical instruments are manufactured in metal or plastic, and wherein the Tool Markers can be assembled, secured, printed, or engraved.]

[6. The system of claim 1 wherein the planar pattern of the visual marker in (ii), (iii), and (iv) comprises any pattern that can be detected and uniquely identified using image processing techniques, and that has recognizable fiducial points for estimating a plane-to-image homography that, given a camera calibration, can be factorized in a rotation r and translation t that map points p in the coordinate system of the pattern into points x in the metric coordinate system of the camera.]

[7. The system of claim 6, wherein an initial 3D pose estimation r, t is further refined by determining increments in rotation $\xi_R$ and translation $\xi_t$ that minimize the following photo-geometric error $$\epsilon_i = \sum_{u\in N_i} [I(w(u;\ r_0+\delta_R,\ t_0+\delta_t)) - T(u)]^2$$

where T(u) is the pattern template, I(u) is a current frame, $N_i$ is a pattern region, and w is an image warping function given by the function composition $$w(u;\ r,\ t)=f(x;\ k,\ \xi)\circ h(x;\ r,\ t)\circ f^{-1}(u;\ k',\ \xi')$$

with f being the projection function and h denoting a homography map that depends on a relative 3D pose r, t.]

[8. The system of claim 7 wherein the minimization of the photo-geometric error $\varepsilon_I$ is performed using direct composition, inverse composition, or efficient second order minimization, and wherein formulation of the photo-geometric error takes into account variable illumination conditions.]

[9. The system of claim 1 wherein a calibration of the touch-probe of (iii) for finding the coordinates $P_T$ of its tip is performed in an operating room (OR) in parallel with a camera calibration, in which case the tool tip is placed in a point in a calibration grid with known coordinates $P_G$ and a single calibration image shows both the calibration grid and the TM of the touch-probe such that $P_T$ can be determined by $$\begin{pmatrix} P_T \\ 1 \end{pmatrix} = \hat{T}^{-1}\hat{G}\begin{pmatrix} P_G \\ 1 \end{pmatrix}$$

with $\hat{T}^{-1}$ denoting an inverse of a rigid transformation $\hat{T}$ that encodes a 3D pose r, t of the TM in camera coordinates that is determined from image information.]

[10. The system of claim 1 wherein an arbitrary point P is reconstructed in global or world coordinates by acquiring an image as described in (vii) that undergoes the following processing steps:

detect, identify, and estimate a 3D pose C of the WM in camera coordinates;

detect, identify, and estimate a 3D pose $\hat{T}$ of the TM in camera coordinates;

reconstruct a point P that is in contact with the tip of the touch-probe by making $$\begin{pmatrix} P \\ 1 \end{pmatrix} = C^{-1}\hat{T}\begin{pmatrix} P_T \\ 1 \end{pmatrix};$$

and store 3D coordinates of point P in memory.]

[11. The system of claim 10, wherein the system is further configured to execute steps comprising:

reconstructing a contour or a sparse mesh of a surface region, in which case the touch-probe is respectively used to outline the contour or randomly grasp the surface region, while the camera acquires a continuous sequence of images as described in (vii), and the processing steps are executed for each frame of the sequence.]

[12. The system of claim 11 wherein the 3D reconstruction results are used for measuring distances, areas, or volumes, inferring the shape of curves, regions, or surfaces, or overlying a surgical plan with the patient's anatomy in which case a suitable 3D registration method may be employed.]

[13. The system of claim 12 wherein 3D data is stored in memory, the 3D data including the reconstruction results of (vii) and the measurements, inferences and surgical plan of (vii), wherein the 3D data is overlaid in the video whenever the WM is in the FOV of the camera, in which case each image undergoes the following processing steps in real-time:

detect, identify, and estimate the 3D pose C of the WM in camera coordinates;

map the 3D data from world coordinates into camera coordinates using C; and project the 3D data into the image using the camera calibration and projection function f (augmented reality).]

[14. The system of claim 1 wherein the system is configured to, for each of the one or more surgical instruments of (iv), calibrate the surgical instrument by determining in TM coordinates the position of a point, axis, or CAD model of the surgical instrument that can be either performed in factory at manufacturing time, or in the operating room (OR) before starting the clinical procedure, in which case the camera of (i) and the touch-probe of (iii) are used to reconstruct 3D points in the surgical instrument where the role of the WM is replaced by the TM of the instrument for the reconstruction results to be expressed in a local reference frame of the instrument.]

[15. The system of claim 1 wherein the assisted execution of the clinical procedure is accomplished by acquiring continuous video according to (ix), the video comprising a plurality of images, with each consecutive image undergoing the following processing steps in real-time:

a. detect, identify, and estimate a 3D pose C of the WM in camera coordinates;

b. detect, identify, and estimate a 3D pose $\hat{T}$ of the TM of each of the one or more surgical instruments in camera coordinates;

c. compute the 3D pose T of TM in WM coordinates using the following equation:

$$T=C^{-1}\hat{T}$$

d. map the information of surgical instrument calibration, that can be points, axes, or CAD models, into world coordinates using the rigid transformation T;

e. relate the surgical instrument calibration information with 3D data stored in memory to make measurements and inferences for the purpose of real-time guidance; and f. display aiding features either by using Augmented Reality (AR), in which case guidance information is overlaid in image, or by animating a Virtual Reality (VR) 3D model.]

[16. The system of claim 15 wherein the aiding features can take multiple forms including highlighting points, regions or structures in anatomy, measuring distance, thickness or depth, measuring angles between axes or between an axis and a plane, anticipating trajectories of insertion, penetration or cut, and delimiting regions or structures in anatomy for resection or dissection.]

[17. The system of claim 15 wherein multiple surgical instruments are used simultaneously, in which case steps b to e are run in parallel for each instrument whose TM is visible in the image.]

[18. The system of claim 15 wherein the one or more surgical instruments of (iv) comprises, or is rigidly attached to, a robot end-effector and the guidance or aided execution of (ix) includes sending commands to the robot for the purpose of controlling the motion and/or action of the one or more surgical instruments.]

[19. The system of claim 1, wherein WM is a primary marker, wherein one or more secondary markers WM' are attached to the surface of the rigid anatomical part of interest as described in (vi) for the purpose of increasing a working area or region of operation, in which case all systems functionalities of 3D reconstruction and aided execution are readily available whenever one of the secondary markers WM' is visible in image and the transformation W, that maps WM' coordinates into global or world coordinates in a reference frame of the primary marker WM, is known.]

[20. The system of claim 19 wherein the transformation W is determined by acquiring an image where both primary and secondary markers are visible, in which case the transformation is given by $$W'=C^{-1}C',$$

with C and C' being respectively the 3D pose of WM and WM' that are computed from image information.]

[21. The system of claim 1 wherein the camera of (i) is assembled with a tool such that the camera and the tool become a single rigid body with the position of relevant points or parts of the tool being known in camera coordinates, in which case the location of these points or parts can be determined in global or world coordinates whenever the WM of (ii) is in the FOV of the camera and its 3D pose C can be estimated from image information.]

[22. The system of claim 21 wherein the camera is assembled with a touch-probe to create an ensemble to replace (iii) in the 3D reconstruction step of (vii), in which case the ensemble is used to pin-point an arbitrary point P while keeping the WM in the FOV of the camera to determine its world coordinates by making $$\begin{pmatrix} P \\ 1 \end{pmatrix} = C^{-1}\begin{pmatrix} P_C \\ 1 \end{pmatrix},$$

with $P_c$ being the position of the probe tip in camera coordinates and $C^{-1}$ a 3D pose of the camera in WM coordinates that is estimated from image information.]

[23. The system of claim 22 wherein a calibration of the ensemble for finding coordinates $P_c$ of the touch-probe tip in camera coordinates is performed in an operating room (OR) in parallel with a camera calibration, in which case the tool or instrument tip is placed in a point in a calibration grid with known coordinates $P_G$, and a single calibration image shows the calibration grid such that $P_c$ can be determined by $$\begin{pmatrix} P_C \\ 1 \end{pmatrix} = \hat{G}\begin{pmatrix} P_G \\ 1 \end{pmatrix}$$

with $\hat{G}$ denoting a rigid transformation that encodes a 3D pose r, t of a pattern of the calibration grid in camera coordinates t.]

[24. The system of claim 1 wherein the touch probe of (iii) comprises a laser pointer with a visual marker (TM) attached, for which a line $L_T$ defined by a laser beam is known in a reference frame of the visual marker (TM), and wherein the 3D reconstruction step of (vii) is performed in a contactless manner by acquiring an image where WM, TM and a point of incidence of the laser beam with the surface are simultaneously visible, and by processing this image with point $P_T$ being given by $$P_T = L_T \Lambda \hat{T}^{-1}(B_x)$$

with Λ denoting the operation of line intersection in 3D, $B_x$ being the back-projection line of the point of incidence that is detected in the image, and $\hat{T}^{-1}(B_x)$ denoting the line Bx expressed in the local system of coordinates of the visual marker (TM).]

[25. The system of claim 1 wherein the touch probe of (iii) comprises a time-of-flight device that has a visual marker TM attached and that measures distances λ from an origin $S_T$ along a beam direction $d_T$ that are known in a reference frame of the visual marker TM, and wherein the 3D reconstruction is performed in a contactless manner by acquiring an image as described in (vii) that undergoes the processing steps with the point $P_T$ being given by $$P_T = S_T + \lambda d_T.$$

]

[26. The system of claim 1 wherein the visual markers of (ii), (iii) and (iv) have multiple planar facets with distinct patterns where the location of each pattern is known in a common coordinate system of the markers for the purpose of extending a range of viewing positions and orientations from which the marker can be observed.]

[27. The system of claim 1 wherein the visual markers of (ii), (iii) and (iv) are non-planar, in which case each marker should comprise n≥3 recognizable points with known coordinates in its local reference frame for enabling 3D pose estimation from images using a Perspective-n-Point algorithm.]

[28. The system of claim 1 that is used for computer assisted execution of arthroscopic procedures including anterior and/or posterior cruciate ligament reconstruction, resection of femuro-acetabular impingement, or diagnosis and repair of confocal defects in cartilage, in which case the free-moving camera is the arthroscopic camera used for visualizing the articular joint.]

[29. The system of claim 1 that is used for computer assisted execution of open surgical procedures in orthopedics, including total hip replacement, total knee replacement, unicompartmental knee replacement, shoulder joint replacement, and pedicle-screw placement, in which case a camera is used to observe the operating field.]

[30. The system of claim 1 that is used for computer assisted execution of prosthodontic procedures including placement of dental implants.]

[31. A method for computer-aided execution of surgery and diagnosis in anatomical regions comprising rigid, non-deformable parts or tissues, the method comprising:

(i) attaching a visual marker, referred to as the World Marker or WM, in an arbitrary location in the surface of the rigid anatomical part of interest, the visual marker comprising at least one planar facet with a known pattern whose system of coordinates defines a global or world system of coordinates;

(ii) acquiring, by a free-moving camera, intra-operative images and video of an operating field, articular joint, or anatomical cavity;

(iii) using a touch-probe, which is a tool or instrument comprising a handgrip and a tip, and that has at least one visual marker, referred to as Tool Marker or TM, comprising at least one planar facet with a known pattern that defines a local system of coordinates where a position of the tip PT is known, for pin-pointing points and/or outlining curves in the surface of the rigid anatomical part, while keeping both WM and TM of the probe in the Field-of-View or FOV of the camera to be visible in the acquired images and video;

(iv) receiving, by an image processing system that may correspond to, or may be part of, a computer and/or any other computing device, the images and video acquired in (iii), which are processed for determining the location of the touch-probe and reconstructing in 3D the pin-pointed points and/or outlined curves that are stored in memory in global or world coordinates;

(v) using the 3D reconstruction results to perform measurements, make inferences, or overlay a surgical plan with the patient's anatomy, in which case a 3D registration method may be used for determining the transformation that maps local coordinates in a surgical plan into world coordinates in the WM attached to anatomy of interest;

(vi) performing the surgical procedure with the required instruments, where each instrument has at least one visual marker, also referred to as Tool Marker or TM, comprising at least one planar facet with a known pattern that defines a local system of coordinates in which the position of relevant points and parts in the instrument are known, while keeping both WM and TMs of the instruments in the FOV of the camera to be visible in the acquired images and video;

(vii) receiving, by the image processing system, the images and video acquired in (vi), that are processed such that instruments can be located in world coordinates and real-time guidance can be provided by relating these locations with 3D reconstructions results and/or overlaid surgical plan; and (viii) outputting, by the image processing system, processing results and guidance information to a display, by either overlaying information in the input video using augmented reality (AR) techniques, or by animating models in a virtual reality (VR) environment;

where the camera is calibrated such that image points u expressed in pixel coordinates are mapped into image points x expressed in metric units according to $$x = f^{-1}(u; k, \xi)$$

with $f^{-1}$ being the inverse of a projection function f and where k and ξ stand respectively for camera intrinsic and distortion parameters.]

[32. A system for video based computer-aided surgery and diagnosis in anatomical regions of a patient comprising rigid, non-deformable anatomical parts or tissues comprising:

(i). a free-moving camera that is meant to acquire intra-operative images and video of an operating field, articular joint or anatomical cavity;

(ii). a visual marker, referred to as a World Marker or WM, which is an object that can be rigidly attached to a surface, and that comprises at least one planar facet with a known pattern having a system of coordinates that defines a global or world system of coordinates;

(iii). a touch-probe that is a tool or instrument comprising a handgrip and a tip, and that has at least one visual marker, referred to as a Tool Marker or TM, comprising at least one planar facet with a known pattern that defines a local system of coordinates where a position of the tip $P_T$ is known;

(iv). one or more surgical instruments for surgical execution, where each surgical instrument has at least one visual marker, also referred to as a Tool Marker or TM, comprising at least one planar facet with a known pattern that defines a local system of coordinates in which a position of relevant points and parts in the instrument are known; and (v). an image processing system, that may correspond to or may be part of a computer and/or any other computing device, that receives as input images and video acquired by the camera (i), as well as commands that may be entered by a button panel, keyboard, camera buttons, foot switch and/or any other input interface, and that outputs processing results and guidance information to a display;

wherein the system is configured to execute steps comprising:

(vi). attachment of the WM of (ii) in an arbitrary location in a surface of a rigid anatomical part of interest, such that the WM of (ii) and the rigid anatomical part of interest do not move one with respect to the other;

(vii). 3D reconstruction of points in the surface of the rigid anatomical part of interest by using the touch-probe of (iii) to pin-point the points in the surface while keeping both the WM and the TM of the probe in a Field-of-View or FOV of the camera of (i) for determining the location of the touch-probe in the world system of coordinates to create 3D reconstruction results;

(viii). use the 3D reconstruction results to perform measurements, make inferences, or overlay a surgical plan with an anatomical region of the patient, in which case a 3D registration method may be used for determining a transformation that maps local coordinates in a surgical plan into world coordinates in the WM attached to the anatomical part of interest; and (ix). assisted execution of a clinical procedure by using the surgical instruments of (iv) while keeping both WM and TMs of the surgical instruments in the FOV of the camera of (i) such that the surgical instruments can be located in world coordinates and real-time guidance can be provided by relating surgical instrument locations in world coordinates;

wherein an arbitrary point P is reconstructed in global or world coordinates by acquiring an image as described in (vii) that undergoes the following processing steps:

detect, identify, and estimate a 3D pose C of the WM in camera coordinates;

detect, identify, and estimate a 3D pose $\hat{T}$ of the TM in camera coordinates;

reconstruct a point P that is in contact with the tip of the touch-probe by making $$\begin{pmatrix} P \\ 1 \end{pmatrix} = C^{-1}\hat{T}\begin{pmatrix} P_T \\ 1 \end{pmatrix};$$

and store 3D coordinates of point P in a memory.]

[33. A system for video based computer-aided surgery and diagnosis in anatomical regions of a patient comprising rigid, non-deformable anatomical parts or tissues comprising:

(i). a free-moving camera that is meant to acquire intra-operative images and video of an operating field, articular joint or anatomical cavity;

(ii). a visual marker, referred to as a World Marker or WM, which is an object that can be rigidly attached to a surface, and that comprises at least one planar facet with a known pattern having a system of coordinates that defines a global or world system of coordinates;

(iii). a touch-probe that is a tool or instrument comprising a handgrip and a tip, and that has at least one visual marker, referred to as a Tool Marker or TM, comprising at least one planar facet with a known pattern that defines a local system of coordinates where a position of the tip $P_T$ is known;

(iv). one or more surgical instruments for surgical execution, where each surgical instrument has at least one visual marker, also referred to as a Tool Marker or TM, comprising at least one planar facet with a known pattern that defines a local system of coordinates in which a position of relevant points and parts in the instrument are known; and (v). an image processing system, that may correspond to or may be part of a computer and/or any other computing device, that receives as input images and video acquired by the camera (i), as well as commands that may be entered by a button panel, keyboard, camera buttons, foot switch and/or any other input interface, and that outputs processing results and guidance information to a display;

wherein the system is configured to execute steps comprising:

(vi). attachment of the WM of (ii) in an arbitrary location in a surface of a rigid anatomical part of interest, such that the WM of (ii) and the rigid anatomical part of interest do not move one with respect to the other;

(vii). 3D reconstruction of points in the surface of the rigid anatomical part of interest by using the touch-probe of (iii) to pin-point the points in the surface while keeping both the WM and the TM of the probe in a Field-of-View or FOV of the camera of (i) for determining the location of the touch-probe in the world system of coordinates to create 3D reconstruction results;

(viii). use the 3D reconstruction results to perform measurements, make inferences, or overlay a surgical plan with an anatomical region of the patient, in which case a 3D registration method may be used for determining a transformation that maps local coordinates in a surgical plan into world coordinates in the WM attached to the anatomical part of interest; and (ix).assisted execution of a clinical procedure by using the surgical instruments of (iv) while keeping both WM and TMs of the surgical instruments in the FOV of the camera of (i) such that the surgical instruments can be located in world coordinates and real-time guidance can be provided by relating surgical instrument locations in world coordinates;

wherein the assisted execution of the clinical procedure is accomplished by acquiring continuous video according to (ix), the video comprising a plurality of images, with each consecutive image undergoing the following processing steps in real-time:

a. detect, identify, and estimate a 3D pose C of the WM in camera coordinates;

b. detect, identify, and estimate a 3D pose $\hat{T}$ of the TM of each of the one or more surgical instruments in camera coordinates;

c. compute the 3D pose T of TM in WM coordinates using the following equation:

$$T = C^{-1}\hat{T}$$

d. map the information of surgical instrument calibration, that can be points, axes, or CAD models, into world coordinates using the rigid transformation T;

e. relate the surgical instrument calibration information with 3D data stored in memory to make measurements and inferences for the purpose of real-time guidance; and f. display aiding features either by using Augmented Reality (AR), in which case guidance information is overlaid in image or by animating a Virtual Reality (VR) 3D model.]

*34. An image processing system comprising:*

*one or more storage devices storing processor-executable instructions, and*

*one or more processors configured to execute the instructions to cause the image processing system to perform operations including:*

*receiving one or more images and/or frames of video, wherein the one or more images and/or frames of video depict (i) a first marker that does not move with respect to an anatomical part of a patient, and (ii) a second marker coupled to a contactless probe;*

*receiving a 3D reconstruction of a plurality of points of the anatomical part of the patient in a first coordinate system defined using the first marker, the plurality of points having been illuminated by light emitted by the contactless probe; and*

*outputting information derived from the 3D reconstruction for display;*

*wherein the one or more images and/or frames of video are captured by a camera,*

*wherein the camera is calibrated such that one or more image points u expressed in pixel coordinates are mapped into one or more image points x expressed in coordinates of the camera according to an inverse projection function, wherein the inverse projection function depends on one or more camera intrinsic and/or distortion parameters.*

*35. The image processing system of claim 34, wherein the contactless probe comprises a laser pointer or a laser rangefinder.*

*36. The image processing system of claim 34, wherein the contactless probe comprises a light source configured to emit a beam of light.*

*37. The image processing system of claim 36, wherein the beam of light is collimated.*

*38. The image processing system of claim 34, wherein the camera is configured to move freely.*

*39. An image processing system comprising:*

*one or more storage devices storing processor-executable instructions, and*

*one or more processors configured to execute the instructions to cause the image processing system to perform operations including:*

*receiving one or more images and/or frames of video, wherein the one or more images and/or frames of video depict (i) a first marker that does not move with respect to an anatomical part of a patient, and (ii) a second marker coupled to a contactless probe;*

*receiving a 3D reconstruction of a plurality of points of the anatomical part of the patient in a first coordinate system defined using the first marker, the plurality of points having been illuminated by light emitted by the contactless probe; and*

*outputting information derived from the 3D reconstruction for display;*

*wherein the one or more images and/or frames of video are captured by a camera,*

*wherein the camera is calibrated such that one or moe image points u expressed in pixel coordinates are mapped into one or more image points x expressed in metric units according to*

$$x = f^{-1}(u; k, \xi)$$

*with $f^{-1}$ being an inverse of a projection function f and where k and ξ stand respectively for camera intrinsic and distortion parameters.*

*40. A system for video based computer-aided surgery and diagnosis in anatomical regions of a patient comprising rigid, non-deformable anatomical parts or tissues comprising:*

*(i) a free-moving camera that is meant to acquire intra-operative images and video of an operating field, articular joint or anatomical cavity;*

*(ii) a visual marker, referred to as a World Marker or WM, which is an object that can be placed in an arbitrary location, and that comprises at least one planar facet with a known pattern having a system of coordinates that defines a global or world system of coordinates;*

*(iii) a touch-probe that is a tool or instrument comprising a handgrip and a tip, and that has at least one visual marker, referred to as a Tool Marker or TM, comprising at least one planar facet with a known pattern that defines a local system of coordinates where a position of the tip $P_T$ is known;*

*(iv) one or more surgical instruments for surgical execution, where each surgical instrument has at least one visual marker, also referred to as a Tool Marker or TM, comprising at least one planar facet with a known pattern that defines a local system of coordinates in which a position of relevant points and parts in the instrument are known; and*

*(v) an image processing system, that may correspond to or may be part of a computer and/or any other computing device, that receives as input images and video acquired by the camera (i), as well as commands that may be entered by a button panel, keyboard, camera buttons, foot switch and/or any other input interface, and that outputs processing results and guidance information to a display;*

*wherein the system is configured to execute steps comprising:*

*(vi) placement of the WM of (ii) in an arbitrary location with respect to an anatomical part of interest, such that the WM of (ii) and the anatomical part of interest do not move one with respect to the other;*

*(vii) 3D reconstruction of points in the surface of the rigid anatomical part of interest by using the touch-probe of (iii) to pin-point the points in the surface while keeping both the WM and the TM of the probe in a Field-of-View or FOV of the camera of (i) for determining the location of the touch-probe in the world system of coordinates to create 3D reconstruction results;*

(viii) use the 3D reconstruction results to perform measurements, make inferences, or overlay a surgical plan with an anatomical region of the patient, in which case a 3D registration method may be used for determining a transformation that maps local coordinates in a surgical plan into world coordinates in the placed WM; and (ix) assisted execution of a clinical procedure by using the surgical instruments of (iv) while keeping both WM and TMs of the surgical instruments in the FOV of the camera of (i) such that the surgical instruments can be located in world coordinates and real-time guidance can be provided by relating surgical instrument locations in world coordinates with the 3D reconstruction results and/or overlaid surgical plan;

where the camera in (i) is calibrated such that image points u expressed in pixel coordinates are mapped into image points x expressed in metric units according to $$x=f^{-1}(u;\ k,\ \xi)$$

with $f^{-1}$ being an inverse of a projection function f and where k and ξ stand respectively for camera intrinsic and distortion parameters.

41. A method for computer-aided execution of surgery and diagnosis in anatomical regions comprising rigid, non-deformable parts or tissues, the method comprising:

(i) placing a visual marker, referred to as the World Marker or WM, in an arbitrary location with respect to an anatomical part of interest such that the WM and the anatomical part of interest do not move with respect to each other, the visual marker comprising at least one planar facet with a known pattern whose system of coordinates defines a global or world system of coordinates;

(ii) acquiring, by a free-moving camera, intra-operative images and video of an operating field, articular joint, or anatomical cavity;

(iii) using a touch-probe, which is a tool or instrument comprising a handgrip and a tip, and that has at least one visual marker, referred to as Tool Marker or TM, comprising at least one planar facet with a known pattern that defines a local system of coordinates where a position of the tip PT is known, for pin-pointing points and/or outlining curves in the surface of the rigid anatomical part, while keeping both WM and TM of the probe in the Field-of-View or FOV of the camera to be visible in the acquired images and video;

(iv) receiving, by an image processing system that may correspond to, or may be part of, a computer and/or any other computing device, the images and video acquired in (iii), which are processed for determining the location of the touch-probe and reconstructing in 3D the pin-pointed points and/or outlined curves that are stored in memory in global or world coordinates;

(v) using the 3D reconstruction results to perform measurements, make inferences, or overlay a surgical plan with the patient's anatomy, in which case a 3D registration method may be used for determining the transformation that maps local coordinates in a surgical plan into world coordinates in the placed WM;

(vi) performing the surgical procedure with the required instruments, where each instrument has at least one visual marker, also referred to as Tool Marker or TM, comprising at least one planar facet with a known pattern that defines a local system of coordinates in which the position of relevant points and parts in the instrument are known, while keeping both WM and TMs of the instruments in the FOV of the camera to be visible in the acquired images and video;

(vii) receiving, by the image processing system, the images and video acquired in (vi), that are processed such that instruments can be located in world coordinates and real-time guidance can be provided by relating these locations with 3D reconstructions results and/or overlaid surgical plan; and (viii) outputting, by the image processing system, processing results and guidance information to a display, by either overlaying information in the input video using augmented reality (AR) techniques, or by animating models in a virtual reality (VR) environment;

where the camera is calibrated such that image points u expressed in pixel coordinates are mapped into image points x expressed in metric units according to $$x=f^{-1}(u;\ k,\ \xi)$$

with $f^{-1}$ being the inverse of a projection function f and where k and ξ stand respectively for camera intrinsic and distortion parameters.

42. A system for video based computer-aided surgery and diagnosis in anatomical regions of a patient comprising rigid, non-deformable anatomical parts or tissues comprising:

(i) a free-moving camera that is meant to acquire intra-operative images and video of an operating field, articular joint or anatomical cavity;

(ii) a visual marker, referred to as a World Marker or WM, which is an object that can be placed in an arbitrary location with respect to an anatomical part of interest, and that comprises at least one planar facet with a known pattern having a system of coordinates that defines a global or world system of coordinates;

(iii) a touch-probe that is a tool or instrument comprising a handgrip and a tip, and that has at least one visual marker, referred to as a Tool Marker or TM, comprising at least one planar facet with a known pattern that defines a local system of coordinates where a position of the tip PT is known;

(iv) one or more surgical instruments for surgical execution, where each surgical instrument has at least one visual marker, also referred to as a Tool Marker or TM, comprising at least one planar facet with a known pattern that defines a local system of coordinates in which a position of relevant points and parts in the instrument are known; and (v) an image processing system, that may correspond to or may be part of a computer and/or any other computing device, that receives as input images and video acquired by the camera (i), as well as commands that may be entered by a button panel, keyboard, camera buttons, foot switch and/or any other input interface, and that outputs processing results and guidance information to a display;

wherein the system is configured to execute steps comprising:

(vi) placement of the WM of (ii) in an arbitrary location with respect to an anatomical part of interest, such that the WM of (ii) and the rigid anatomical part of interest do not move one with respect to the other;

(vii) 3D reconstruction of points in the surface of the rigid anatomical part of interest by using the touch-probe of (iii) to pin-point the points in the surface while keeping both the WM and the TM of the probe in a Field-of-View or FOV of the camera of (i) for determining the

*location of the touch-probe in the world system of coordinates to create 3D reconstruction results;*

(*viii*) *use the 3D reconstruction results to perform measurements, make inferences. or overlay a surgical plan with an anatomical region of the patient, in which case a 3D registration method may be used for determining a transformation that maps local coordinates in a surgical plan into world coordinates in the placed WM; and*

(*ix*) *assisted execution of a clinical procedure by using the surgical instruments of* (*iv*) *while keeping both WM and TMs of the surgical instruments in the FOV of the camera of* (*i*) *such that the surgical instruments can be located in world coordinates and real-time guidance can be provided by relating surgical instrument locations in world coordinates;*

*wherein an arbitrary point P is reconstructed in global or world coordinates by acquiring an image as described in* (*vii*) *that undergoes the following processing steps:*

*detect, identify, and estimate a 3D pose C of the WM in camera coordinates;*

*detect, identify, and estimate a 3D pose* $\hat{T}$ *of the TM in camera coordinates;*

*reconstruct a point P that is in contact with the tip of the touch-probe by making*

$$\begin{pmatrix} P \\ 1 \end{pmatrix} = C^{-1}\hat{T}\begin{pmatrix} P_T \\ 1 \end{pmatrix};$$

*and store 3D coordinates of point P in a memory.*

*43. A system for video based computer-aided surgery and diagnosis in anatomical regions of a patient comprising rigid, non-deformable anatomical parts or tissues comprising:*

(*i*) *a free-moving camera that is meant to acquire intra-operative images and video of an operating field, articular joint or anatomical cavity;*

(*ii*) *a visual marker, referred to as a World Marker or WM, which is an object that can be placed in an arbitrary location with respect to an anatomical part of interest, and that comprises at least one planar facet with a known pattern having a system of coordinates that defines a global or world system of coordinates;*

(*iii*) *a touch-probe that is a tool or instrument comprising a handgrip and a tip, and that has at least one visual marker, referred to as a Tool Marker or TM, comprising at least one planar facet with a known pattern that defines a local system of coordinates where a position of the tip PT is known;*

(*iv*) *one or more surgical instruments for surgical execution, where each surgical instrument has at least one visual marker, also referred to as a Tool Marker or TM, comprising at least one planar facet with a known pattern that defines a local system of coordinates in which a position of relevant points and parts in the instrument are known; and*

(*v*) *an image processing system, that may correspond to or may be part of a computer and/or any other computing device, that receives as input images and video acquired by the camera* (*i*), *as well as commands that may be entered by a button panel, keyboard, camera buttons, foot switch and/or any other input interface, and that outputs processing results and guidance information to a display;*

*wherein the system is configured to execute steps comprising:*

(*vi*) *placement of the WM of* (*ii*) *in an arbitrary location with respect to an anatomical part of interest, such that the WM of* (*ii*) *and the rigid anatomical part of interest do not move one with respect to each other;*

(*vii*) *3D reconstruction of points in the surface of the rigid anatomical part of interest by using the touch-probe of* (*iii*) *to pin-point the points in the surface while keeping both the WM and the TM of the probe in a Field-of-View or FOV of the camera of* (*i*) *for determining the location of the touch-probe in the world system of coordinates to create 3D reconstruction results;*

(*viii*) *use the 3D reconstruction results to perform measurements, make inferences, or overlay a surgical plan with an anatomical region of the patient, in which case a 3D registration method may be used for determining a transformation that maps local coordinates in a surgical plan into world coordinates in the placed WM; and*

(*ix*) *assisted execution of a clinical procedure by using the surgical instruments of* (*iv*) *while keeping both WM and TMs of the surgical instruments in the FOV of the camera of* (*i*) *such that the surgical instruments can be located in world coordinates and real-time guidance can be provided by relating surgical instrument locations in world coordinates; wherein the assisted execution of the clinical procedure is accomplished by acquiring continuous video according to* (*ix*), *the video comprising a plurality of images, with each consecutive image undergoing the following processing steps in real-time:*

*a. detect, identify, and estimate a 3D pose C of the WM in camera coordinates;*

*b. detect, identify, and estimate a 3D pose* $\hat{T}$ *of the TM of each of the one or more surgical instruments in camera coordinates;*

*c. compute the 3D pose T of TM in WM coordinates using the following equation:*

$$T=C^{-1}\hat{T}$$

*d. map the information of surgical instrument calibration, that can be points, axes, or CAD models, into world coordinates using the rigid transformation T;*

*e. relate the surgical instrument calibration information with 3D data stored in memory to make measurements and inferences for the purpose of real-time guidance; and*

*f. display aiding features either by using Augmented Reality (AR), in which case guidance information is overlaid in image or by animating a Virtual Reality (VR) 3D model.*

*44. A system for computer-aided surgery and diagnosis in an anatomical region of a patient comprising a rigid, non-deformable anatomical part, the system comprising:*

*a free-moving camera to acquire intra-operative images, video, or images and video of an operating field,*

*where the free-moving camera is calibrated such that image points u expressed in pixel coordinates are mapped into image points x expressed in metric units according to*

$$x=f^{-1}(u;\ k,\ \xi)$$

*with* $f^{-1}$ *being the inverse of a projection function f and where k and* $\xi$ *stand respectively for camera intrinsic and distortion parameters;*

*a world marker (WM) comprising an object configured to be placed with respect to the anatomical part such that the WM and the anatomical part do not move with respect to each other, wherein the object comprises a first known pattern that defines a first system of coordinates;*

*one or more surgical instruments, wherein each surgical instrument has at least one tool marker (TM), each TM comprising a respective second known pattern that defines a second system of coordinates in which a position of relevant points and parts of the surgical instrument are known; and*

*an image processing system configured to:*

*receive the images, video, or images and video acquired by the camera, wherein the images, video, or images and video include the WM, one or more of the TMs, or the WM and one or more of the TMs in a field of view of the camera;*

*receive a 3D reconstruction of points of the anatomical part in the first coordinate system; and*

*output information derived from the 3D reconstruction to a display to assist execution of a clinical procedure using the one or more surgical instruments while keeping the WM, one or more of the TMs, or the WM and one or more of the TMs in the field of view of the camera, wherein the output comprises real-time guidance including a respective location of each surgical instrument in the first coordinate system.*

*45. A method for computer-aided execution of surgery and diagnosis in an anatomical region comprising a rigid anatomical part, the method comprising:*

*placing a world marker (WM) with respect to the anatomical part such that the WM and the anatomical part do not move with respect to each other, the WM comprising a known pattern defining a first system of coordinates;*

*acquiring, by a free-moving camera, first intra-operative images, video, or images and video, while keeping the WM in a field of view of the camera,*

*wherein the free-moving camera is calibrated such that image points u expressed in pixel coordinates are mapped into image points x expressed in metric units according to*

$$x=f^{-1}(u;\ k,\ \xi)$$

*with $f^{-1}$ being the inverse of a projection function f and where k and ξ stand respectively for camera intrinsic and distortion parameters;*

*receiving a 3D reconstruction of points of the anatomical part in the first coordinate system;*

*during a surgical procedure performed with one or more surgical instruments, wherein each surgical instrument has a respective tool marker (TM), each TM comprising a respective known pattern that defines a respective second system of coordinates in which positions of one or more points on the instrument are known, acquiring, by the camera, second intra-operative images, video, or images and video, while keeping the WM and the surgical instrument TMs in a field of view of the camera;*

*processing, by the image processing system, the second images, video, or images and video to determine locations of the surgical instruments in the first coordinate system; and*

*outputting information derived from the 3D reconstruction to a display to assist execution of a clinical procedure using the one or more surgical instruments while keeping the WM, one or more of the TMs, or the WM and one or more of the TMs in the field of view of the camera, wherein the output comprises real-time guidance including a respective location of each surgical instrument in the first coordinate system.*

*46. A system for computer-aided surgery and diagnosis in an anatomical region of a patient comprising a rigid, non-deformable anatomical part, the system comprising:*

*a camera to acquire intra-operative images, video, or images and video of an operating field,*

*where the camera is calibrated such that image points u expressed in pixel coordinates are mapped into image points x expressed in metric units according to*

$$x=f^{-1}(u;\ k,\ \xi)$$

*with $f^{-1}$ being the inverse of a projection function f and where k and ξ stand respectively for camera intrinsic and distortion parameters;*

*a world marker (WM) comprising an object configured to be placed with respect to the anatomical part such that the WM and the anatomical part do not move one with respect to each other, wherein the object comprises a first known pattern that defines a first system of coordinates;*

*an instrument comprising a surgical instrument or a point location device, wherein the camera is rigidly coupled to the instrument such that camera has a known positional relationship with a portion of the instrument;*

*an image processing system configured to:*

*receive the images, video, or images and video acquired by the camera, wherein the images, video, or images and video include the WM in a field of view of the camera; receive a 3D reconstruction of points of the anatomical part in the first coordinate system; and*

*output information derived from the 3D reconstruction to a display to assist execution of a clinical procedure using the instrument while keeping the WM in the field of view of the camera, wherein the output comprises a location of the instrument in the first coordinate system.*

*47. A system for computer-aided surgery and diagnosis in an anatomical region of a patient comprising a rigid, non-deformable anatomical part, the system comprising:*

*a free-moving camera to acquire intra-operative images, video, or images and video of an operating field,*

*where the free-moving camera is calibrated such that image points u expressed in pixel coordinates are mapped into image points x expressed in metric units according to*

$$x=f^{-1}(u;\ k,\ \xi)$$

*with $f^{-1}$ being the inverse of a projection function f and where k and ξ stand respectively for camera intrinsic and distortion parameters;*

*a world marker (WM) comprising an object configured to be placed with respect to the anatomical part such that the WM and the anatomical part do not move with respect each other; and*

*an image processing system configured to:*

*receive the images, video, or images and video acquired by the free-moving camera, wherein the images, video, or images and video include the WM in a field of view of the camera;*

*receive a 3D reconstruction of points of the anatomical part in a first coordinate system defined using the WM; and*

*output information derived from the 3D reconstruction for display to assist execution of a clinical procedure using*

*a surgical instrument while keeping the WM in the field of view of the camera, wherein the output comprises guidance including a location of a surgical instrument in the first coordinate system.*

* * * * *